US012807594B2

(12) United States Patent
Congreve et al.

(10) Patent No.: US 12,807,594 B2
(45) **Date of Patent: *Nov. 24, 2026**

(54) H4 ANTAGONIST COMPOUNDS

(71) Applicant: NXERA PHARMA UK LIMITED, Cambridge (GB)

(72) Inventors: Miles Stuart Congreve, Cambridge (GB); Charlotte Fieldhouse, Cambridge (GB); Nigel Alan Swain, Cambridge (GB); Mark Pickworth, Cambridge (GB); Duncan Robert Hannah, Cambridge (GB)

(73) Assignee: NXERA PHARMA UK LIMITED, Cambridgeshire (GB)

( * ) Notice: Subject to any disclaimer, the term of this patent is extended or adjusted under 35 U.S.C. 154(b) by 852 days.

This patent is subject to a terminal disclaimer.

(21) Appl. No.: 17/920,583

(22) PCT Filed: Apr. 22, 2021

(86) PCT No.: PCT/GB2021/050971

§ 371 (c)(1),
(2) Date: Oct. 21, 2022

(87) PCT Pub. No.: WO2021/214469

PCT Pub. Date: Oct. 28, 2021

(65) Prior Publication Data

US 2023/0167094 A1 Jun. 1, 2023

(30) Foreign Application Priority Data

Apr. 22, 2020 (GB) ...................................... 2005858

(51) Int. Cl.
*C07D 403/14* (2006.01)
*C07D 401/14* (2006.01)

(52) U.S. Cl.
CPC ......... *C07D 403/14* (2013.01); *C07D 401/14* (2013.01)

(58) Field of Classification Search
CPC .................................................... C07D 403/14
See application file for complete search history.

(56) References Cited

FOREIGN PATENT DOCUMENTS

| | | | |
|---|---|---|---|
| CN | 104583215 | A | 4/2015 |
| EP | 1 103 551 | A1 | 5/2001 |
| RU | 2 489 430 | C2 | 8/2013 |
| RU | 2 573 828 | C2 | 1/2016 |
| WO | WO 2005/054239 | A1 | 6/2005 |
| WO | WO 2007/072163 | A2 | 6/2007 |
| WO | WO 2008/031556 | A2 | 3/2008 |
| WO | WO 2008/060766 | A2 | 5/2008 |
| WO | WO 2008/100565 | A1 | 8/2008 |
| WO | WO 2009/068512 | A1 | 6/2009 |
| WO | WO 2009/077608 | A1 | 6/2009 |
| WO | WO 2009/080721 | A2 | 7/2009 |
| WO | WO 2010/059658 | A1 | 5/2010 |
| WO | WO 2010/108059 | A1 | 9/2010 |
| WO | WO 2011/059839 | A1 | 5/2011 |
| WO | WO 2011/076878 | A1 | 6/2011 |
| WO | WO 2014/033196 | A1 | 3/2014 |
| WO | WO 2014/078637 | A1 | 5/2014 |
| WO | WO 2018/023029 | A1 | 2/2018 |
| WO | WO 2020/079457 | A1 | 4/2020 |

OTHER PUBLICATIONS

Altenbach et al., "Structure-Activity Studies on a Series of a 2-Aminopyrimidine-Containing Histamine H4 Receptor Ligands," Journal of Medicinal Chemistry, vol. 51, 2008, pp. 6571-6580.
Beasley et al., "Risk factors for asthma: is prevention possible?," The Lancet, vol. 386, 2015, pp. 1075-1085.
Corrêa et al., "Histamine H4 Receptor Ligands: Future Applications and State of Art," Chemical Biology & Drug Design, vol. 85, 2015, pp. 461-480.
International Preliminary Report on Patentability, dated Apr. 14, 2021, and Written Opinion of the International Searching Authority, dated Jun. 22, 2021, for International Application No. PCT/GB2019/052997.
Mollanazar et al., "Mediators of Chronic Pruritus in Atopic Dermatitis: Getting the Itch Out?," Clinical Reviews in Allergy & Immunology, vol. 51, 2016, pp. 263-292.
Liu et al., "Comparison of Human, Mouse, Rat, and Guinea Pig Histamine H4 Receptors Reveals Substantial Pharmacological Species Variation," The Journal of Pharmacology and Experimental Therapeutics, vol. 299, No. 1, 2001, pp. 121-130.
Andaloussi et al., "A novel series of histamine Ha receptor antagonists based on the pyrido[3,2-d]pyrimidine scaffold: Comparison of hERG binding and target residence time with PF-3893787", Bioorganic & Medicinal Chemistry Letters, 2013, vol. 23, pp. 2663-2670.
International Search Report, issued in PCT/GB2021/050971, dated Jun. 22, 2021.
Ko et al., "Discovery of a Novel Highly Selective Histamine H4 Receptor Antagonist for the Treatment of Atopic Dermatitis", J. Med. Chem. 2018, vol. 61, pp. 2949-2961.
Mowbray et al., "Challenges of drug discovery in novel target space. The discovery and evaluation of PF-3893787: A novel histamine H4 receptor antagonist", Bioorganic & Medicinal Chemistry Letters, 2011, vol. 21, pp. 6596-6602.

(Continued)

*Primary Examiner* — Brian E McDowell
(74) *Attorney, Agent, or Firm* — Birch, Stewart, Kolasch & Birch, LLP

(57) ABSTRACT

The disclosures herein relate to novel compounds, their use as Histamine H4 receptor antagonists and their use in treating, preventing, ameliorating, controlling or reducing the risk of disorders associated with H4 receptors, as represented by Formula (1).

(1)

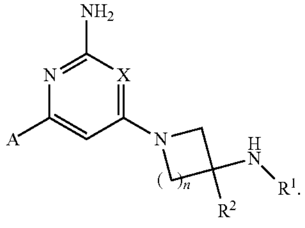

9 Claims, 1 Drawing Sheet

(56) References Cited

OTHER PUBLICATIONS

Savall et al., "Discovery and SAR of 6-Alkyl-2,4-diaminopyrimidines as Histamine $H_4$ Receptor Antagonists", J. Med. Chem., 2014, vol. 57, pp. 2429-2439.
Thurmond et al., "Pharmacology and Clinical Activity of Toreforant, a Histamine $H_4$ Receptor Antagonist", Annals of Pharmacology and Pharmaceutics, 2017, vol. 2, Issue 1, Article 1013, total 11 pages.
Venable et al., "Preparation and Biological Evaluation of Indole, Benzimidazole, and Thienopyrrole Piperazine Carboxamides: Potent Human Histamine $H_4$ Antagonists", J. Med. Chem., 2005, vol. 48, No. 26, pp. 8289-8298.
Written Opinion of the International Searching Authority, issued in PCT/GB2021/050971, dated Jun. 22, 2021.

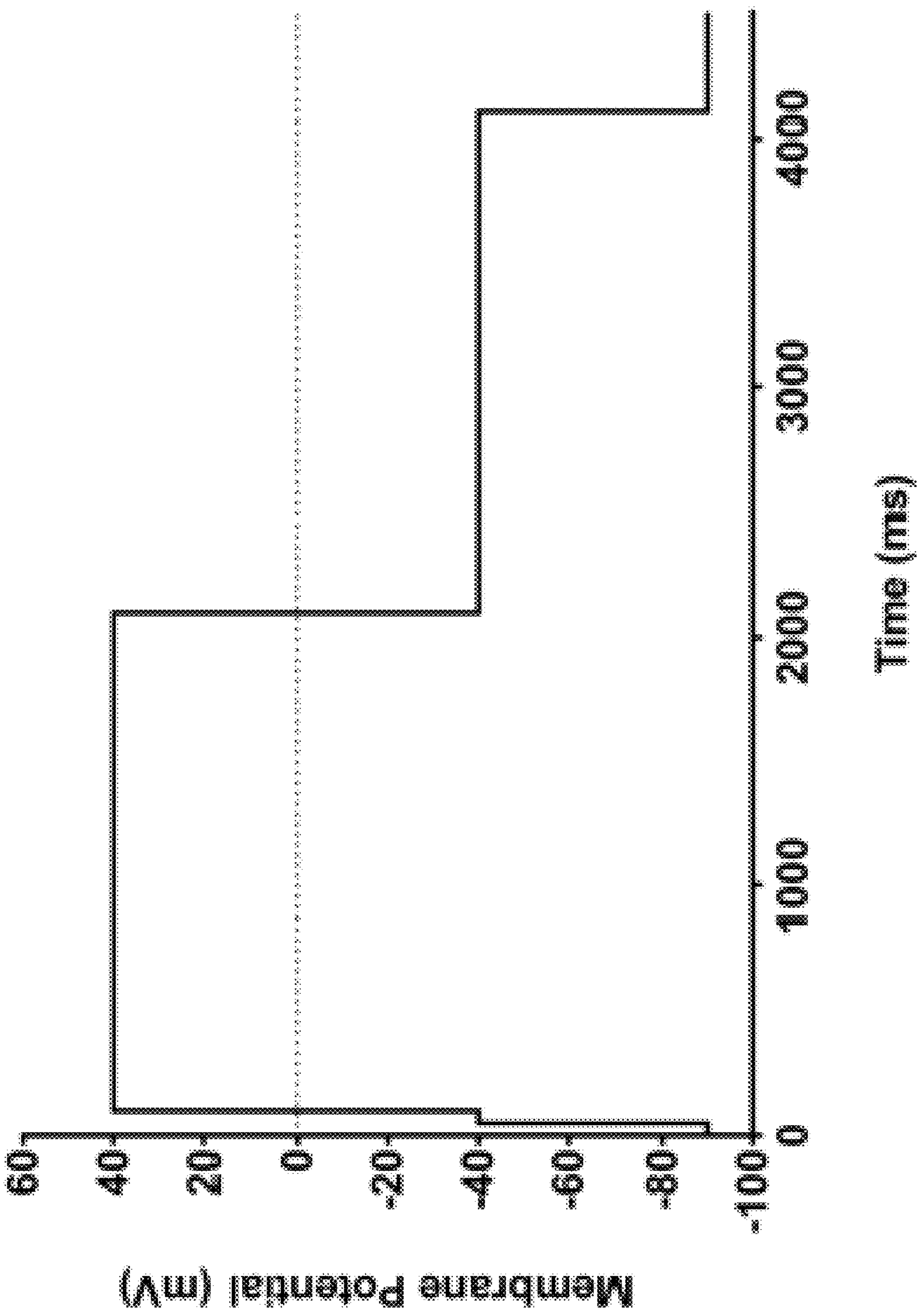
Membrane Potential (mV)
60
40
20
0
-20
-40
-60
-80
-100
0
1000
2000
3000
4000
Time (ms)

H4 ANTAGONIST COMPOUNDS

This application relates to novel compounds and their use as Histamine H4 receptor antagonists. Compounds described herein may be useful in the treatment or prevention of diseases in which H4 receptors are involved. The application is also directed to pharmaceutical compositions comprising these compounds and the manufacture and use of these compounds and compositions in the prevention or treatment of such diseases in which H4 receptors are involved.

BACKGROUND OF THE INVENTION

Histamine is a short-acting biogenic amine generated in mast cells where it is stored in cytosolic granules and released in response to various immunological and non-immunological stimuli. Histamine release from mast cells has been traditionally associated with mild to severe signs and symptoms that characterize hypersensitivity reactions, including erythema, urticaria, itching, tachycardia, hypotension, ventricular fibrillations, bronchospasm, and cardiac and respiratory arrest. To date, numerous additional sources have been identified, including basophils, neurons and cancer cells. In addition to modulating a wide range of physiological processes, histamine is implicated in pathological conditions including allergies and anaphylaxis, asthma and chronic inflammation, autoimmune, cardiovascular, neuropsychiatric and endocrine disorders as well as cancer.

Histamine exerts its pleiotropic actions mainly through binding to four types of G-protein-coupled receptors (GPCRs), designated as H1-H4 that are differentially expressed in various cell types and exhibit considerable variations among species. The H2 receptor is responsible for gastric acid secretion; the H3 receptor controls the release of histamine and other neuromodulators in the CNS and the H1 receptor is associated with wakefulness and inflammatory response.

Identified in 2000, the high affinity H4 receptor displays constitutive activity and is expressed mostly, but not exclusively on cells of the immune system including mast cells, monocytes, dendritic cells, eosinophils, basophils, neutrophils, and T cells. This discovery led to the attractive prospect of a new drug target with therapeutic potential in acute and chronic inflammation, autoimmune disease, host defense and neuropathic pain.

The H4R shares only 40% homology with its nearest neighbour the H3R and neither H2 nor H1 antagonists were shown to inhibit histamine induced eosinophil chemotaxis. Histamine has been shown to inhibit forskolin-induced cAMP responses in a pertussis toxin (PTx)-sensitive manner, suggesting that H4R signals via heterotrimeric Gai/o proteins. Transient expression of the H4R in heterologous cell systems (e.g. HEK293 cells) is a widely used method to measure H4 ligand signaling and binding to generate estimates of functional potency and receptor affinity respectively.

The discovery of H4R antagonists using these techniques and their study in various animal disease models including asthma, chronic pruritus, dermatitis, rheumatoid arthritis, gastric ulcerogenesis and colitis has confirmed H4R antagonism leads to a profound anti-inflammatory effect and has validated the therapeutic benefit for targeting this receptor. The first H4R antagonist phase 2a clinical trial in patients suffering from moderate-to-severe atopic dermatitis has already been conducted, further confirming H4 as a druggable target in patients Notwithstanding a number of published H4R ligands, there remains a need to develop new H4R antagonists with good drug candidate quality. These antagonists should display excellent low nM potency and affinity with full selectivity against H1-H3 receptors. They should display no agonist activity due to risks associated with the induction of pro-inflammatory responses, and ideally display a similar pharmacological profile across species to support PK/PD in various animal models of disease. They should be metabolically stable, with excellent PK, non-toxic and show excellent H4 specificity in broad safety panel profiling.

The human ether-a-go-go-related gene (hERG) encodes the pore-forming subunit of the rapidly activating delayed rectifier potassium channel (IKr), which plays an important role in ventricular repolarisation and in determining the QT-interval of the electrocardiogram with QT-interval being the time taken for ventricular depolarisation and repolarisation. It is widely acknowledged that hERG is highly susceptible to inhibition by a wide range of structurally diverse compounds. When the channels ability to conduct electrical current across the cell membrane is inhibited or compromised by application of drugs, it can result in a potentially fatal disorder called QT syndrome. A number of clinically successful drugs in the market have had the tendency to inhibit hERG, and create a concomitant risk of sudden death, as a side-effect, which has made hERG inhibition an important anti- target that must be avoided during drug development.

Compounds of the invention are antagonists of the H4 receptor. Certain compounds have a low hERG inhibition, making these particularly beneficial.

BRIEF DESCRIPTION OF THE DRAWING

The FIGURE shows the QPatch voltage protocol used for the hERG assay.

THE INVENTION

The present invention provides compounds having activity as H4 receptor antagonists. More particularly, the invention provides compounds that combine H4 receptor antagonism with low hERG activity.

Accordingly, the invention provides a compound of the formula (1):

(1)

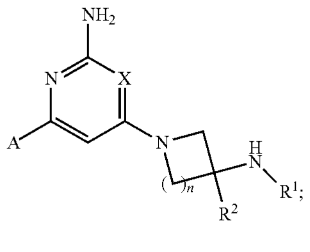

or a salt thereof, wherein;

X is CH or N;

n is 1 or 2;

$R^1$ is selected from H or $C_{1-3}$ alkyl;

$R^2$ is H; and

A represents an optionally substituted pyrazole ring;

wherein the compound is selected from the group consisting of:

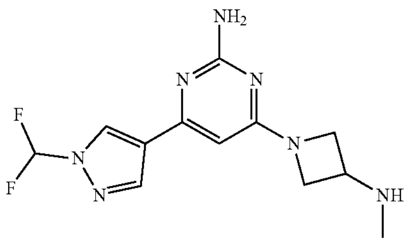 [SMILES: CNC1CN(c2cc(-c3cnn(C(F)F)c3)nc(N)n2)C1]
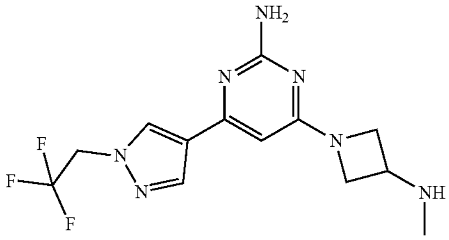 [SMILES: CNC1CN(c2cc(-c3cnn(CC(F)(F)F)c3)nc(N)n2)C1]
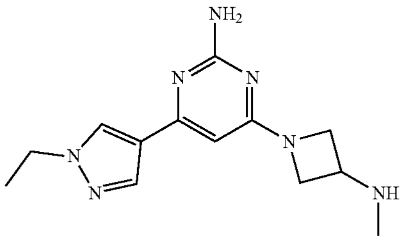 [SMILES: CCn1cc(-c2cc(N3CC(NC)C3)nc(N)n2)cn1]
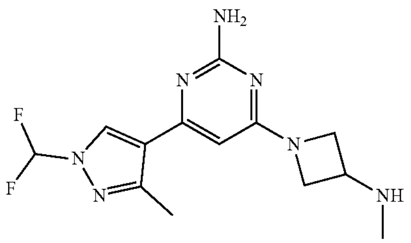 [SMILES: CNC1CN(c2cc(-c3cn(C(F)F)nc3C)nc(N)n2)C1]
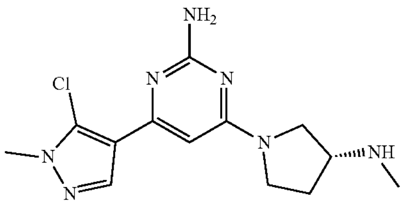
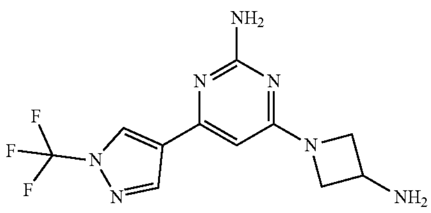 [SMILES: Nc1nc(-c2cnn(C(F)(F)F)c2)cc(N2CC(N)C2)n1]
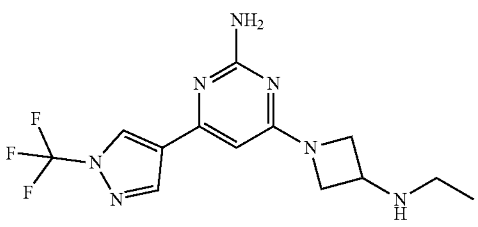 [SMILES: CCNC1CN(c2cc(-c3cnn(C(F)(F)F)c3)nc(N)n2)C1]
-continued
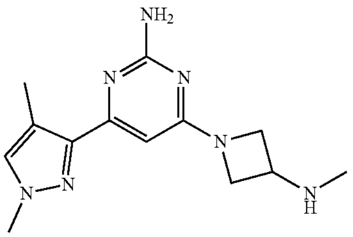 [SMILES: CNC1CN(c2cc(-c3nn(C)cc3C)nc(N)n2)C1]
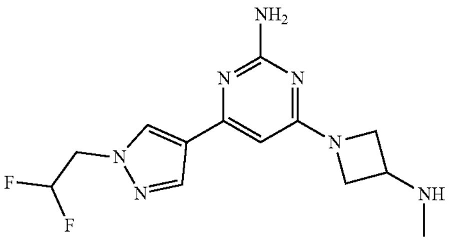 [SMILES: CNC1CN(c2cc(-c3cnn(CC(F)F)c3)nc(N)n2)C1]
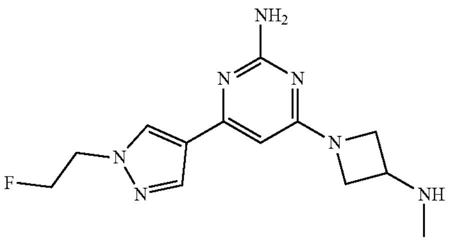 [SMILES: CNC1CN(c2cc(-c3cnn(CCF)c3)nc(N)n2)C1]
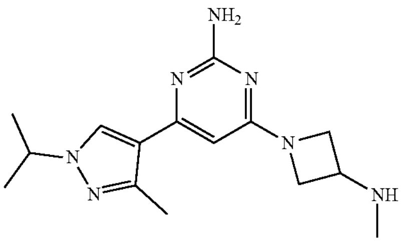 [SMILES: CNC1CN(c2cc(-c3cn(C(C)C)nc3C)nc(N)n2)C1]
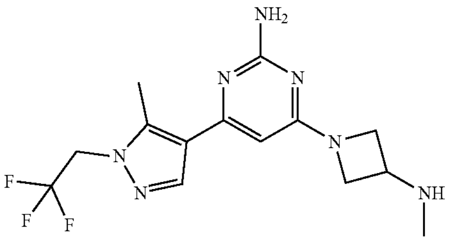 [SMILES: CNC1CN(c2cc(-c3cnn(CC(F)(F)F)c3C)nc(N)n2)C1]
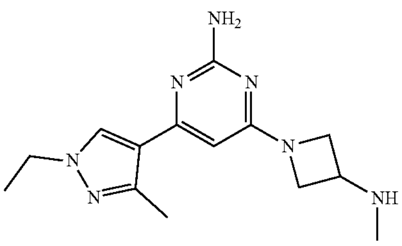 [SMILES: CCn1cc(-c2cc(N3CC(NC)C3)nc(N)n2)c(C)n1]
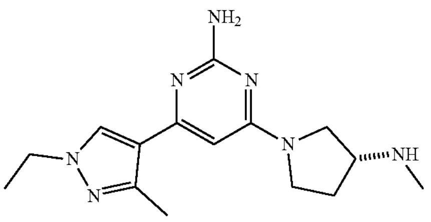 [SMILES: CCn1cc(-c2cc(N3CC[C@@H](NC)C3)nc(N)n2)c(C)n1]

-continued
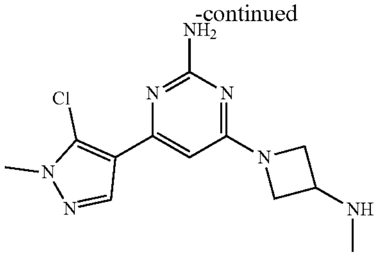
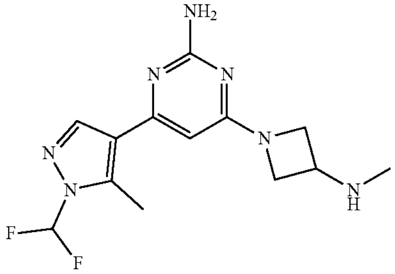
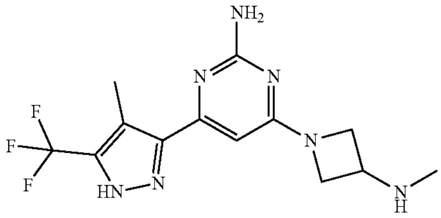
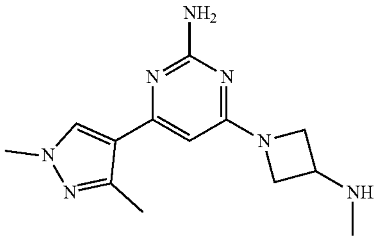
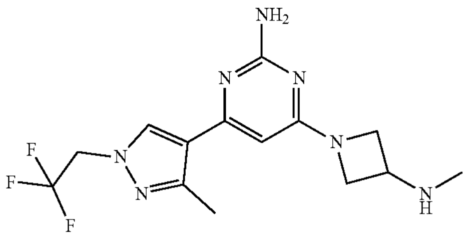
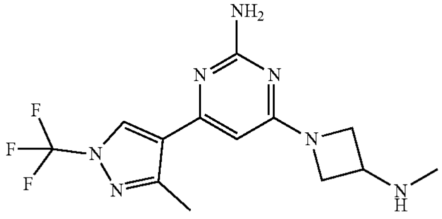
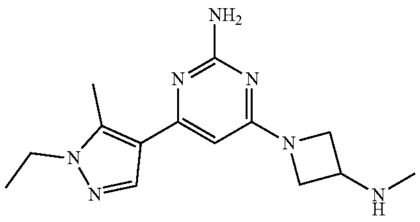
-continued
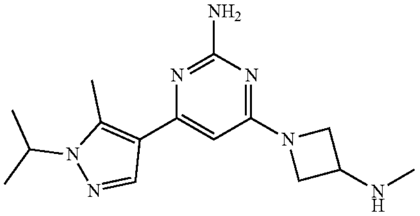
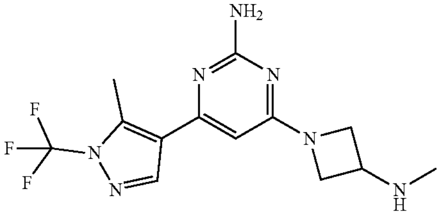
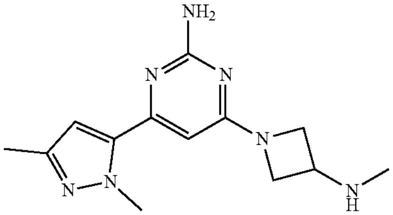
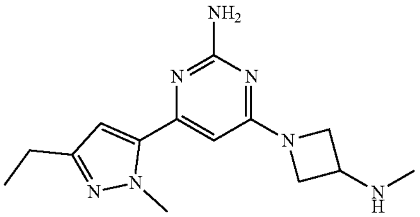
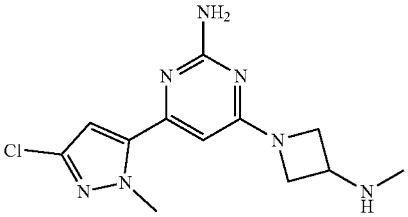
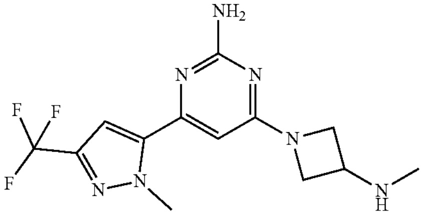
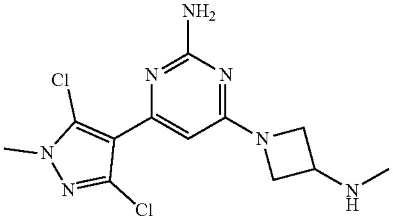
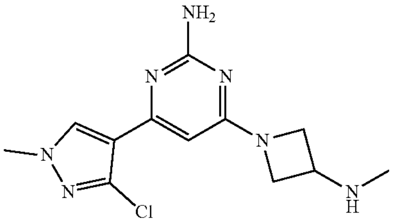

-continued

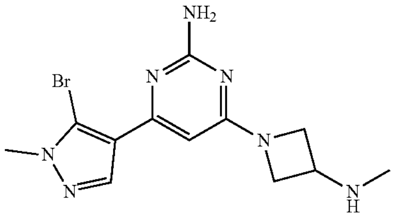

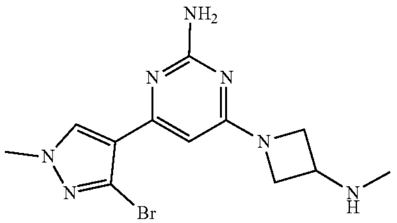

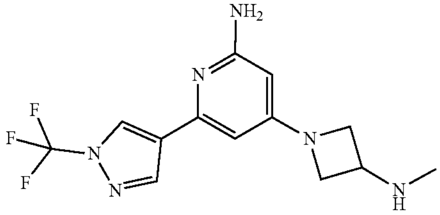

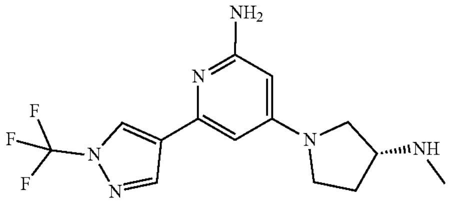

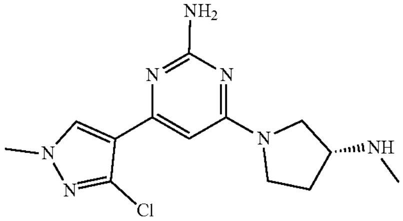

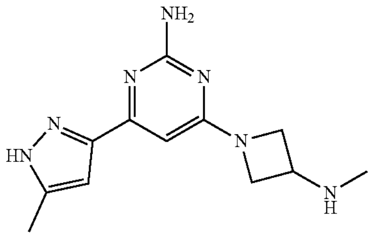

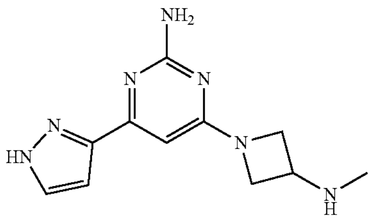

-continued

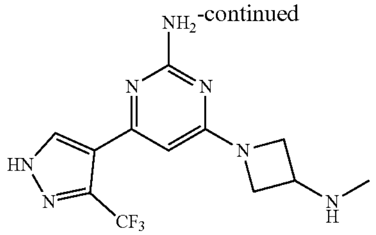

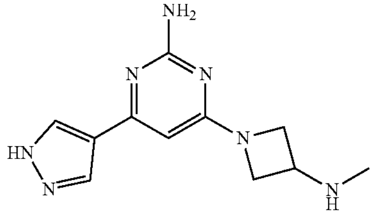

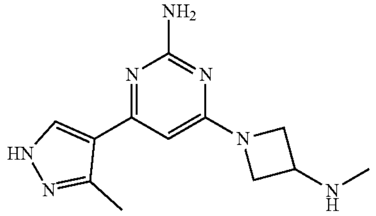

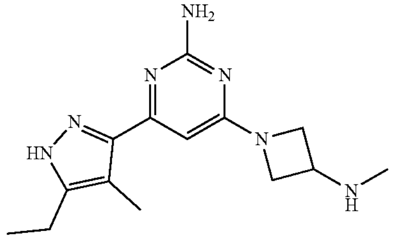

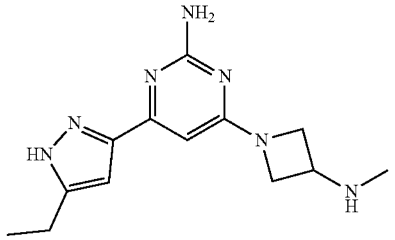

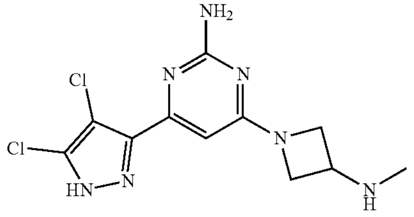

or a salt thereof.

The compounds may be used as H4 receptor antagonists. The compounds may be used in the manufacture of medicaments. The compounds or medicaments may be for use in treating, preventing, ameliorating, controlling or reducing the risk of inflammatory disorders including asthma, chronic pruritus, dermatitis, rheumatoid arthritis, gastric ulcerogenesis and colitis.

DETAILED DESCRIPTION OF THE INVENTION

The invention relates to novel compounds. The invention also relates to the use of novel compounds as antagonists of the H4 receptor. The invention further relates to the use of novel compounds in the manufacture of medicaments for use as H4 receptor antagonists or for the treatment of H4 system dysfunction. The invention further relates to compounds, compositions and medicaments which are selective H4 receptor antagonists.

The invention further relates to compounds, compositions and medicaments useful for the treatment of acute and chronic inflammation, autoimmune disease, host defense disorders and neuropathic pain. The invention further relates to compounds, compositions and medicaments useful for the treatment of inflammatory disorders including asthma, chronic pruritus, dermatitis, rheumatoid arthritis, gastric ulcerogenesis and colitis.

Compounds of the invention include compounds of the formula (1):

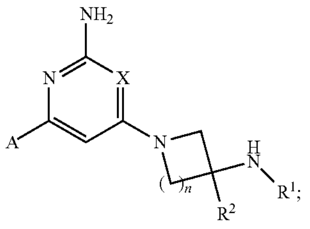

(1)

or a salt thereof, wherein;

X is CH or N;

n is 1 or 2;

$R^1$ is selected from H or $C_{1-3}$ alkyl;

$R^2$ is H; and

A represents an optionally substituted pyrazole ring;

wherein the compound is selected from the group consisting of:

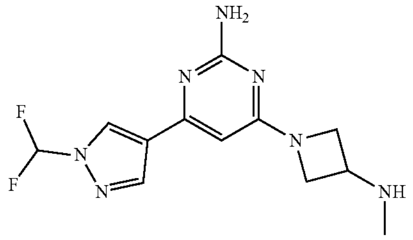

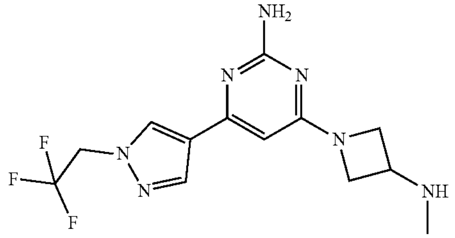

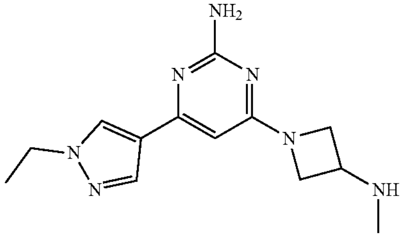

-continued

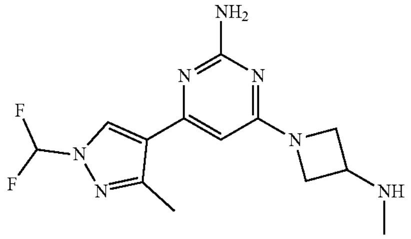

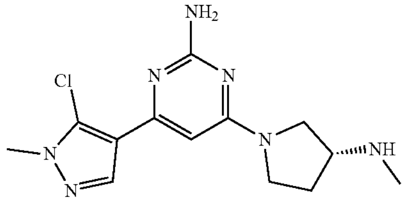

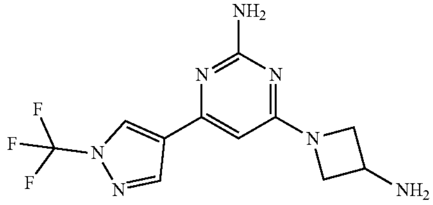

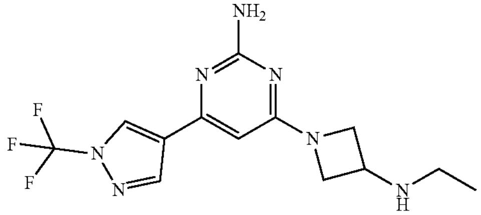

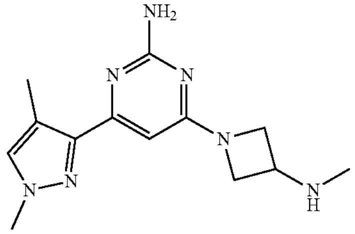

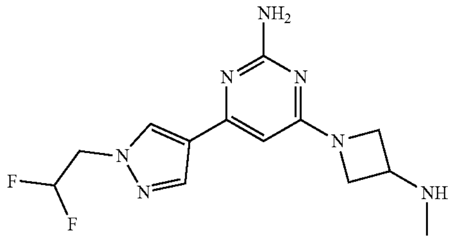

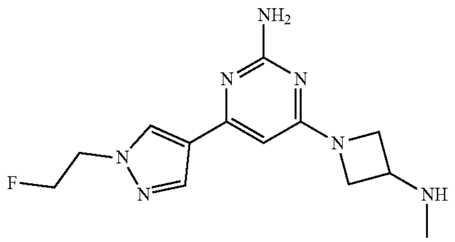

-continued
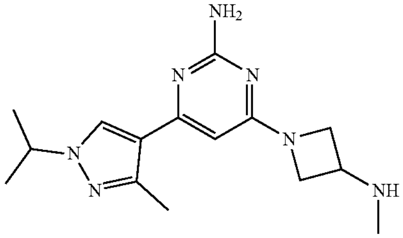
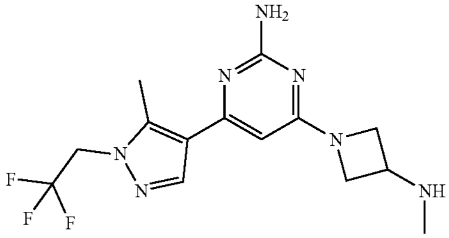
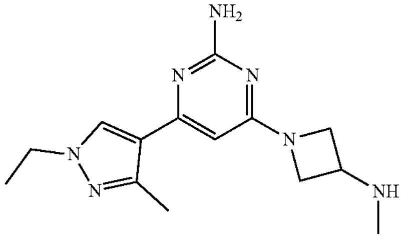
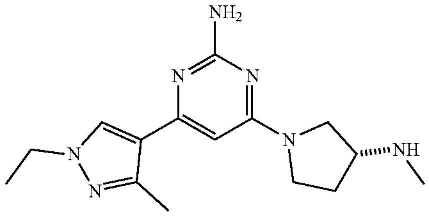
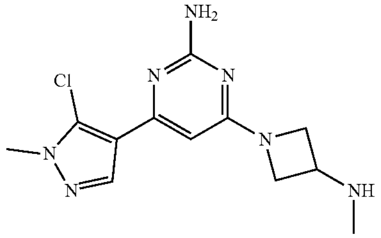
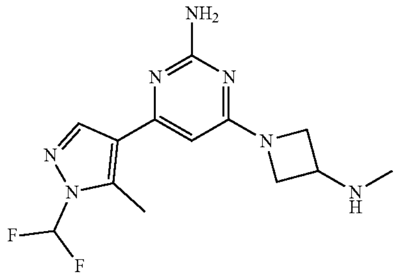
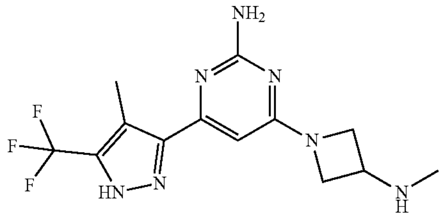
-continued
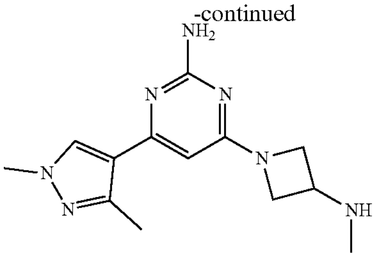
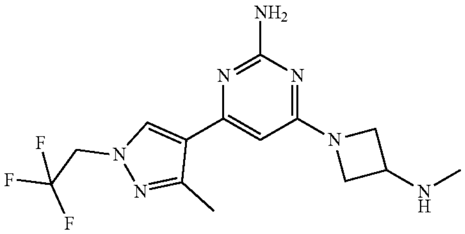
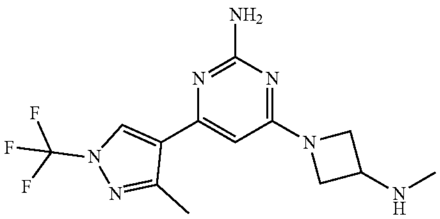
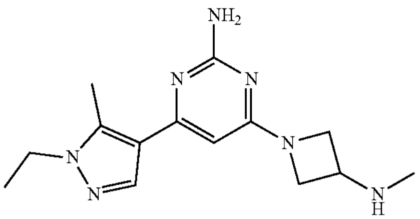
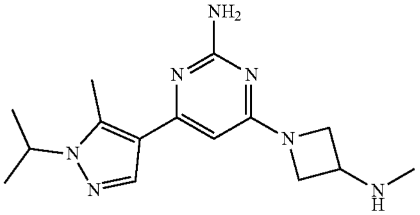
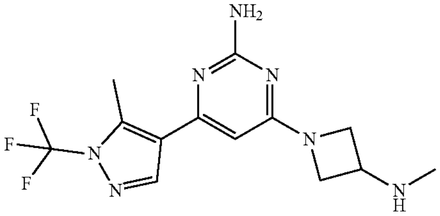
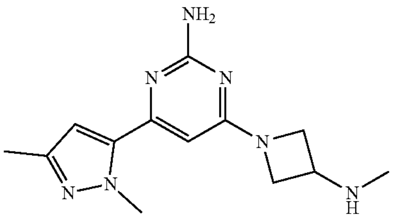

-continued
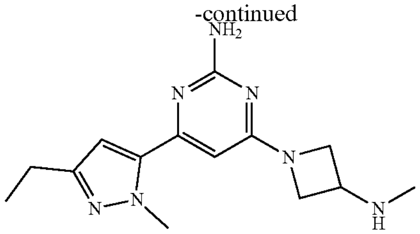
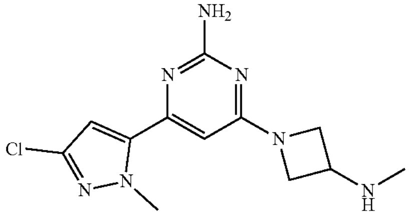
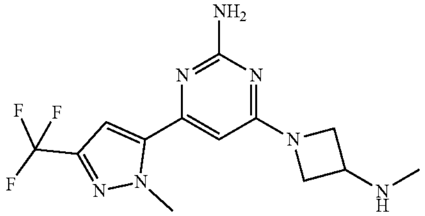
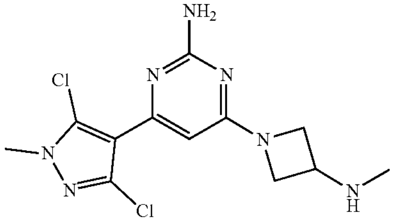
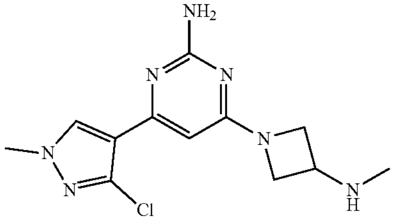
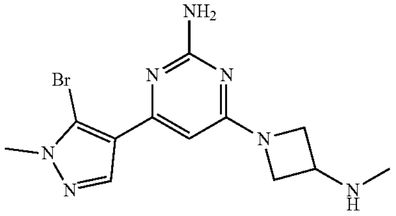
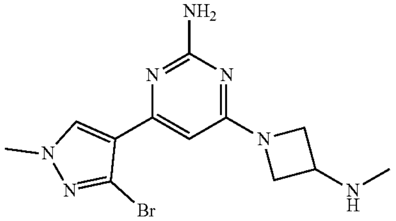
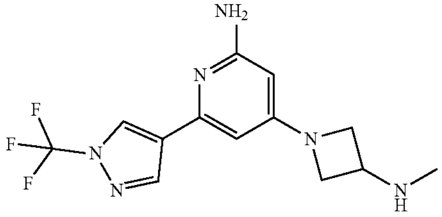
-continued
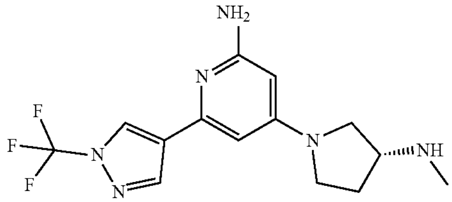
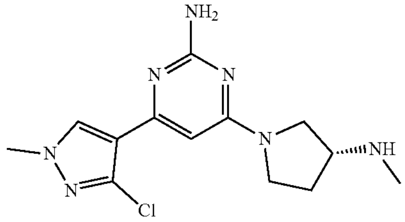
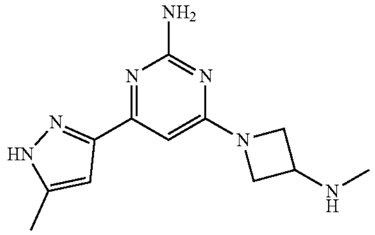
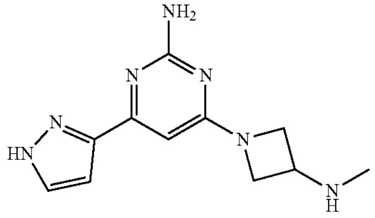
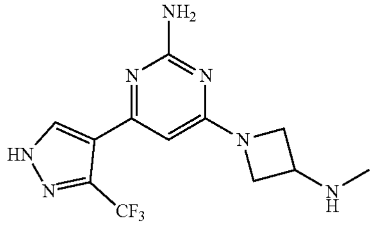
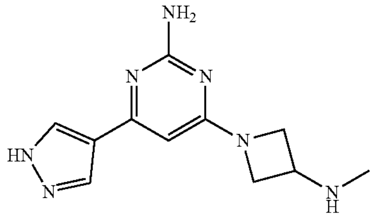
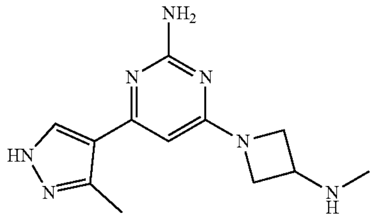

-continued
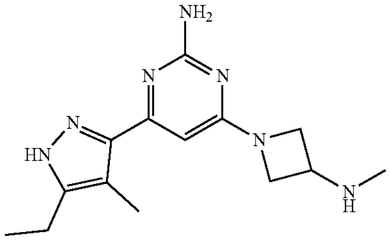
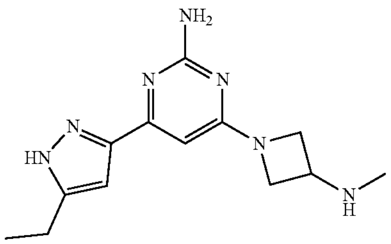
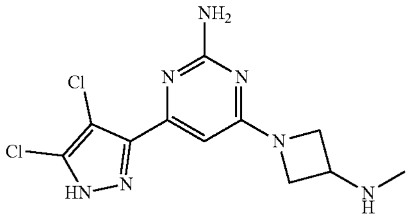
or a salt thereof.
Compounds of the invention include compounds of the formula (1a):
(1a)
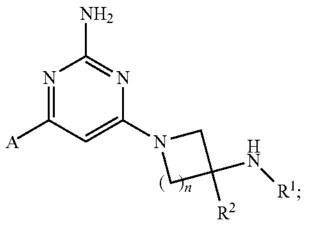
or a salt thereof, wherein;
n is 1 or 2;
$R^1$ is selected from H or $C_{1-3}$ alkyl;
$R^2$ is H; and
A represents an optionally substituted pyrazole ring;
wherein the compound is selected from the group consisting of:
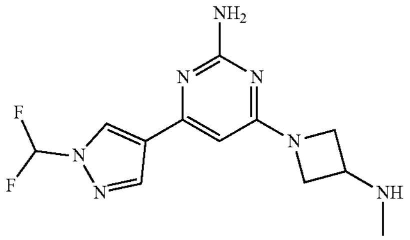
-continued
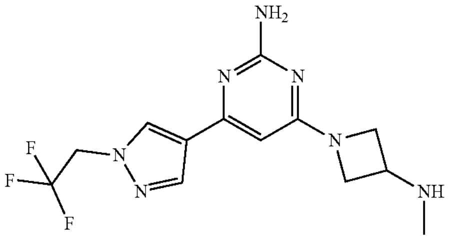
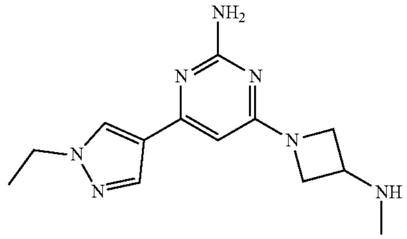
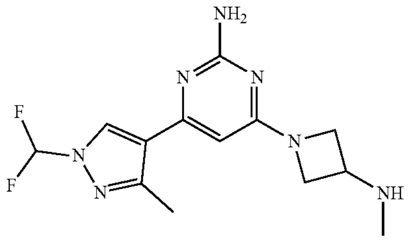
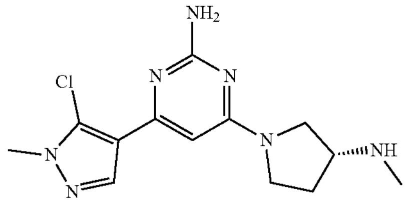
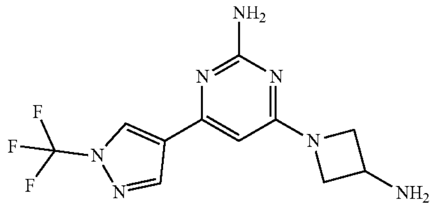
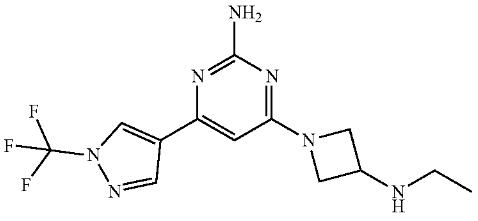
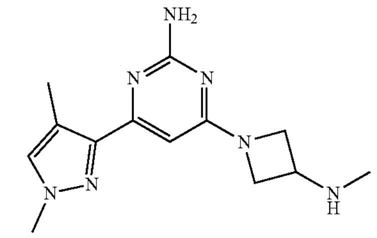

-continued
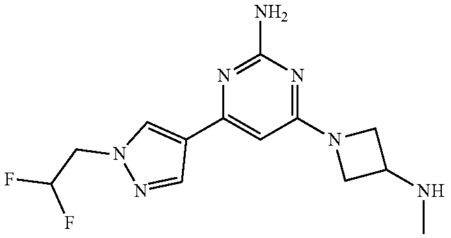
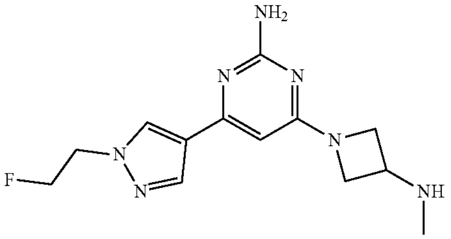
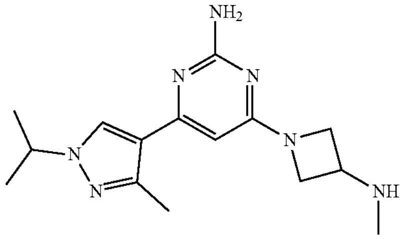
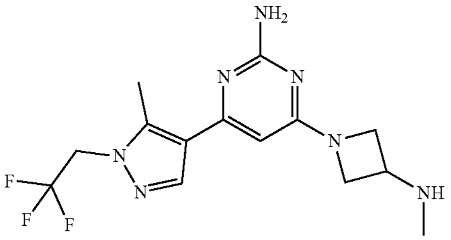
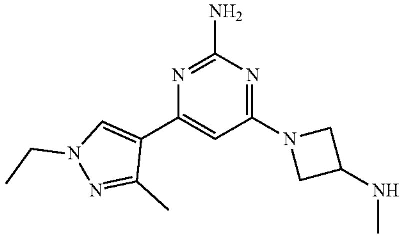
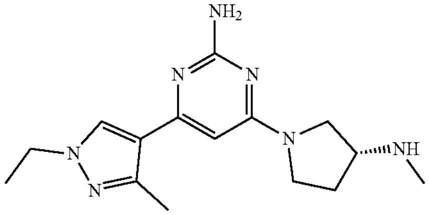
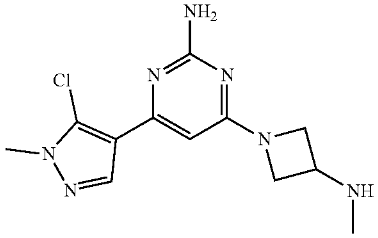
-continued
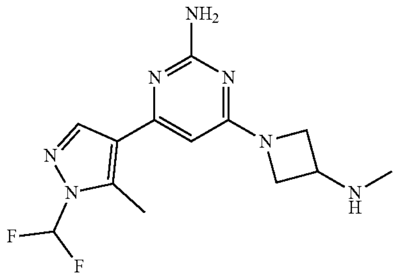
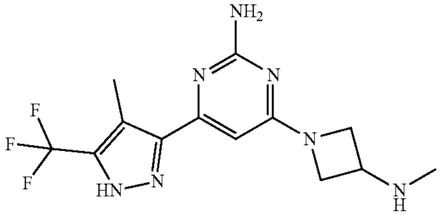
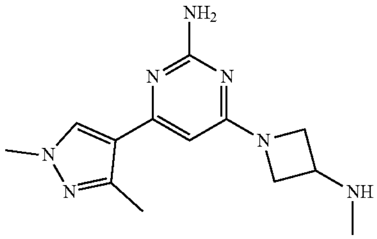
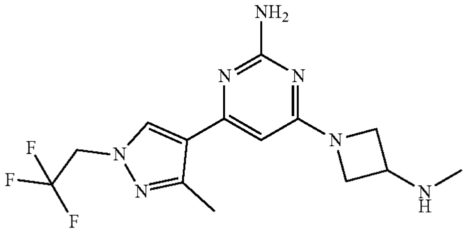
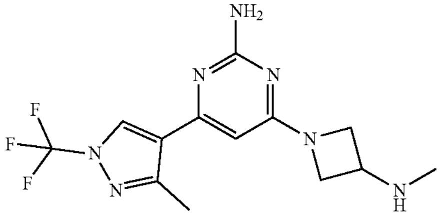
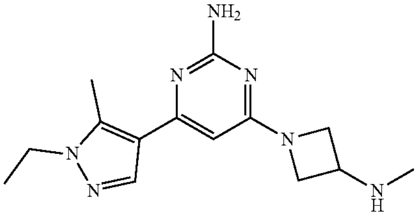
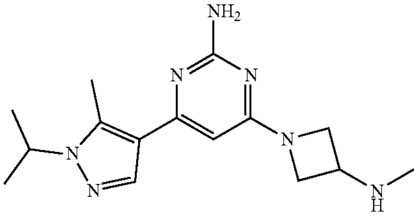

-continued
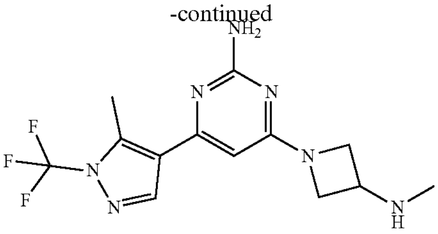
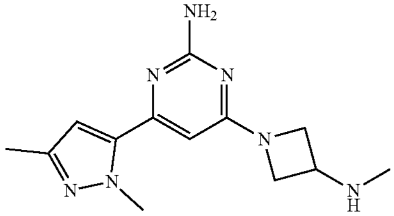
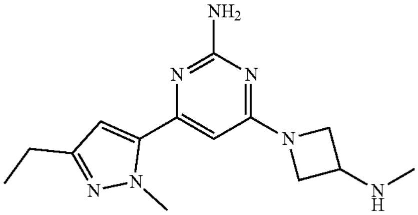
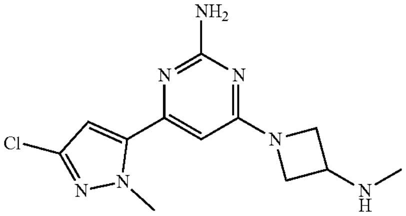
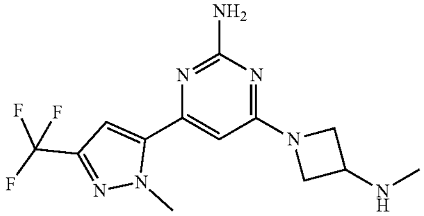
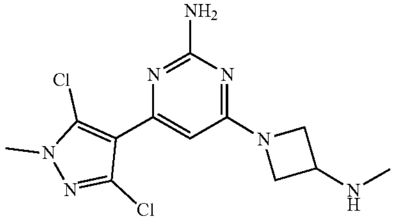
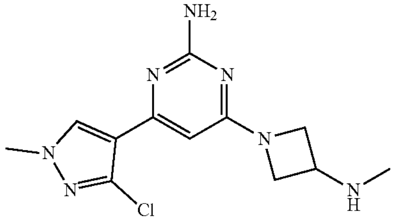
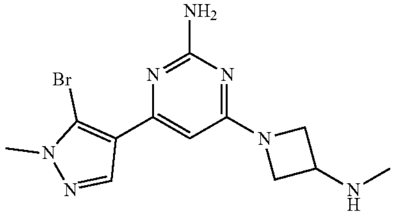
-continued
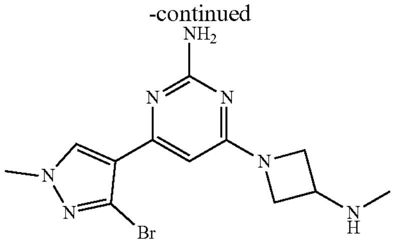
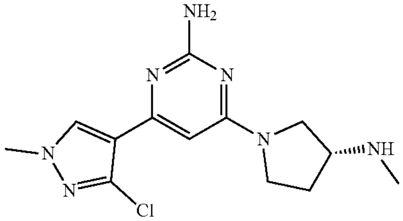
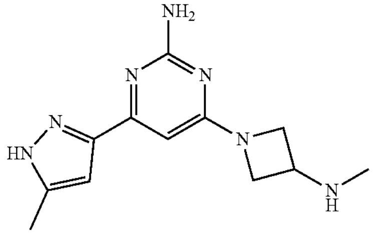
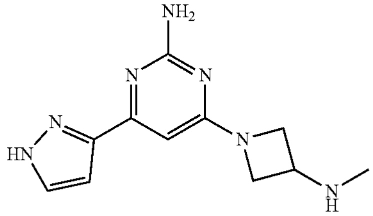
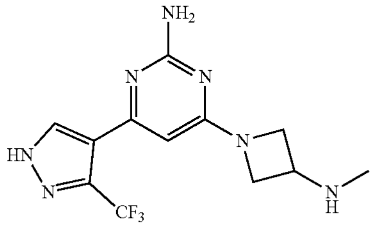
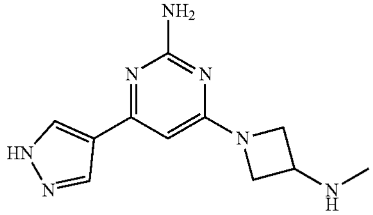
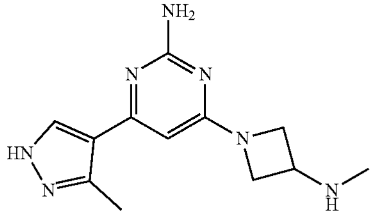

-continued

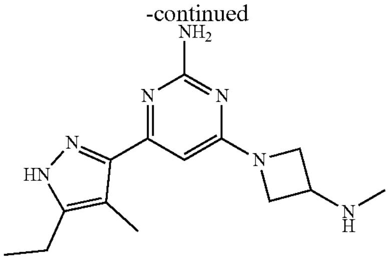

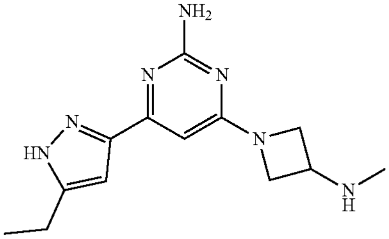

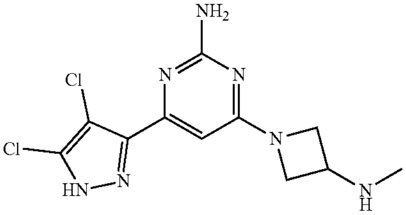

or a salt thereof.

The compound can be selected from the group consisting of:

4-(1-(Difluoromethyl)-1H-pyrazol-4-yl)-6-(3-(methylamino)azetidin-1-yl)pyrimidin-2-amine;

4-(3-(Methylamino)azetidin-1-yl)-6-(1-(2,2,2-trifluoroethyl)-1H-pyrazol-4-yl)pyrimidin-2-amine;

4-(1-Ethyl-1H-pyrazol-4-yl)-6-(3-(methylamino)azetidin-1-yl)pyrimidin-2-amine;

4-(Difluoromethyl)-3-methyl-1H-pyrazol-4-yl)-6-(3-(methylam ino)azetidin-1-yl)pyrimidin-2-amine;

(R)-4-(5-Chloro-1-methyl-1H-pyrazol-4-yl)-6-(3-(methylamino)pyrrolidin-1-yl)pyrimidin-2-amine;

4-(3-Aminoazetidin-1-yl)-6-(1-(trifluoromethyl)-1H-pyrazol-4-yl)pyrimidin-2-amine;

4-(3-(Ethylamino)azetidin-1-yl)-6-(1-(trifluoromethyl)-1H-pyrazol-4-yl)pyrimidin-2-amine;

4-(1,4-Dimethyl-1H-pyrazol-3-yl)-6-(3-(methylamino)azetidin-1-yl)pyrimidin-2-amine;

4-(1-(2,2-Difluoroethyl)-1H-pyrazol-4-yl)-6-(3-(methylamino)azetidin-1-yl)pyrimidin-2-amine;

4(1-(2-Fluoroethyl)-1H-pyrazol-4-yl)-6-(3-(methylamino)azetidin-1-yl)pyrimidin-2-amine;

4-(1-Isopropyl-3-methyl-1H-pyrazol-4-yl)-6-(3-(methylamino)azetidin-1-yl)pyrimidin-2-amine;

4-(5-Methyl-1-(2,2,2-trifluoroethyl)-1H-pyrazol-4-yl)-6-(3-(methylamino)azetidin-1-yl)pyrimidin-2-amine;

4-(1-Ethyl-3-methyl-1H-pyrazol-4-yl)-6-(3-(methylamino)azetidin-1-yl)pyrim idin-2-amine;

(R)-4-(1-Ethyl-3-methyl-1H-pyrazol-4-yl)-6-(3-(methylamino)pyrrolidin-1-yl)pyrimidin-2-amine;

4-(5-Chloro-1-methyl-1H-pyrazol-4-yl)-6-(3-(methylamino)azetidin-1-yl)pyrimi -yl)pyrimidin-2-amine;

4-(4-Methyl-5-(trifluoromethyl)-1H-pyrazol-3-yl)-6-(3-(methylamino)azetidin-1-yl)pyrimidin-2-amine;

4-(1,3-Dimethyl-1H-pyrazol-4-yl)-6-(3-(methylamino)azetidin-1-yl)pyrimidin-2-amine;

4(3-Methyl-1-(2,2,2-trifluoroethyl)-1H-pyrazol-4-yl)-6-(3-(methylamino)azetidin-1-yl)pyrim idin-2-amine;

4-(3-Methyl-1-(trifluoromethyl)-1H-pyrazol-4-yl)-6-(3-(methylamino)azetidin-1-yl)pyrimidin-2-amine;

4-(1-Ethyl-5-methyl-1H-pyrazol-4-yl)-6-(3-(methylamino)azetidin-1-yl)pyrim idin-2-amine;

4-(1-Isopropyl-5-methyl-1H-pyrazol-4-yl)-6-(3-(methylamino)azetidin-1-yl)pyrimidin-2-amine;

4(5-Methyl-1-(trifluoromethyl)-1H-pyrazol-4-yl)-6-(3-(methylamino)azetidin-1-yl)pyrimidin-2-amine;

4-(1,3-Dimethyl-1H-pyrazol-5-yl)-6-(3-(methylamino)azetidin-1-yl)pyrimidin-2-amine;

4-(3-Ethyl-1-methyl-1H-pyrazol-5-yl)-6-(3-(methylamino)azetidin-1-yl)pyrimidin-2-amine;

4-(3-Chloro-1-methyl-1H-pyrazol-5-yl)-6-(3-(methylam ino)azetidin-1-yl)pyrimidin-2-amine;

4-(1-Methyl-3-(trifluoromethyl)-1H-pyrazol-5-yl)-6-(3-(methylamino)azetidin-1-yl)pyrimidin-2-amine;

4-(3,5-Dichloro-1-methyl-1H-pyrazol-4-yl)-6-(3-(methylamino)azetidin-1-yl)pyrimidin-2-amine;

4-(3-Chloro-1-methyl-1H-pyrazol-4-yl)-6-(3-(methylamino)azetidin-1-yl)pyrimidin-2-amine;

4-(5-Bromo-1-methyl-1H-pyrazol-4-yl)-6-(3-(methylamino)azetidin-1-yl)pyrim din-2-amine;

4-(3-Bromo-1-methyl-1H-pyrazol-4-yl)-6-(3-(methylam no)azetidin-1-yl)pyrimidin-2-amine;

4-(3-(Methylamino)azetidin-1-yl)-6-(1-(trifluoromethyl)-1H-pyrazol-4-yl)pyridin-2-amine;

(R)-4-(3-(Methylamino)pyrrolidin-1-yl)-6-(1-(trifluoromethyl)-1H-pyrazol-4-yl)pyridin-2-amine;

(R)-4-(3-Chloro-1-methyl-1H-pyrazol-4-yl)-6-(3-(methylamino)pyrrolidin-1-yl)pyrimidin-2-amine;

4-(5-Methyl-1H-pyrazol-3-yl)-6-(3-(methylamino)azetidin-1-yl)pyrimidin-2-amine;

4-(3-(Methylamino)azetidin-1-yl)-6-(1H-pyrazol-3-yl)pyrimidin-2-amine;

4-(3-(Methylamino)azetidin-1-yl)-6-(3-(trifluoromethyl)-1H-pyrazol-4-yl)pyrim idin-2-amine;

4-(3-(Methylamino)azetidin-1-yl)-6-(1H-pyrazol-4-yl)pyrimidin-2-amine;

4-(3-Methyl-1H-pyrazol-4-yl)-6-(3-(methylamino)azetidin-1-yl)pyrimidin-2-amine;

4-(5-Ethyl-4-methyl-1H-pyrazol-3-yl)-6-(3-(methylamino)azetidin-1-yl)pyrimidin-2-amine;

4-(5-Ethyl-1H-pyrazol-3-yl)-6-(3-(methylamino)azetidin-1-yl)pyrimidin-2-amine;

4-(4,5-Dichloro-1H-pyrazol-3-yl)-6-(3-(methylamino)azetidin-1-yl)pyrimidin-2-amine;

or a salt thereof.

The compound can be a compound selected from the group consisting of:

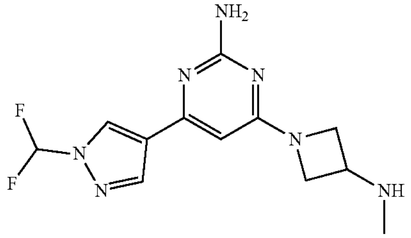

-continued
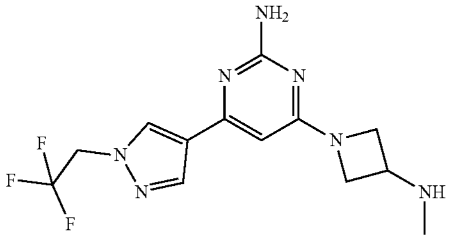
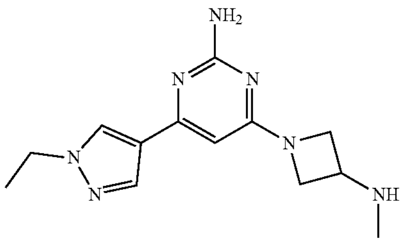
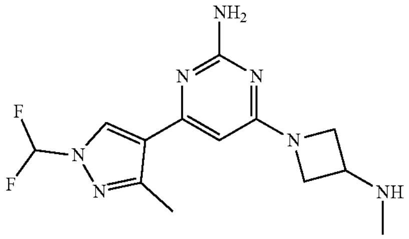
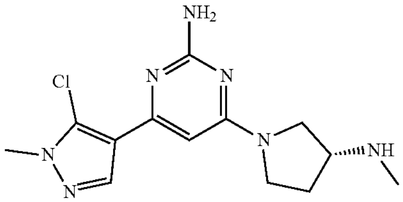
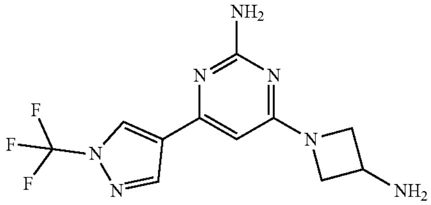
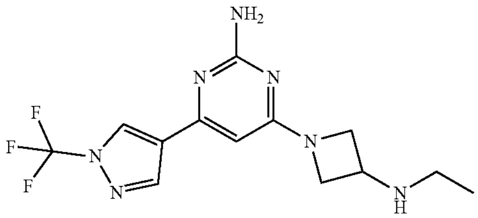
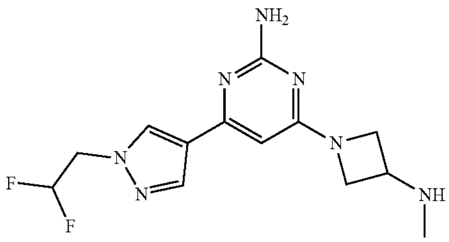
-continued
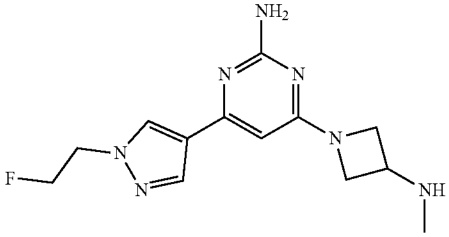
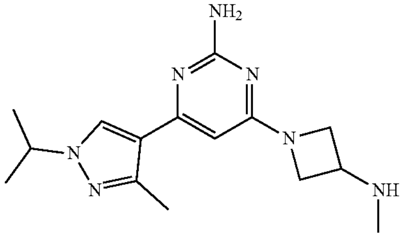
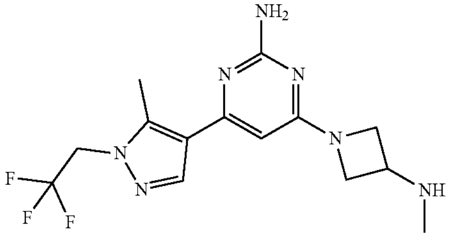
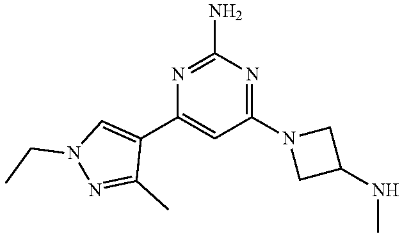
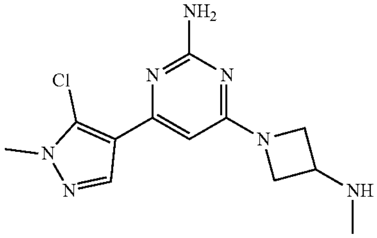
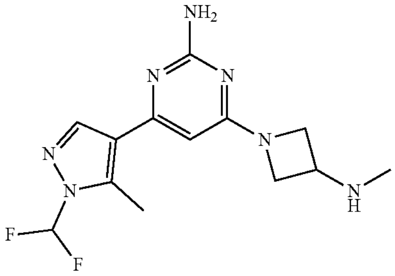
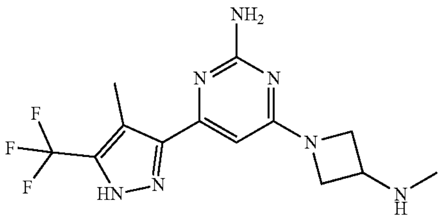

-continued
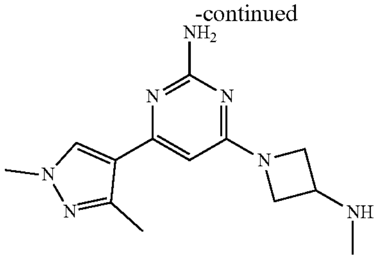
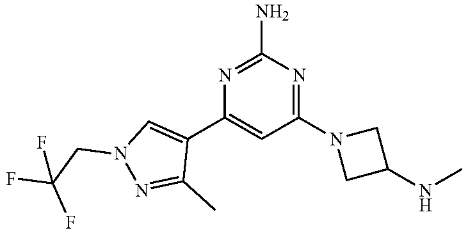
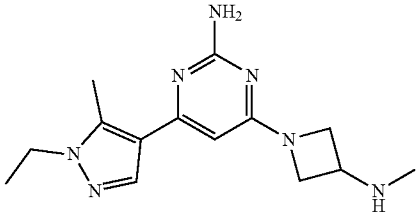
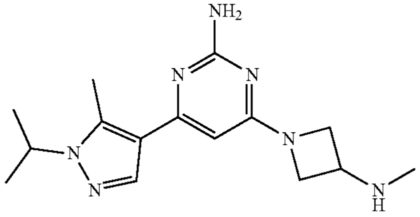
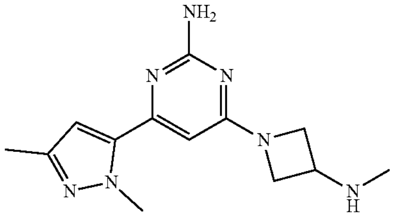
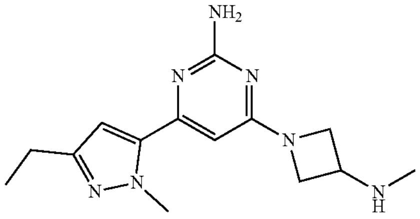
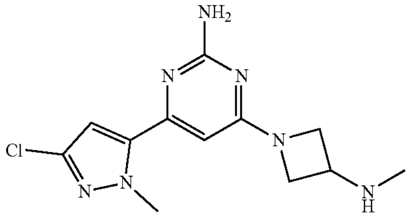
-continued
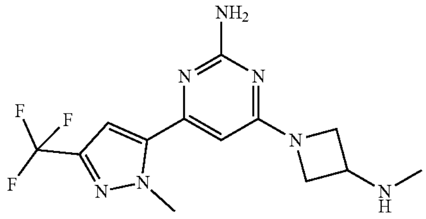
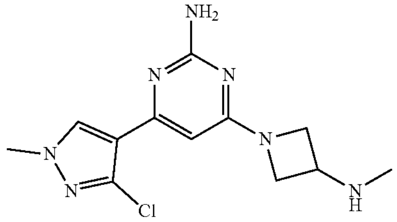
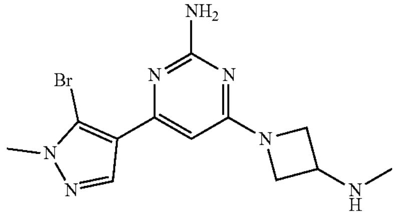
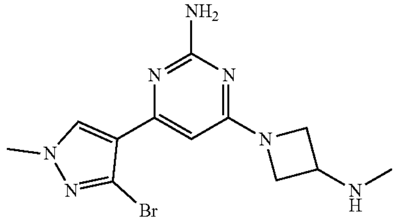
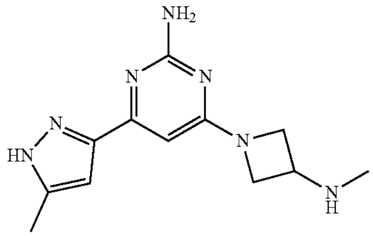
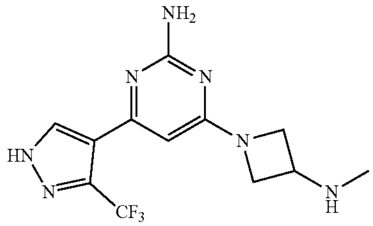
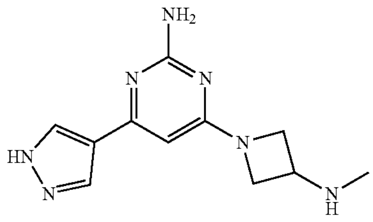

-continued

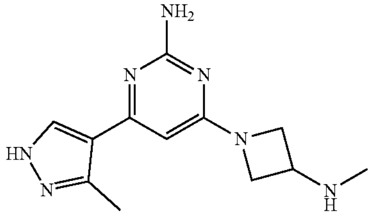

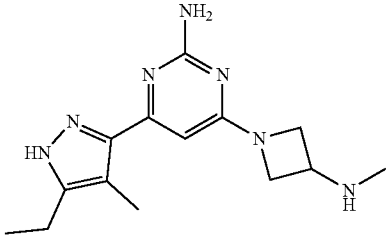

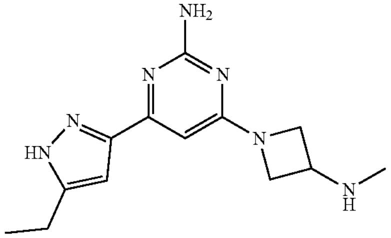

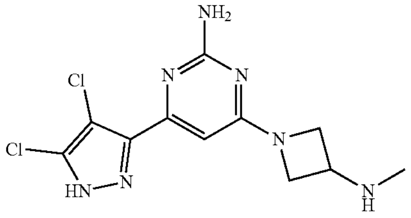

or a salt thereof.

The compound can be a compound selected from the group consisting of:

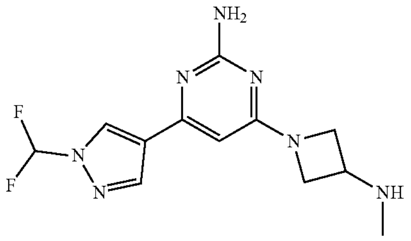

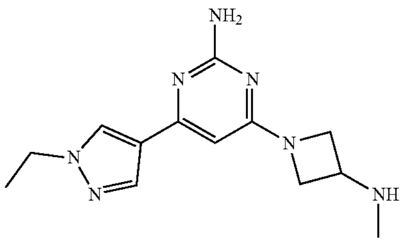

-continued

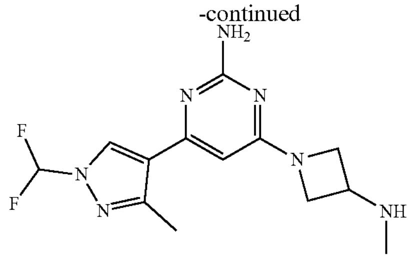

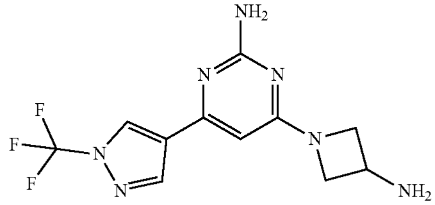

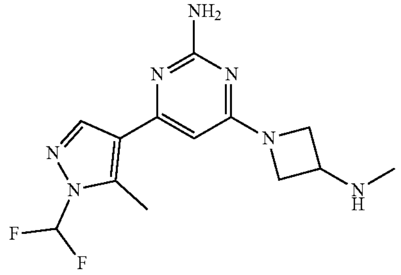

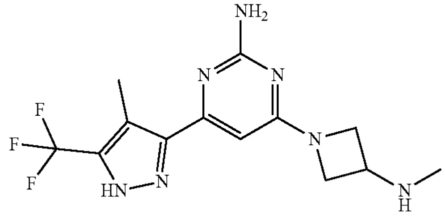

or a salt thereof.

Specific examples of compounds include those having low hERG activity. The compounds of the invention exhibit low hERG activity which is particularly beneficial for the reasons outlined in the background section above. Compounds exhibiting low hERG activity herein in particular are those with a hERG $pIC_{50}$ of 4.5 and below.

Definitions

In this application, the following definitions apply, unless indicated otherwise.

The term "treatment", in relation to the uses of any of the compounds described herein, is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (+)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g.(+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, Ind., USA, 1999, ISBN 0-967- 06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Methods for the Preparation of Compounds of the Invention

Provided is a process for the preparation of a compound as defined above comprising:

(A) the reaction of a compound of the formula (10):

(10)

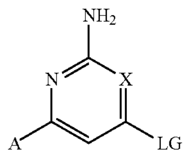

with a compound of the formula (11):

(11)

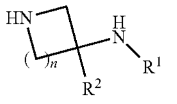

under SNAr conditions or transition metal catalyzed coupling conditions; wherein A is an optionally substituted pyrazole ring; $R^1$ is H, methyl or ethyl; $R^2$ is H; X is N or CH; n is 1 or 2; and LG represents a suitable leaving group; or (B) the reaction of a compound of the formula (12):

(12)

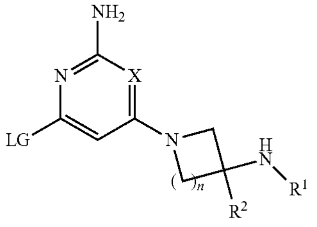

with a compound of the formula (13):

A-M (13)

under transition metal catalyzed coupling conditions or under SNAr conditions; wherein A, $R^1$, $R^2$, X and n are as defined above, LG represents a suitable leaving group and M, which may be present or absent, represents a suitably substituted metal or non-metal; or In process variant (A), the compound of formula (10) may be reacted with the compound of formula (11) under SNAr conditions. The SNAr reaction is typically carried out using either an excess of the compound of formula (11), or a stoichiometric quantity of the compound of formula (11) in the presence of a base which may be a tertiary amine base such as TEA or DIPEA or an inorganic base such as $K_2CO_3$, $Cs_2CO_3$ or $NaHCO_3$, optionally in a suitable solvent such as $H_2O$, MeCN, 1,4-dioxane, THF, MeOH, EtOH, IPA, BuOH, DMF, NMP or DMSO, or a combination of suitable solvents, at a temperature between about room temperature to about 200 °C, using conventional heating or optionally by heating with microwave irradiation, in an open vessel or optionally in a sealed vessel, optionally at a pressure greater than atmospheric pressure, optionally in the presence of an additive such as KF or a silver salt. Optionally, the compound of formula (11) may be present in the reaction as an acid salt such as an HCl, HBr or a TFA salt optionally in the presence of a tertiary base such as TEA or DIPEA. The leaving group LG in the compound of formula (10) may be a halogen such as F, Cl or Br; an alkoxy group such as OMe; an aryloxy group such as pentafluorophenoxy; a sulfenyl group such as SMe, a sulfinyl group such as SOMe, a sulfonyl group such as $SO_2Me$, a sulfonyloxy group such as OTs, OMs, ONs or OTf; or a leaving group generated by reaction of a hydroxy group with a peptide coupling reagent such as BOP, PyBOP or HATU.

Alternatively, in process variant (A), the compound of formula (10) may be reacted with the compound of formula (11) under transition metal catalyzed coupling conditions. The transition metal catalyzed coupling reaction is typically carried out using the compound of formula (11) in the presence of an inorganic base such as NaO$^t$Bu, KO$^t$Bu, $K_3PO_4$, $K_2CO_3$ or $Cs_2CO_3$, in a suitable solvent such as 1,4-dioxane, THF, DME or toluene, or a combination of suitable solvents, in the presence of a sub-stoichiometric quantity of a transition metal catalyst such as $Pd(OAc)_2$, $Pd_2(dba)_3$, $Pd(dppf)Cl_2$, $Pd(PPh_3)_2Cl_2$ or $Pd(PPh_3)_4$, optionally in the presence of a sub-stoichiometric quantity of a phosphine ligand such as $PPh_3$, $PBu_3$, $P^tBu_3$, XPhos, Xantphos or BINAP, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (10) may be a halogen such as Cl, Br or I, or a sulfonyloxy group such as OTs, OMs, ONs or OTf.

Compounds of formula (10) can be prepared by the reaction shown in Scheme 1 below:

Scheme 1

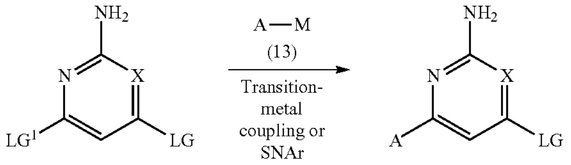

(14) (10)

Thus, a compound of formula (14), wherein X is as defined above, and LG and $LG^1$ may be the same or different and represent suitable leaving groups, may be reacted with a compound of formula (13), wherein A is as defined in above, and M, which may be present or absent, represents a suitably substituted metal or non-metal, under transition metal catalyzed coupling conditions or under SNAr conditions to form a compound of formula (10). The transition metal catalyzed coupling reaction or the SNAr reaction is typically carried as described below in process variant (B), and the compounds of formula (13) and formula (14) may be commercially available or easily prepared by standard methods reported in the published literature from simple starting materials known to the skilled person. Occasionally, due to their instability, it may be necessary to generate compounds of formula (13), where M is present, in-situ at low temperatures, e.g. between about −78 °C and room temperature, and react them further in a transition metal catalyzed coupling reaction, without their prior isolation. Details of such methods are known in the published literature, e.g. as reported by Oberli and Buchwald in Org. Lett., 2012, Vol. 14, No. 17, p 4606.

Alternatively, compounds of formula (10), wherein X represents N and LG represents Cl, can be typically prepared by the sequence of reactions shown in Scheme 2 below:

Scheme 2

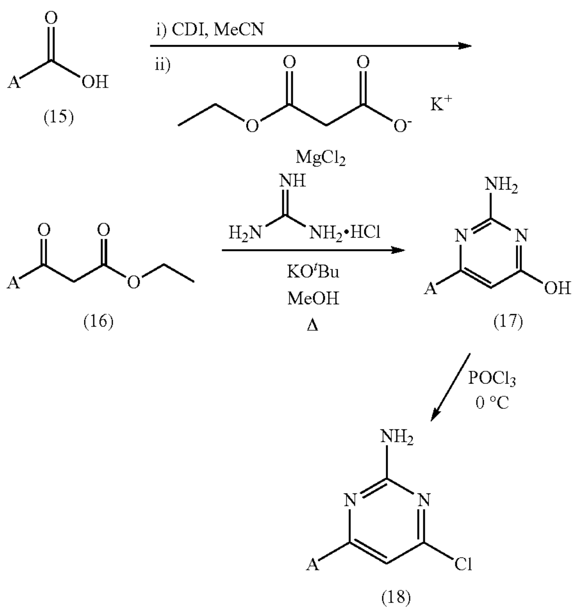

(15) (16) (17) (18)

Thus, a carboxylic acid of formula (15) may be homologated to the corresponding beta-keto ester (16) by first activating it via a number of standard methods known to the skilled person, e.g. by reaction with CDI in a suitable solvent such as MeCN, and then reacting with a malonic acid derivative such as potassium 3-ethoxy oxopropanoate in the presence of a Lewis acid such as $MgCl_2$. Once formed, the beta-keto ester (16) may be cyclised to the amino-hydroxypyrimidine analogue (17) by reaction with guanidine, or an appropriate guanidine salt, in the presence of a suitable base such as $KO^tBu$ in a suitable solvent such as MeOH. The amino-hydroxypyrimidine analogue (17) so formed may then be reacted with $POCl_3$ in the presence or absence of a suitable solvent to form a compound of formula (18). Compounds of formula (15) may be commercially available or easily prepared by standard methods reported in the published literature from simple starting materials known to the skilled person.

Compounds of formula (11) may be commercially available or easily prepared by standard methods reported in the published literature from simple starting materials known to the skilled person.

In process variant (B), the compound of formula (12) may be reacted with the compound of formula (13) under transition metal catalyzed coupling conditions. The transition metal catalyzed coupling reaction is typically carried out using the compound of formula (13) wherein M is present. For example, when M represents a boronic acid —$B(OH)_2$, or a boronic ester such as —$B(OMe)_2$, —$B(OiPr)_2$ or Bpin, or a lithium trialkylborate such as —$B(OiPr)_3Li$, then the transition metal catalyzed coupling reaction is typically carried out in the presence of an inorganic base such as $NaHCO_3$, $Na_2CO_3$, $K_2CO_3$, $Cs_2CO_3$ or $K_3PO_4$, in a suitable solvent such as $H_2O$, MeCN, 1,4-dioxane, THF, $Et_2O$, DME, EtOH, IPA, DMF, NMP or toluene, or a combination of suitable solvents, in the presence of a sub-stoichiometric quantity of a transition metal catalyst such as $Pd(OAc)_2$, $Pd_2(dba)_3$, $Pd(dppf)Cl_2$, $Pd(PPh_3)_2Cl_2$, $Pd(PPh_3)_4$, or a transition metal pre-catalyst such as XPhos Pd G2, optionally in the presence of a sub-stoichiometric quantity of a phosphine ligand such as $PPh_3$, $P^tBu_3$, $PCy_3$ or XPhos, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I, or a sulfonyloxy group such as OTs, OMs or OTf.

Alternatively, when M represents a trifluoroborate salt $BF_3^-$, then the transition metal catalyzed coupling reaction is typically carried out in the presence of an inorganic base such as $Na_2CO_3$, $K_2CO_3$, $Cs_2CO_3$ or $K_3PO_4$, in a suitable solvent such as $H_2O$, MeCN, 1,4-dioxane, THF, MeOH or EtOH, or a combination of suitable solvents, in the presence of a sub-stoichiometric quantity of a transition metal catalyst such as $Pd(OAc)_2$, $Pd_2(dba)_3$, optionally in the presence of a sub-stoichiometric quantity of a phosphine ligand such as $PPh_3$, $PCy_3$ or RuPhos at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M represents a trialkyltin group such as $SnMe_3$ or $SnBu_3$, then the transition metal catalyzed coupling reaction is typically carried out in a suitable solvent such 1,4-dioxane, THF, DMF, or toluene, or a combination of suitable solvents, in the presence of a sub-stoichiometric quantity of a transition metal catalyst such as $Pd(OAc)_2$, $Pd_2(dba)_3$, $Pd(PPh_3)_2Cl_2$ or $Pd(PPh_3)_4$, optionally in the presence of an inorganic base such as $K_2CO_3$ or CsF, optionally in the presence of an additive such as LiCl, CuI, $Bu_4NBr$ or $Et_4NCl$, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M is absent, then the transition metal catalyzed coupling reaction is typically carried out in the presence of an inorganic base such as NaOtBu, KOtBu, $K_3PO_4$, $K_2CO_3$ or $Cs_2CO_3$, in a suitable solvent such as 1,4-dioxane, THF, DME or toluene, or a combination of suitable solvents, in the presence of a sub-stoichiometric quantity of a transition metal catalyst such as $Pd(OAc)_2$, $Pd_2(dba)_3$, $Pd(dppf)Cl_2$, $Pd(PPh_3)_2Cl_2$ or $Pd(PPh_3)_4$, optionally in the presence of a sub-stoichiometric quantity of a phosphine ligand such as $PPh_3$, $PBu_3$, $PtBu_3$, XPhos, Xantphos or BINAP, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I, or a sulfonyloxy group such as OTs, OMs, ONs or OTf.

Alternatively, when M is absent, then the transition metal catalyzed coupling reaction is typically carried out in the presence of an inorganic base such as $K_3PO_4$, $K_2CO_3$ or $Cs_2CO_3$, in a suitable solvent such as 1,4-dioxane, DMF, DMSO or toluene, or a combination of suitable solvents, in the presence of a sub-stoichiometric quantity of a transition metal catalyst such as CuI, optionally in the presence of a sub-stoichiometric quantity of an amine such as (S)-proline or trans-$N^1$,$N^2$-dimethylcyclohexane-1,2-diamine at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M is absent, then the transition metal catalyzed coupling reaction is typically carried out in the presence of an organic base such as $nBu_4OAc$, in a suitable solvent such as 1,4-dioxane, in the presence of a sub-stoichiometric quantity of a transition metal pre-catalyst such as XPhos Pd G2, optionally in the presence of a sub-stoichiometric quantity of a phosphine ligand such as XPhos, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as Cl.

Alternatively, in process variant (B), the compound of formula (12) may be reacted with the compound of formula (13) under SNAr conditions. The SNAr reaction is typically carried out using the compound of formula (13) wherein M is absent, in the presence of a tertiary amine base such as TEA or DIPEA or an inorganic base such as $K_2CO_3$, $Cs_2CO_3$, KOtBu, or NaH in a suitable solvent such as THF, DMF, H2O, DMSO or NMP, or a combination of suitable solvents, at a temperature between about room temperature to about 200 °C, using conventional heating or optionally by heating with microwave irradiation, in an open vessel or optionally in a sealed vessel, optionally at a pressure greater than atmospheric pressure. The leaving group LG in the compound of formula (12) may be a halogen such as F, Cl or Br; an alkoxy group such as OMe; an aryloxy group such as pentafluorophenoxy; a sulfenyl group such as SMe, a sulfinyl group such as SOMe, a sulfonyl group such as $SO_2Me$, or a sulfonyloxy group such as OTs, OMs, ONs or OTf.

The compound of formula (12) can be prepared by the sequence of reactions shown in Scheme 3 below:

Scheme 3

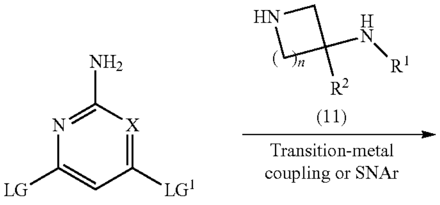

(14)

(11)

-continued

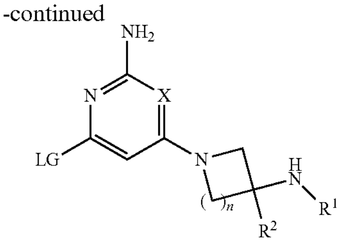

(12)

Thus, a compound of formula (14), wherein X is as defined above, and LG and $LG^1$ may be the same or different and represent suitable leaving groups, may be reacted with a compound of formula (11), wherein $R^1$, $R^2$ and n are as defined above, under SNAr conditions or under transition metal catalyzed coupling conditions to form a compound of formula (12). The SNAr reaction or the transition metal catalyzed coupling reaction is typically carried as described above in process variant (A).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis,* Fifth Edition, Editor: Peter G. M. Wuts, John Wiley, 2014, (ISBN: 9781118057483). In particular, a useful protecting group for manipulating compounds of formula (10) or formula (12) includes the 2,5-dimethyl-1H-pyrrole group; useful protecting groups for manipulating compounds of formula (11) or formula (12) include BOC and CBZ; and useful protecting groups for manipulating compounds of formula (13) include SEM and THP.

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, the invention provides a pharmaceutical composition comprising at least one compound of the invention as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of invention can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the following examples.

Examples 1 to 42

The compounds of Examples 1 to 42 shown in Table 1 below have been prepared. Their NMR and LCMS properties and the methods used to prepare them are set out in Table 3. The starting materials for each of the Examples are listed in Table 2. For Examples 20, 23, 32 and 33 proposed routes of synthesis are shown.

TABLE 1

| Example compounds | |
|---|---|
| 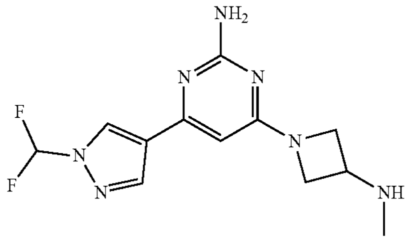 | Example 1 |

TABLE 1-continued
Example compounds
Example 2
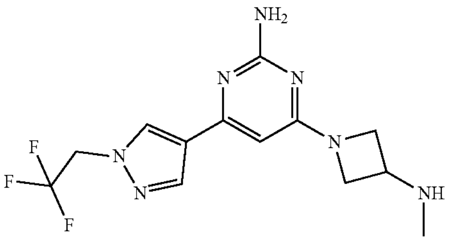
Example 3
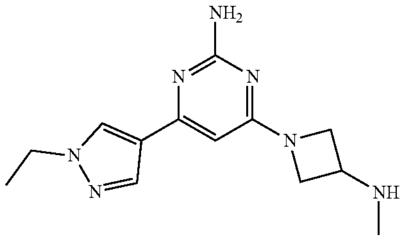
Example 4
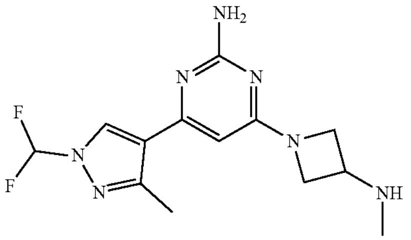
Example 5
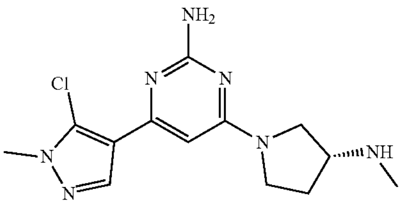
Example 6
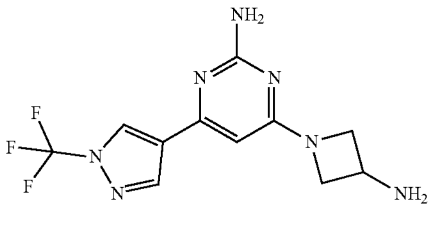
Example 7
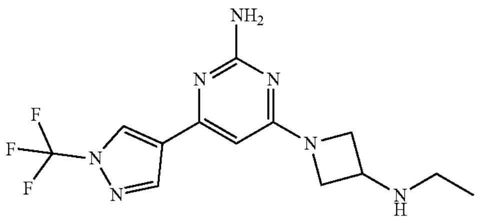
TABLE 1-continued
Example compounds
Example 8
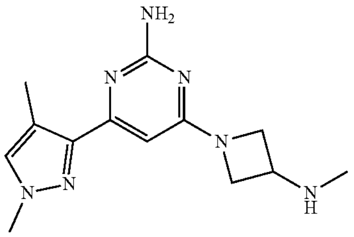
Example 9
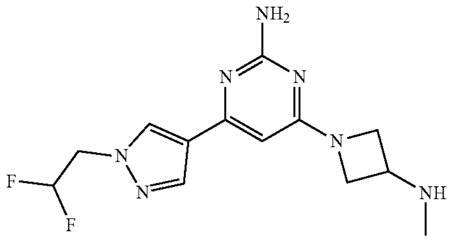
Example 10
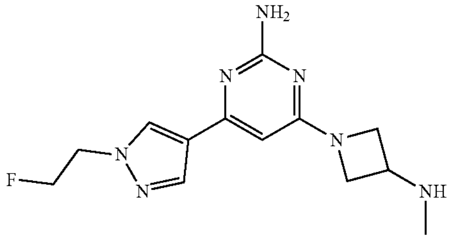
Example 11
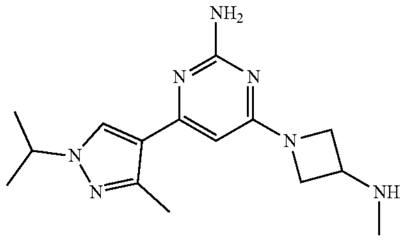
Example 12
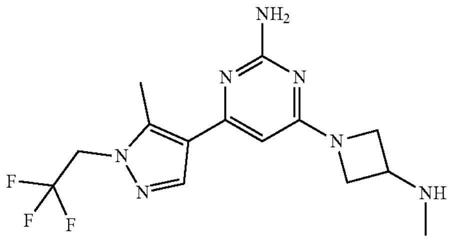
Example 13
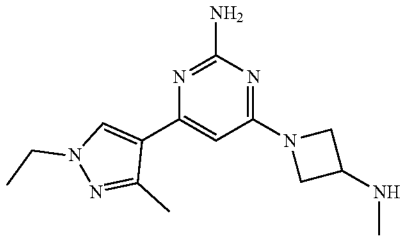

TABLE 1-continued
Example compounds
Example 14
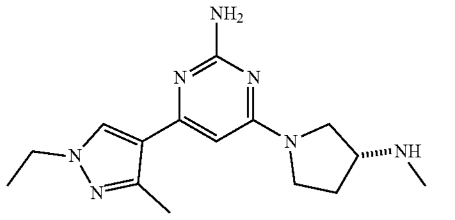
Example 15
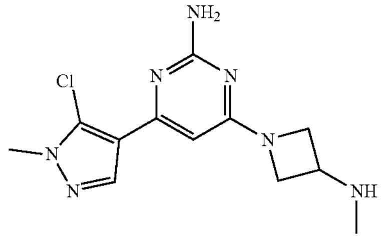
Example 16
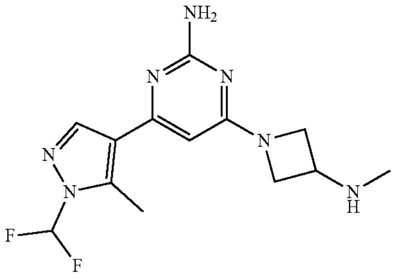 [SMILES: CNC1CN(c2cc(-c3cnn(C(F)F)c3C)nc(N)n2)C1]
Example 17
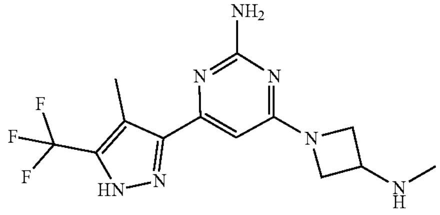 [SMILES: CNC1CN(c2cc(-c3n[nH]c(C(F)(F)F)c3C)nc(N)n2)C1]
Example 18
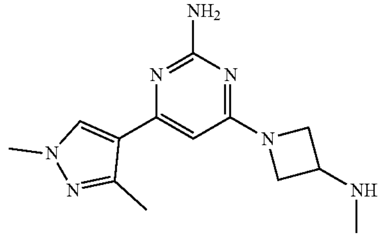 [SMILES: CNC1CN(c2cc(-c3cn(C)nc3C)nc(N)n2)C1]
Example 19
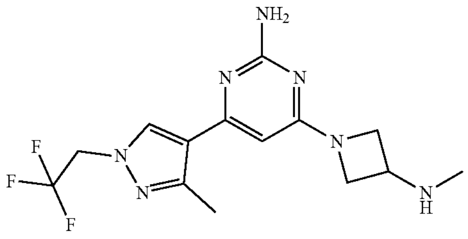 [SMILES: CNC1CN(c2cc(-c3cn(CC(F)(F)F)nc3C)nc(N)n2)C1]
TABLE 1-continued
Example compounds
Example 20
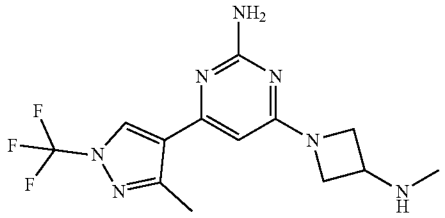 [SMILES: CNC1CN(c2cc(-c3cn(C(F)(F)F)nc3C)nc(N)n2)C1]
Example 21
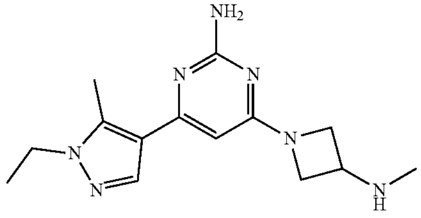 [SMILES: CCn1ncc(-c2cc(N3CC(NC)C3)nc(N)n2)c1C]
Example 22
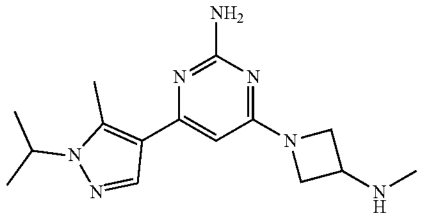 [SMILES: CNC1CN(c2cc(-c3cnn(C(C)C)c3C)nc(N)n2)C1]
Example 23
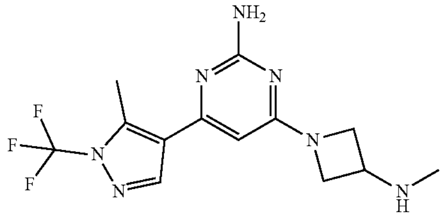 [SMILES: CNC1CN(c2cc(-c3cnn(C(F)(F)F)c3C)nc(N)n2)C1]
Example 24
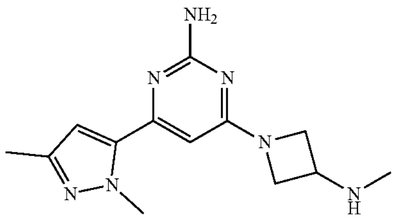
Example 25
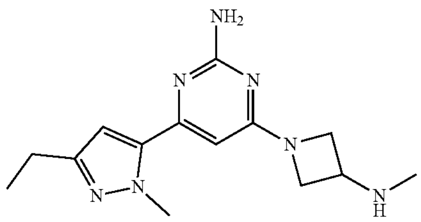 [SMILES: CCc1cc(-c2cc(N3CC(NC)C3)nc(N)n2)n(C)n1]
Example 26
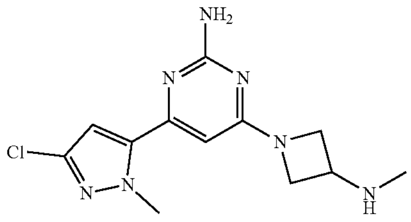 [SMILES: CNC1CN(c2cc(-c3cc(Cl)nn3C)nc(N)n2)C1]

TABLE 1-continued
| Example compounds | |
|---|---|
| 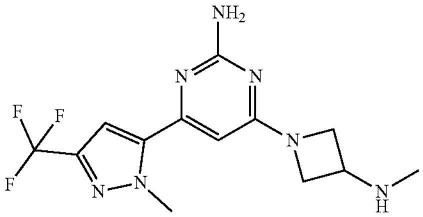 [SMILES: CNC1CN(c2cc(-c3cc(C(F)(F)F)nn3C)nc(N)n2)C1] | Example 27 |
| 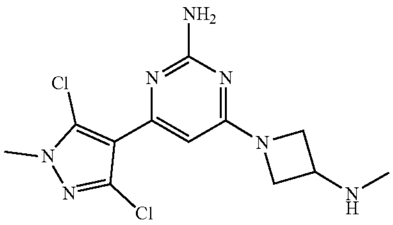 | Example 28 |
| 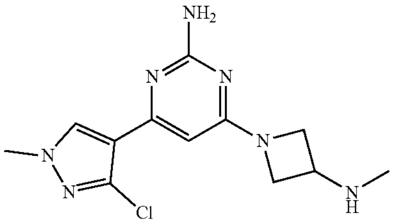 | Example 29 |
| 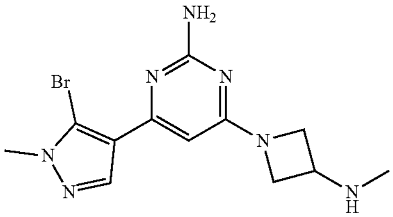 | Example 30 |
| 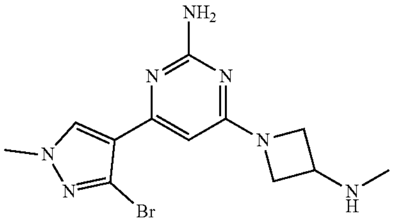 | Example 31 |
| 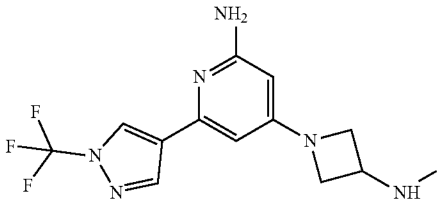 [SMILES: CNC1CN(c2cc(N)nc(-c3cnn(C(F)(F)F)c3)c2)C1] | Example 32 |
| 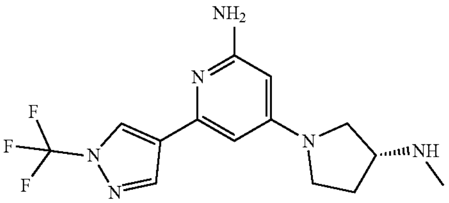 [SMILES: CN[C@@H]1CCN(c2cc(N)nc(-c3cnn(C(F)(F)F)c3)c2)C1] | Example 33 |
TABLE 1-continued
| Example compounds | |
|---|---|
| 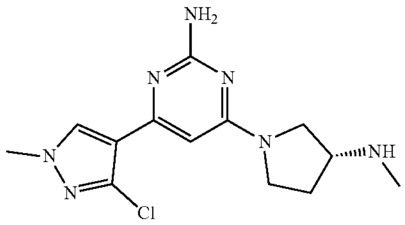 | Example 34 |
| 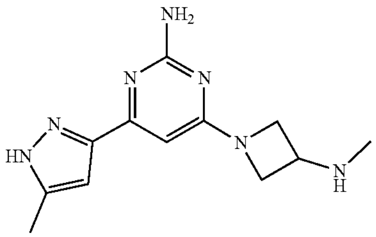 [SMILES: CNC1CN(c2cc(-c3cc(C)[nH]n3)nc(N)n2)C1] | Example 35 |
| 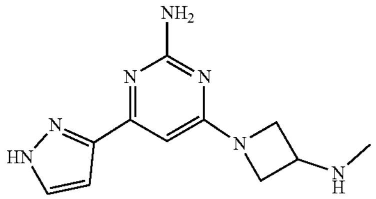 [SMILES: CNC1CN(c2cc(-c3cc[nH]n3)nc(N)n2)C1] | Example 36 |
| 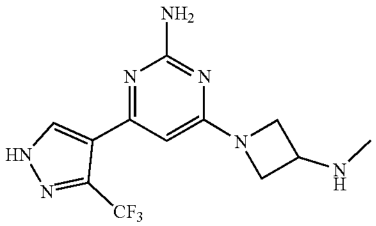 [SMILES: CNC1CN(c2cc(-c3c[nH]nc3C(F)(F)F)nc(N)n2)C1] | Example 37 |
| 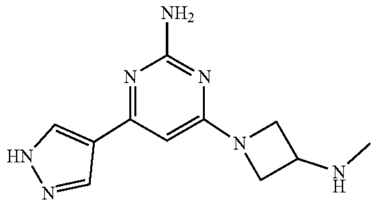 [SMILES: CNC1CN(c2cc(-c3cn[nH]c3)nc(N)n2)C1] | Example 38 |
| 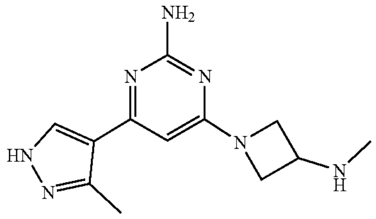 [SMILES: CNC1CN(c2cc(-c3c[nH]nc3C)nc(N)n2)C1] | Example 39 |
| 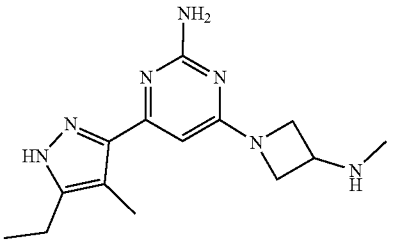 [SMILES: CCc1[nH]nc(-c2cc(N3CC(NC)C3)nc(N)n2)c1C] | Example 40 |

TABLE 1-continued

| Example compounds | |
|---|---|
| 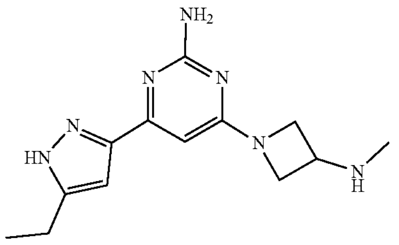 [SMILES: CCc1cc(-c2cc(N3CC(NC)C3)nc(N)n2)n[nH]1] | Example 41 |

TABLE 1-continued

| Example compounds | |
|---|---|
| 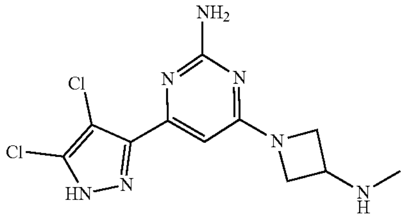 [SMILES: CNC1CN(c2cc(-c3n[nH]c(Cl)c3Cl)nc(N)n2)C1] | Example 42 |

General Procedures

Where no preparative routes are included, the relevant intermediate is commercially available. Commercial reagents were utilized without further purification. Room temperature (rt) refers to approximately 20-27 °C $^1$H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. Column chromatography performed using 'basic silica' refers to the use of Biotage® KP-NH silica gel. Column chromatography performed under reversed phase conditions using 'C18 silica' refers to the use of Biotage® KP-C18 silica gel. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below:

| System | Instrument Name | LC Detector | Mass Detector |
|---|---|---|---|
| 1 | Shimadzu Nexera | Photo Diode Array | LCMS-2020 |
| 2 | Agilent 1290 RRLC | Photo Diode Array | Agilent 6120 |

| Method Name | Solvent System | Column used | Gradient | UV Range | Mass Range | Column Temp. °C | Flow Rate mL/min |
|---|---|---|---|---|---|---|---|
| 1 | (A) 0.1% $NH_3$ in Water (B) 0.1% $NH_3$ in Acetonitrile | X-Bridge C18 50 × 4.6 mm, 3.5 µm or equivalent | 95:5 at 0.01 min, 10:90 at 5.0 min & 5:95 at 5.80 min till 7.20 min, 95:5 at 7.21 min up to 10.0 min | 200-400 nm | 60-1000 amu | Ambient | 1.00 |
| 2 | (A) 5 mM Ammonium Bicarbonate in Water (B) 100% Acetonitrile | X-Bridge C18 50 × 4.6 mm, 3.5 µm or equivalent | 95:5 at 0.01 min, 10:90 at 3.5 min & 5:95 at 4.5 min till 6.0 min, 95:5 at 6.01 min up to 8.0 min | 200-400 nm | 60-1000 amu | Ambient | 1.00 |

LCMS data in the experimental section and Tables 2 and 3 are given in the format: (Instrument system, Method): Mass ion, retention time, UV detection wavelength.

Compound Purification

Final purification of compounds was performed by preparative reversed phase HPLC using the instrument and methods detailed below where data is given in the following format: Purification technique: [phase (column description, column length×internal diameter, particle size), solvent flow-rate, gradient—given as % of mobile phase B in mobile phase A (over time), mobile phase (A), mobile phase (B)].

Preparative HPLC Purification:

Shimadzu LC-20AP binary system with SPD-20A UV detector Gilson semi preparative HPLC system with 321 pump, GX-271 liquid handler and Gilson 171 DAD controlled with Gilson Trilution software Purification Method A Prep HPLC: [Reversed Phase (Sunfire C-18, 250×19 mm, 5 µm), 12 mL/min, gradient 0%-30% (over 17 min), 100% (over 1 min), 100%-0% (over 4 min), mobile phase (A): 0.1% trifluoroacetic acid in water, (B): 100% acetonitrile].

Purification Method B

Prep HPLC: [Reversed Phase (Sunfire C-18, 250×19 mm, 5 µm), 12 mL/min, gradient 0%-15% (over 24 min), 15% -15% (over 3 min), 100% (over 2 min), 100%-0% (over 6 min), mobile phase (A): 0.1% trifluoroacetic acid in water, (B): 100% acetonitrile].

Purification Method C

Prep HPLC: [Reversed Phase (YMC-Actus Triart C-18, 250×20 mm, 5 µm), 16 mL/min, gradient 5%-15% (over 18 min), 15%-15% (over 2 min), 100% (over 2 min), 100%-0%

(over 5 min), mobile phase (A): 0.1% trifluoroacetic acid in water, (B): 100% acetonitrile].

Purification Method D

Prep HPLC: [Reversed Phase (X-select CSH Phenyl Hexyl C-18, 250×19 mm, 5 μm), 15 mL/min, gradient 3%-3% (over 40 min), mobile phase (A): 0.1% trifluoroacetic acid in water, (B): 100% aceton itrile].

Purification Method E

Prep HPLC: [Reversed Phase (Gemini-NX C-18, 150×21.2 mm, 5 μm), 16 mL/min, gradient 5%-30% (over 25 min), 100% (over 3 min), 100%-5% (over 4 min), mobile phase (A): 5 mM ammonium bicarbonate+0.1% ammonia in water, (B): 100% acetonitrile].

Purification Method F

Prep HPLC: [Reversed Phase (YMC-Actus Triart C-18, 250×20 mm, 5 μm), 13 mL/min, gradient 5%-20% (over 22 min), 20% -20% (over 3 min), 100% (over 2 min), 100%-5% (over 6 min), mobile phase (A): 0.1% trifluoroacetic acid in water, (B): 100% acetonitrile].

Purification Method G

Prep HPLC: [Reversed Phase (Sunfire C-18, 250×19 mm, 5 μm), 13 mL/min, gradient 0%-15% (over 24 min), 15%-15% (over 5 min), 100% (over 2 min), 100%-0% (over 5 min), mobile phase (A): 0.1% trifluoroacetic acid in water, (B): 100% acetonitrile].

Purification Method H

Prep HPLC: [Reversed Phase (Sunfire C-18, 250×19 mm, 5 μm), 15 mL/min, gradient 0%-30% (over 17 min), 100% (over 1 min), 100%-0% (over 4 min), mobile phase (A): 0.1% trifluoroacetic acid in water, (B): 100% acetonitrile].

Purification Method I

Prep HPLC: [Reversed Phase (YMC-Actus Triart C-18, 250×20 mm, 5 μm), 15 mL/min, gradient 0%-15% (over 25 min), 15% -15% (over 4 min), 100% (over 2 min), 100%-5% (over 5 min), mobile phase (A): 0.1% trifluoroacetic acid in water, (B): 100% acetonitrile].

Purification Method J

Prep HPLC: [Reversed Phase (YMC-Actus Triart C-18, 250×20 mm, 5 μm), 15 mL/min, gradient 5%-12% (over 28 min), 100% (over 2 min), 100%-5% (over 6 min), mobile phase (A): 0.1% trifluoroacetic acid in water, (B): 100% acetonitrile].

Purification Method K

Prep HPLC: [Reversed Phase (YMC-Actus Triart C-18, 250×20 mm, 5 μm), 15 mL/min, gradient 0%-15% (over 18 min), 15% -15% (over 5 min), 100% (over 2 min), 100%-0% (over 3 min), mobile phase (A): 0.1% trifluoroacetic acid in water, (B): 100% acetonitrile].

Purification Method L

Prep HPLC: [Reversed Phase (X-select CSH Phenyl Hexyl C-18, 250×19 mm, 5 μm), 15 mL/min, gradient 0%-20% (over 23 min), 100% (over 2 min), 100%-0% (over 3 min), mobile phase (A): 0.1% trifluoroacetic acid in water, (B): 100% acetonitrile].

Purification Method M

Prep HPLC: [Reversed Phase (Sunfire C-18, 250×18 mm, 5 μm), 14 mL/min, gradient 0%-20% (over 22 min), 100% (over 2 min), 100%-0% (over 6 min), mobile phase (A): 0.1% trifluoroacetic acid in water, (B): 100% acetonitrile].

Purification Method N

Prep HPLC: [Reversed Phase (Sunfire C-18, 250×18 mm, 5 μm), 15 mL/min, gradient 0%-20% (over 22 min), 100% (over 2 min), 100%-0% (over 2 min), mobile phase (A): 0.1% trifluoroacetic acid in water, (B): 100% acetonitrile].

Purification Method O

Prep HPLC: [Reversed Phase (X-select CSH Phenyl Hexyl C-18, 250×19 mm, 5 μm), 15 mL/min, gradient 0%×5% (over 22 min), 5%-5% (over 2 min), 100% (over 2 min), 100%-0% (over 5 min), mobile phase (A): 0.1% trifluoroacetic acid in water, (B): 100% acetonitrile].

Purification Method P

Prep HPLC: [Reversed Phase (Sunfire C-18, 250×19 mm, 5 μm), 13 mL/min, gradient 10%-15% (over 24 min), 100% (over 2 min), 100%-0% (over 6 min), mobile phase (A): 0.1% trifluoroacetic acid in water, (B): 100% acetonitrile].

Purification Method Q

Prep HPLC: [Reversed Phase (Sunfire C-18, 250×20 mm, 5 μm), 15 mL/min, gradient 0%-30% (over 17 min), 100% (over 1 min), 100%-0% (over 4 min), mobile phase (A): 0.1% trifluoroacetic acid in water, (B): 100% acetonitrile].

Purification Method R

Prep HPLC: [Reversed Phase (X-Bridge C-18, 250×19 mm, 5 μm), 14 mL/min, gradient 10%-30% (over 20 min), 30%-30% (over 2 min), 100% (over 2 min), 100%-10% (over 6 min), mobile phase (A): 5 mM ammonium bicarbonate+0.1% ammonia in water, (B): 100% acetonitrile].

Purification Method S

Prep HPLC: [Reversed Phase (Sunfire C-18, 250×19 mm, 5 μm), 15 mL/min, gradient 0%-20% (over 20 min), 100% (over 2 min), 100%-0% (over 6 min), mobile phase (A): 0.1% trifluoroacetic acid in water, (B): 100% acetonitrile].

Purification Method T

Prep HPLC: [Reversed Phase (Sunfire C-18, 250×19 mm, 5 μm), 15 mL/min, gradient 5%-20% (over 20 min), 100% (over 2 min), 100%-0% (over 5 min), mobile phase (A): 0.1% trifluoroacetic acid in water, (B): 100% acetonitrile].

Purification Method U

Prep HPLC: [Reversed Phase (YMC-Actus Triart C-18, 250×20 mm, 5 μm), 12 mL/min, gradient 0%-20% (over 25 min), 100% (over 2 min), 100%-0% (over 5 min), mobile phase (A): 0.1% trifluoroacetic acid in water, (B): 100% acetonitrile].

Purification Method V

Prep HPLC: [Reversed Phase (Gemini NX C-18, 150×21.2 mm, 5 μm), 15 mL/min, gradient 0%-15% (over 18 min), 100% (over 2 min), 100%-0% (over 5 min), mobile phase (A): 0.1% trifluoroacetic acid in water, (B): 100% acetonitrile].

Purification Method W

Prep HPLC: [Reversed Phase (Gemini NX C-18, 150×21.2 mm, 5 μm), 16 mL/min, gradient 0%-8% (over 18 min), 100% (over 2 min), 100%-0% (over 5 min), mobile phase (A): 0.1% trifluoroacetic acid in water, (B): 100% acetonitrile].

Purification Method X

Prep HPLC: [Reversed Phase (X-select CSH Phenyl Hexyl C-18, 250×19 mm, 5 μm), 14 mL/min, gradient 0%-20% (over 20 min), 100% (over 3 min), 100%-0% (over 5 min), mobile phase (A): 0.1% trifluoroacetic acid in water, (B): 100% acetonitrile].

Purification Method Y

Prep HPLC: [Reversed Phase (Sunfire C-18, 250×19 mm, 5 μm), 14 mL min, gradient 0%-15% (over 20 min), 15%-15% (over 2 min), 100% (over 2 min), 100%-0% (over 6 min), mobile phase (A): 0.1% trifluoroacetic acid in water, (B): 100% acetonitrile].

Purification Method Z

Prep HPLC: [Reversed Phase (Sunfire C-18, 250×19 mm, 5 μm), 14 mL/min, gradient 0%-15% (over 20 min), 100% (over 2 min), 100%-0% (over 6 min), mobile phase (A): 0.1% trifluoroacetic acid in water, (B): 100% acetonitrile].

Purification Method AA

Prep HPLC: [Reversed Phase (Sunfire C-18, 250×19 mm, 5 μm), 15 mL/min, gradient 0%-10% (over 25 min), 10% -

10% (over 2 min), 100 % (over 3 min), 100%-0% (over 5 min), mobile phase (A): 0.1% trifluoroacetic acid in water, (B): 100% acetonitrile].

Purification Method AB

Prep HPLC: [Reversed Phase (X-Bridge C-18, 250×19 mm, 5 μm), 15 mL/min, gradient 5%-27% (over 26 min), 100% (over 3 min), 100%-5% (over 5 min), mobile phase (A): 5 mM ammonium bicarbonate +0.1% ammonia in water, (B): 100% acetonitrile].

Purification Method AC

Prep HPLC: [Reversed Phase (Sunfire C-18, 250×20 mm, 5 μm), 15 mL/min, gradient 0%-30% (over 17 min), 100% (over 1 min), 100%-0% (over 4 min), mobile phase (A): 0.1% trifluoroacetic acid in water, (B): 100% acetonitrile].

Purification Method AD

Prep HPLC: [Reversed Phase (Sunfire C-18, 250×19 mm, 5 μm), 15 mL/min, gradient 0%-10% (over 18 min), 10%-10% (over 2 min), 100% (over 2 min), 100%-0% (over 6 min), mobile phase (A): 0.1% trifluoroacetic acid in water, (B): 100% acetonitrile].

Purification Method AE

Prep HPLC: [Reversed Phase (Sunfire C-18, 150×19 mm, 5 μm), 15 mL/min, gradient 0%-10% (over 12 min), 100% (over 2 min), 100%-0% (over 2 min), mobile phase (A): 0.1% formic acid in water, (B): 100% acetonitrile].

Purification Method AF

Prep HPLC: [Reversed Phase (X-Bridge C-18, 250×19 mm, 5 μm), 15 mL/min, gradient 0%-12% (over 25 min), 100% (over 2 min), 100%-0% (over 8 min), mobile phase (A): 5 mM ammonium bicarbonate+0.1% ammonia in water, (B): 100% acetonitrile].

Purification Method AG

Prep HPLC: [Reversed Phase (Sunfire C-18, 250×19 mm, 5 μm), 15 mL/min, gradient 0%-15% (over 18 min), 100% (over 3 min), 100%-0% (over 6 min), mobile phase (A): 0.1% trifluoroacetic acid in water, (B): 100% acetonitrile].

Purification Method AH

Prep HPLC: [Reversed Phase (X-Bridge C-18, 250×19 mm, 5 μm), 15 mL/min, gradient 0%-12% (over 20 min), 100% (over 2 min), 100%-0% (over 5 min), mobile phase (A): 0.1% trifluoroacetic acid in water, (B): 100% acetonitrile].

Purification Method AI

Prep HPLC: [Reversed Phase (Sunfire C-18, 250×19 mm, 5 μm), 17 mL/min, gradient 0%-20% (over 17 min), 100% (over 2 min), 100%-0% (over 4 min), mobile phase (A): 0.1% trifluoroacetic acid in water, (B): 100% acetonitrile].

Purification Method AJ

Prep HPLC: [Reversed Phase (X-Bridge C-18, 250×19 mm, 5 μm), 15 mL/min, gradient 0%-10% (over 28 min), 10% -10% (over 6 min), 100% (over 2 min), 100%-0% (over 6 min), mobile phase (A): 0.1% trifluoroacetic acid in water, (B): 100% acetonitrile].

Purification Method AK

Prep HPLC: [Reversed Phase (YMC-Actus Triart C-18, 250×20 mm, 5 μm), 16 mL/min, gradient 5%-20% (over 24 min), 100% (over 2 min), 100%-5% (over 6 min), mobile phase (A): 0.1% trifluoroacetic acid in water, (B): 100% acetonitrile].

ABBREVIATIONS

CDI=carbonyldiimidazole
DAST=diethylaminosulfur trifluoride
DCM=dichloromethane
DIPEA=N,N-diisopropylethylamine
ESI=electro spray ionisation
EtOAc=ethyl acetate
h=hour(s)
$H_2O$=water
HCl=hydrogen chloride, hydrochloric acid
HPLC=high performance liquid chromatography
IPA=propan-2-ol
LC=liquid chromatography
MeCN=acetonitrile
MeOH=methanol
min(s)=minute(s)
MS=mass spectrometry
nm=nanometre(s)
NMR=nuclear magnetic resonance
$POCl_3$=phosphorus oxychloride
RT=room temperature
sat.=saturated
SFC=supercritical fluid chromatography
TEA=triethylamine
TFA=trifluoroacetic acid
THF=tetrahydrofuran
TLC=thin layer chromatography

Synthesis of Intermediates

Route 1

Typical procedure for the preparation of pyrimidines, as exemplified by the preparation of Intermediate 3, tert-butyl (1-(2-amino-6-chloropyrimidin-4-yl) azetidin-3-yl) (methyl) carbamate

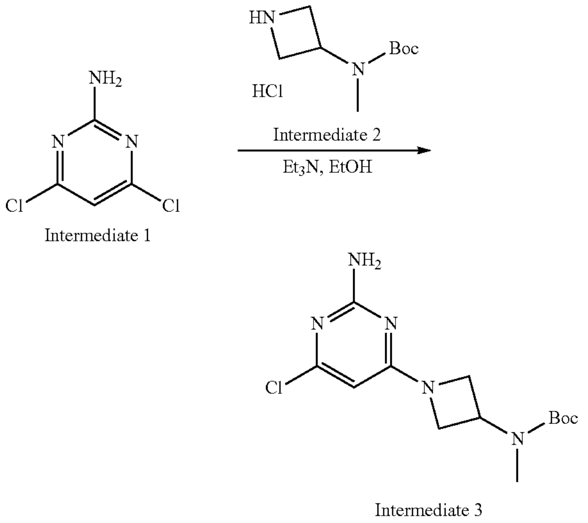

4,6-Dichloropyrimidin-2-amine Intermediate 1 (2 g, 12.27 mmol) was added portion wise to a stirred solution of tert-butyl N-(azetidin-3-yl)-N-methylcarbamate hydrochloride Intermediate 2 (3.0 g, 12.9 mmol) in EtOH (50 mL) followed by $Et_3N$ (8 mL, 30.6 mmol) at RT. The resulting suspension was warmed to reflux and maintained for 2 h. The mixture was cooled and water (30 mL) was added drop wise. The resulting solid was isolated, washed with water and dried to give tert-butyl (1-(2-amino-6-chloropyrimidin-4-yl) azetidin-3-yl) (methyl) carbamate Intermediate 3 (3 g, 79%) as a white solid.

The data for Intermediate 3 are in Table 2.

General Synthetic Procedures:

Route A

Typical procedure for the preparation of pyrimidines as exemplified by the preparation of Example 1, 4-(1-(difluoromethyl)-1H-pyrazol-4-yl)-6-(3-(methylamino)azetidin-1-yl)pyrimidin amine

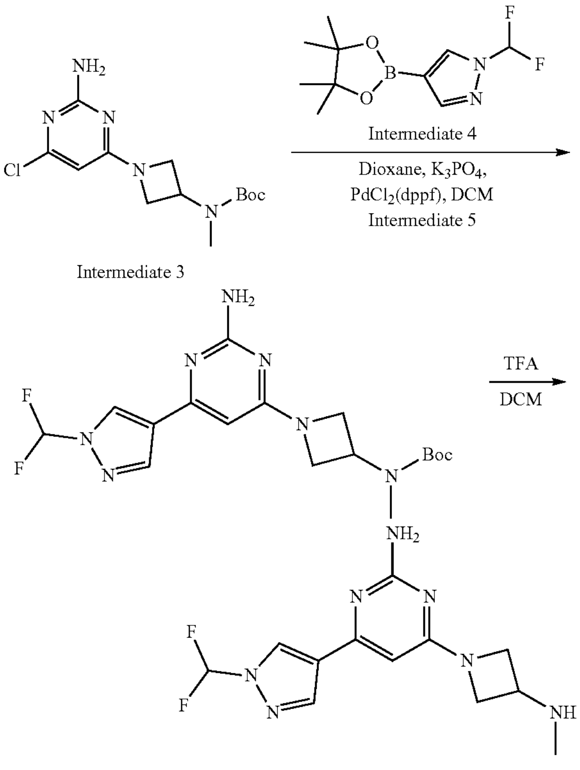

Example 1 tert-Butyl (1-(2-amino-6-chloropyrimidin-4-yl)azetidin-3-yl)(methyl)carbamate Intermediate 3, (0.350 g, 1.11 mmol), 1-(difluoromethyl)-4-(4,4,5,5-tetramethyl-1,3,2-dioxaborolan-2-yl)-1H-pyrazole Intermediate 4 (0.300 g, 1.23 mmol), $K_3PO_4$ (0.711 g, 3.36 mmol) were dissolved in 1,4-dioxane (4 mL) and water (1 mL) and the RM degassed for 15 min. Pd(dppf)$Cl_2$.DCM Intermediate 5, (0.090 g, 0.11 mmol) was added and the RM stirred at 70 °C for 16 h. The reaction mass was diluted with water (10 mL), extracted with ethyl acetate (3×20 mL), the combined organic layers were dried ($Na_2SO_4$), filtered and concentrated to give a crude residue which was purified by column chromatography (Neutral Alumina, 0-35% EtOAc: hexane) to give tert-butyl (1-(2-amino-6-(1-(difluoromethyl)-1H-pyrazol-4-yl) pyrimidin-4-yl) azetidin-3-yl) (methyl) carbamate (0.4 g, 90.7%) as an off white solid.

LCMS (System 1, Method 1): m/z 395 (M+H)+(ESI+ve), at 2.88 min, 220 nm tert-Butyl (1-(2-amino-6-(1-(difluoromethyl)-1H-pyrazol-4-yl)pyrimidin-4-yl)azetidin-3-yl)(methyl)carbamate (0.400 g, 0.10 mmol) was dissolved in DCM (4 mL), TFA was added (2 mL) drop wise at 0 °C and the RM stirred at room temperature for 3 h. The solvent was evaporated in vacuum and azeotroped with toluene (3×10 mL) to give a crude residue which was purified by Purification Method A to give the di TFA salt of 4-(1-(difluoromethyl)-1H-pyrazol-4-yl)-6-(3-(methylamino)azetidin-1-yl)pyrimidin-2-amine Example 1 (245 mg, 82.0%) as a white solid. The data for Example 1 are in Table 3.

Route B

Typical procedure for the preparation of pyrimidines as exemplified by the preparation of Example 4, 4-(1-(difluoromethyl)-3-methyl-1H-pyrazol-4-yl)-6-(3-(methylamino)azetidin-1-ylpyrimidin-2-amine and Example 16, 4-(1-(difluoromethyl)-5-methyl-1H-pyrazol-4-yl)-6-(3-(methylamino)azetidin-1-yl)pyrimidin-2-amine

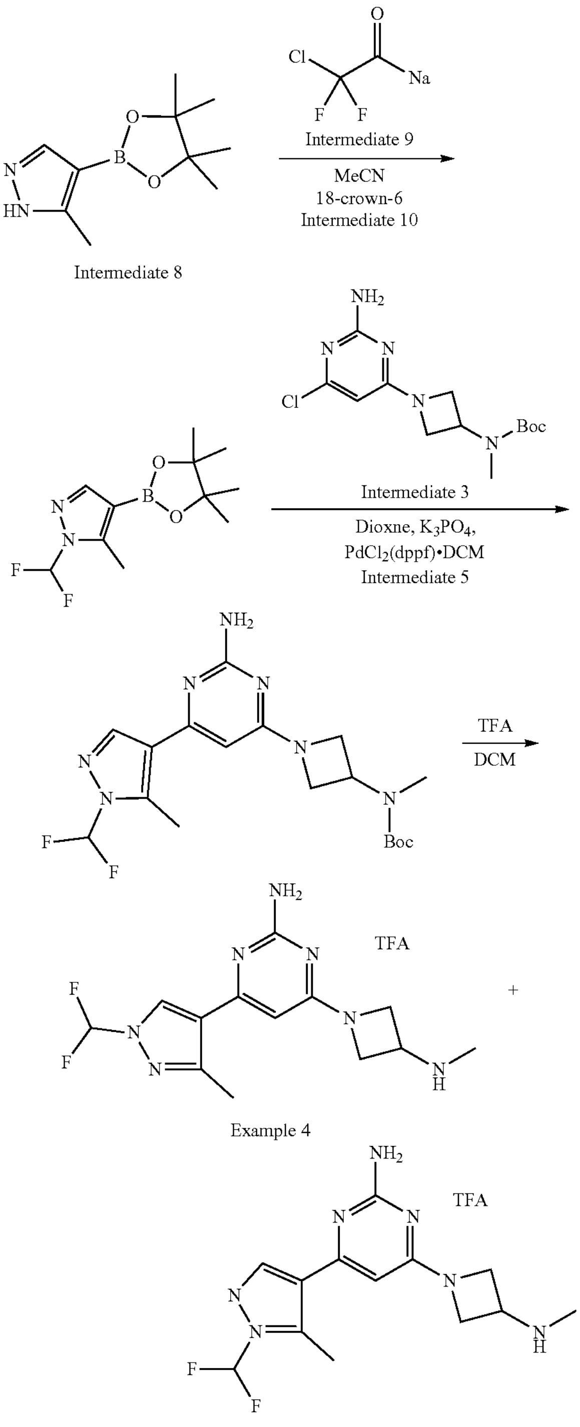

Example 16

5-Methyl-4-(4,4,5,5-tetramethyl-1,3,2-dioxaborolan-2-yl)-1H-pyrazole Intermediate 8 (1.0 g, 4.81 mmol) was dissolved in acetonitrile (10 mL), 18-Crown-6 Intermediate 10 (254 mg, 0.96 mmol) and sodium chlorodifluoroacetate Intermediate 9 (879 mg, 5.77 mmol) were added and the reaction mixture was heated at 80 °C for 24 h. After cooling, the precipitate was removed by filtration and the filtrate was concentrated to give crude product which was purified by column chromatography (Neutral Alumina, 0 to 35% Ethyl acetate in hexane) to give a mixture of 1-(difluoromethyl)-5-methyl-4-(4,4,5,5-tetramethyl-1,3,2-dioxaborolan-2-yl)-1H-pyrazole and 1-(difluoromethyl)-3-methyl-4-(4,4,5,5-tetramethyl-1,3,2-dioxaborolan-2-yl)-1H-pyrazole (combined 1 g, 80.6%) as off white solid.

LCMS (System 2, Method 2): Isomer 1, UV only at 3.52 min, 202 nm & Isomer 2, UV only at 3.63 min, 202nm.

1-(Difluoromethyl)-5-methyl-4-(4,4,5,5-tetramethyl-1,3,2-dioxaborolan-2-yl)-1H-pyrazole and 1-(difluoromethyl)-3-methyl-4-(4,4,5,5-tetramethyl-1,3,2-dioxaborolan-2-yl)-1H-pyrazole (combined 1 g, 3.87 mmol) and tert-butyl (1-(2-amino-6-chloropyrimidin-4-yl)azetidin-3-yl)(methyl) carbamate Intermediate 3 (1.1 g, 3.50 mmol) were dissolved in 1,4-dioxane (10 mL) at RT. Water (2 mL), $K_3PO_4$ (2.23 g, 10.51 mmol) were added and the mixture degassed for 15 min. $PdCl_2$(dppf).DCM Intermediate 5 (280 mg, 0.35 mmol) was added and the mixture stirred at 70 °C for 16 h. The reaction mixture was partitioned between $H_2O$ (50 mL) and ethyl acetate (35 mL), the aqueous layer was further extracted with ethyl acetate (2×35 mL), the combined organic layers were dried ($Na_2SO_4$), filtered and the solvent concentrated to give a crude residue that was purified by column chromatography (Neutral Alumina, 0 to 2% methanol in DCM) to give a mixture of tert-butyl (1-(2-amino-6-(1-(difluoromethyl)-5-methyl-1H-pyrazol-4-yl)pyrimidin-4-yl)azetidin-3-yl)(methyl)carbamate and tert-butyl (1-(2-amino-6-(1-(difluoromethyl)-3-methyl-1H-pyrazol-4-yl) pyrimidin-4-yl)azetidin-3-yl)(methyl)carbamate (combined 630 mg, 39.7%) as a yellow gum.

LCMS (System 2, Method 2): Isomer 1, m/z 410.2 (M+H)+ (ES+), at 3.35 min, 202 nm & Isomer 2, m/z 410.2 (M+H)+ (ES+), at 3.40 min, 202 nm.

tert-Butyl (1-(2-amino-6-(1-(difluoromethyl)-5-methyl-1H-pyrazol-4-yl)pyrimidin-4-yl)azetidin-3-yl)(methyl)carbamate and tert-butyl (1-(2-amino-6-(1-(difluoromethyl)-3-methyl-1H-pyrazol-4-yl)pyrimidin-4-yl)azetidin-3-yl) (methyl)carbamate (combined 800 mg, 1.95 mmol) was dissolved in DCM (8 mL) at 0 °C, TFA (4 mL) was added drop wise and the mixture stirred at room temperature for 3 h. The reaction mixture was concentrated and the crude residue was azeotroped with toluene (3×5 mL) to give crude product which was purified by Purification Method D to give 4-(1-(difluoromethyl)-3-methyl-1H-pyrazol-4-yl) -6-(3-(methylamino) azetidin-1-yl) pyrimidin-2-amine TFA salt Example 4 (362 mg, 43.8%) as a white solid and 4-(1-(difluoromethyl)-5-methyl-1H-pyrazol-4-yl)-6-(3-(methylamino) azetidin-1-yl) pyrimidin-2-amine TFA salt Example 16 (150 mg, 18.1%) as a white solid. The data for Example 4 and Example 16 are in Table 3.

Route C

Typical procedure for the preparation of pyrimidines as exemplified by the preparation of Example 5, (R)-4-(5-chloro-1-methyl-1H-pyrazol-4-yl)-6-(3-(methylamino)pyrrolidin-1-yl)pyrimidin-2-amine

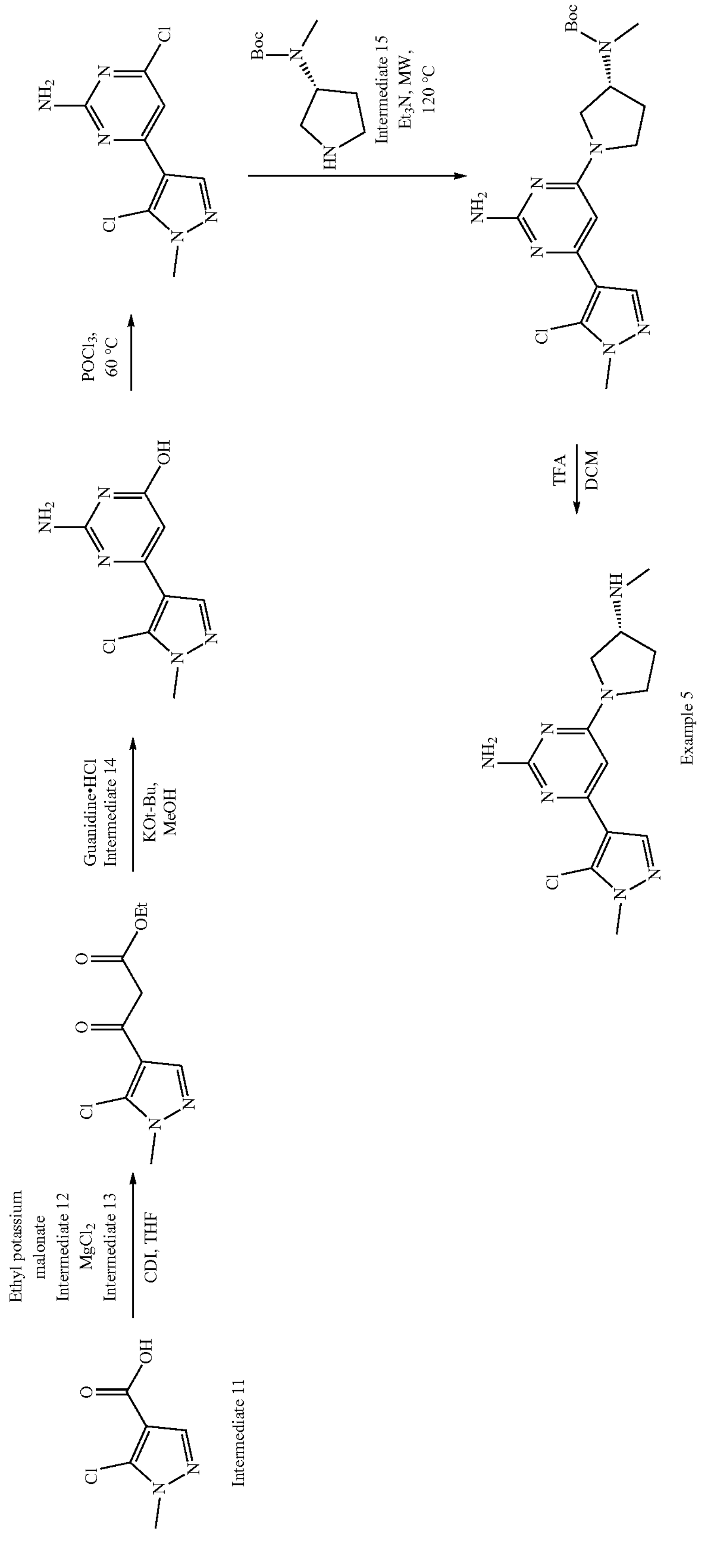
Intermediate 11
Example 5

5-Chloro-1-methyl-1H-pyrazole-4-carboxylic acid Intermediate 11 (1.0 g, 6.25 mmol) was dissolved in THF (50 mL) and cooled to 0 °C. Carbonyldiimidazole (1.51 g, 9.37 mol) was added under vigorous stirring and the mixture was stirred at RT for 1 h. The reaction mixture was cooled to 0 °C, ethyl potassium malonate Intermediate 12 (1.59 g, 9.37 mol) and magnesium chloride Intermediate 13 (0.89 g, 9.37 mol) were added and the reaction mixture was stirred at RT for 16 h. The solvent was evaporated under reduced pressure, the reaction mixture was diluted with $H_2O$ (50 mL), acidified by the addition of 1M HCl solution (10 mL), extracted with EtOAc (3×100 mL), the combined organic layers were washed with brine solution (50 mL), dried over $Na_2SO_4$ and concentrated to give ethyl 3-(5-chloro-1-methyl-1H-pyrazol-4-yl)-3-oxopropanoate (1.01 g, 70%) as an off-white solid.

LCMS (System 2, Method 2): m/z 231.1 (M+H)+(ES+), at 2.63 min, 254 nm.

Ethyl 3-(5-chloro-1-methyl-1H-pyrazol-4-yl)-3-oxopropanoate (0.9 g, 3.9 mmol) was dissolved in MeOH (15.0 mL) at 0 °C, potassium-tert-butoxide (1.31 g, 11.7 mmol) and guanidine hydrochloride Intermediate 14 (0.743 g, 7.82 mmol) were added and the reaction mixture heated at 70 °C for 16 h. After cooling to RT the solvent was evaporated under reduced pressure to give a yellow solid which was suspended in water (50 mL), acidified by the addition of 1M HCl solution (10 mL), extracted with DCM (3×50 mL), the combined organic layers were dried over $Na_2SO_4$ and concentrated under reduced pressure to give 2-amino-6-(5-chloro-1-methyl-1H-pyrazol-4-yl) pyrimidin-4-ol (0.8 g, 91%) as an off-white solid.

LCMS (System 2, Method 2): m/z 226.1 (M+H)+(ES+), at 1.81 min, 230 nm.

To a microwave vial containing 2-amino-6-(5-chloro-1-methyl-1H-pyrazol-4-yl) pyrimidin-4-ol (0.8 g, 3.5 mmol) was added phosphorus oxychloride (3.0 mL) at 0 °C and the resultant solution was heated at 70 °C for 16 h. The reaction mixture was cooled to RT, poured into ice-cold water (20 mL), the aqueous layer neutralized by adding solid $NaHCO_3$ and extracted with EtOAc (3×50 mL). The combined organic layers were washed with brine (100 mL), dried over $Na_2SO_4$ and concentrated to give 4-chloro-6-(5-chloro-1-methyl-1H-pyrazol-4-yl) pyrimidin-2-amine (0.38 g, 44%) as a white solid.

LCMS (System 2, Method 1): m/z 244.1 (M+H)+(ES+), at 2.54 min, 240 nm.

4-Chloro-6-(5-(trifluoromethyl)-1H-pyrazol-3-yl) pyrimidin-2-amine (0.18 g, 0.74 mmol) and tert-butyl (R)-methyl(pyrrolidin-3-yl) carbamate Intermediate 15 (0.296 g. 1.48 mol) was dissolved in $Et_3N$ (5.0 mL) in a 35 mL microwave vial and the resultant mixture heated at 120 °C for 16 h. After this time the reaction mixture was cooled to RT, DCM (100 mL) was added, the organic layer was washed with $H_2O$ (50 mL) and brine solution (50 mL) and concentrated to get the crude product which was purified by column chromatography (silica gel 60-120, 0-5% MeOH in DCM) to give tert-butyl (R)-(1-(2-amino-6-(5-chloro-1-methyl-1H-pyrazol-4- yl)pyrimidin-4-yl)pyrrolidin-3-yl)(methyl)carbamate (0.230 g, 76%) as a brown sticky gum.

LCMS (System 2, Method 1): m/z 408.2 (M+H)+(ES+), at 3.19 min, 254 nm.

tert-Butyl (R)-(1-(2-amino-6-(5-chloro-1-methyl-1H-pyrazol-4-yl) pyrimidin-4-yl) pyrrolidin-3-yl) (methyl) carbamate (0.23 g, 0.57 mmol) was dissolved in DCM (1.0 mL), TFA (1.0 mL) was added at 0 °C and the reaction mixture stirred at RT for 1 h. The solvent was evaporated under reduced pressure and the residue purified by Purification Method E to give (R)-4-(5-chloro-1-methyl-1H-pyrazol-4-yl)-6-(3-(methylamino) pyrrolidin-1-yl) pyrimidin-2-amine Example 5 (35 mg, 20%) as a white solid. The data for Example 5 are in Table 3.

Route D

Typical procedure for the preparation of pyrimidines as exemplified by the preparation of Example 19, 4-(3-methyl-1-(2,2,2-trifluoroethyl)-1H-pyrazol-4-yl)-6-(3-(methylamino)azetidin-1-yl)pyrimidin-2-amine

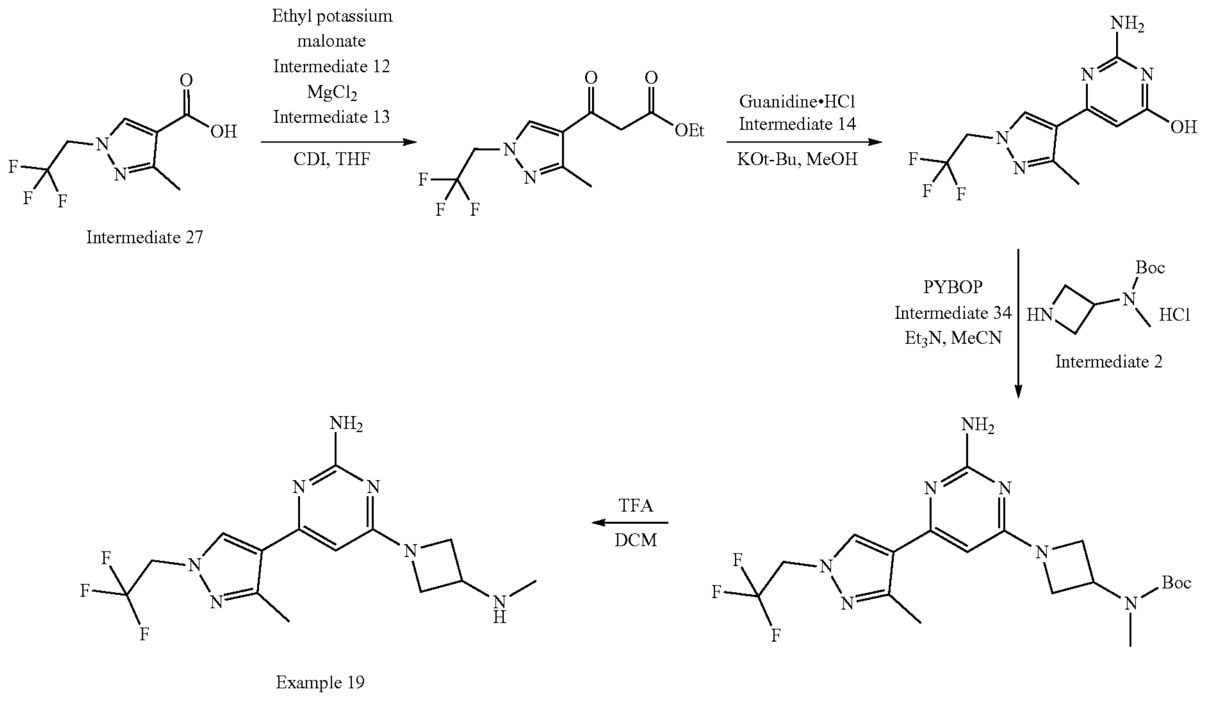

3-Methyl-1-(2,2,2-trifluoroethyl)-1H-pyrazole-4-carboxylic acid Intermediate 27 (1.0 g, 4.8 mmol) was dissolved in dry THF (100 mL) under N2 gas and solution was cooled to 0 °C. Carbonyldiimidazole (1.6 g, 9.6 mmol) was added and the mixture was stirred at RT for 1 h. The reaction mixture was cooled to 0 °C, ethyl potassium malonate Intermediate 12 (1.63 g, 9.6 mmol) and magnesium chloride Intermediate 13 (0.9 g, 9.6 mmol) were added and $H_2O$ (50 mL), the aqueous layer was acidified by adding 1N HCl solution (20 mL) and extracted with EtOAc (3×100 mL). The combined organic layers were washed with brine solution (50 mL), dried over $Na_2SO_4$ and concentrated to give the crude product, which was purified by column chromatography (Silica gel; 60- 120 mesh; 0-40% EtOAc in hexane) to get ethyl 3-(3-methyl-1-(2,2,2-trifluoroethyl)-1H-pyrazol-4-yl) oxopropanoate (0.52 g, 40%) as an off-white solid.

LCMS (System 2, Method 2): m/z 277.0 (M+H)+(ES+), at 2.84 min, 244 nm

Ethyl 3-(3-methyl-1-(2,2,2-trifluoroethyl)-1H-pyrazol-4-yl)-3-oxopropanoate (0.5 g, 1.79 mol) was dissolved in MeOH (15 mL) at 0 °C, potassium-tert-butoxide (0.6 g, 0.00539 mol) and guanidine hydrochloride Intermediate 14 (0.345 g, 3.59 mmol) were added and the reaction mixture was warmed heated at 70 °C for 16. After this time the solvent was evaporated to get a yellow color solid which was suspended in water (50 mL), acidified by the addition of 1M HCl solution (10 mL), extracted with DCM (3×50 mL), the combined organic layers were dried over $Na_2SO_4$ and concentrated under reduced pressure to give 2-amino-6-(3-methyl-1-(2,2,2-trifluoroethyl)-1H-pyrazol-4-yl) pyrimidin-4-ol (0.38 g, 77%) as an off-white solid.

LCMS (System 2, Method 2): m/z 274.2 (M+H)+(ES+), at 1.85 min, 240 nm

2-Amino-6-(3-methyl-1-(2,2,2-trifluoroethyl)-1H-pyrazol-4-yl) pyrimidin-4-ol (0.38 g, 1.39 mmol) and tert-butyl azetidin-3-yl(methyl)carbamate Intermediate 2 (0.463 g. 2.08 mmol) were dissolved in $Et_3N$ (5.0 mL) and MeCN (8.0 mL) at 0 °C. PYBOP Intermediate 34 (1.08 g, 2.08 mmol) was added at 0 °C and the reaction mixture was heated at 80 °C for 16 h. After this time the reaction mixture was cooled to RT, DCM (100 mL) was added, the organic layer was washed with $H_2O$ (50 mL) and brine solution (50 mL) and the solvents concentrated to give crude product which was purified by column chromatography (silica gel 60-120 mesh, 0-5% MeOH in DCM) to give tert-butyl (1-(2-amino-6-(3-methyl-1-(2,2,2-trifluoroethyl)-1H-pyrazol-4-yl)pyrimidin-4-yl)azetidin-3-yl)(methyl)carbamate (0.410 g, 66%) as a brown sticky gum.

LCMS (System 2, Method 1): m/z 442.3 (M+H)+(ES+), at 3.03 min, 214 nm tert-Butyl (1-(2-amino-6-(3-methyl-1-(2,2,2-trifluoroethyl)-1H-pyrazol-4-yl) pyrimidin-4-yl) azetidin-3-yl) (methyl)carbamate (0.41 g, 0.929 mmol) was dissolved in DCM (2.0 mL) at 0 °C, TFA (2.0 mL) was added and the reaction mixture was stirred at RT for 1 h. The solvent was evaporated under reduced pressure and the residue purified by Purification Method R to give 4-(3-methyl-1-(2,2,2-trifluoroethyl)-1H-pyrazol-4-yl)-6-(3-(methylamino)azetidin-1-yl)pyrimidin-2-amine Example 19 (27 mg, 33%) as a white solid. The data for Example 19 are in Table 3.

Route E

Typical procedure for the preparation of pyrimidines as exemplified by the preparation of Example 36, 4-(3-(methylamino)azetidin-1-yl)-6-(1H-pyrazol-3-yl)pyrimidin-2-amine

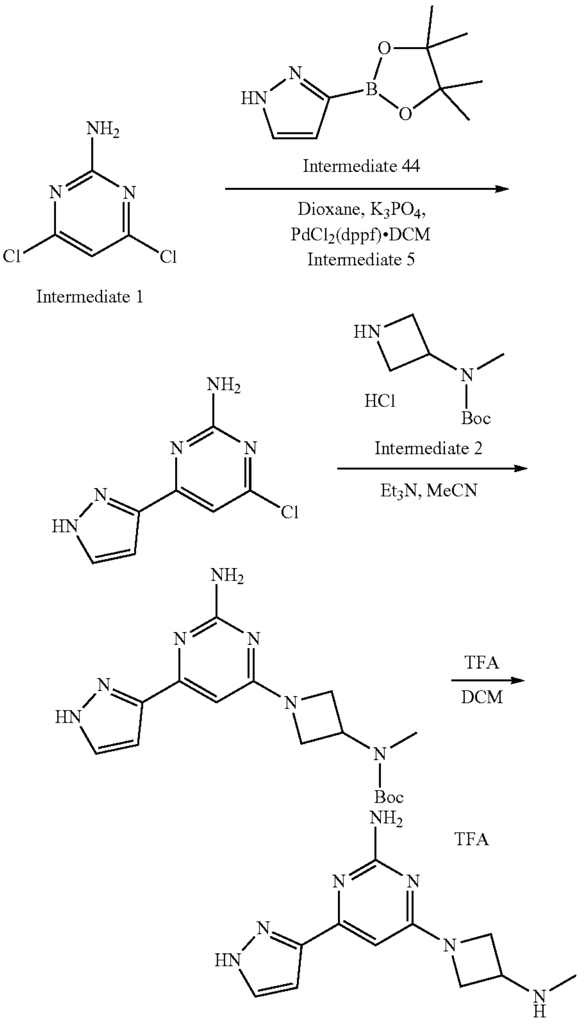

Example 36

4,6-Dichloropyrimidin-2-amine Intermediate 1 (1 g, 12.0 mmol), 3-(4,4,5,5-tetramethyl-1,3,2-dioxaborolan-2-yl)-1H-pyrazole Intermediate 44 (1.40 g, 7.20 mmol) and $K_3PO_4$ (3.88 g, 18.9 mmol) were dissolved in 1,4-dioxane (20 mL) and water (4 mL) under nitrogen and degassed for 20 min. Pd(dppf)Cl2.DCM Intermediate 5 (497 mg, 0.60 mmol) was added and the reaction mixture was stirred at 80 °C for 16 h. After cooling, the reaction mixture was diluted with water (50 mL), extracted with ethyl acetate (3×50 mL), the combined organics were dried ($Na_2SO_4$), filtered and concentrated to give a crude residue which was purified by column chromatography (Silica gel; 60-120 mesh, 0-28% EtOAc in hexane) to give 4-chloro-6-(1H-pyrazol-3-yl) pyrimidin-2-amine (230 mg, 19.5%) as an off white solid.

LCMS (System 1, Method 1): m/z 196 (M+H)+(ES+), at 2.62 min, 254 nm

4-Chloro-6-(1H-pyrazol-3-yl)pyrimidin-2-amine (210 mg, 1.0 mmol) and tert-butyl azetidin-3-yl(methyl)carbamate hydrochloride Intermediate 2 (401 mg, 2.1 mmol) were dissolved in MeCN (10 mL), $Et_3N$ (4 mL) was added and the reaction stirred at 90 °C for 6 h. The reaction mixture cooled, diluted with water (30 mL), extracted with ethyl acetate (3×30 mL), the combined organics were dried ($Na_2SO_4$), filtered and concentrated give crude tert-butyl (1-(2-amino-6-(1H-pyrazol-3-yl) pyrimidin-4-yl) azetidin-3-yl)(methyl) carbamate (assumed 100%) as an off white solid which was used crude without purification.

LCMS (System 1, Method 1): m/z 346 (M+H)+(ES+), at 2.98 min, 240 nm tert-Butyl (1-(2-amino-6-(1H-pyrazol-3-yl)pyrimidin-4-yl)azetidin-3-yl)(methyl)carbamate (570 mg, 1.6 mmol) was dissolved in DCM (3 mL) at 0 °C, TFA was added (1.5 mL) drop wise and the reaction mixture stirred at room temperature for 3 h. The solvent was concentrated and the residue azeotroped with toluene (3×3 mL) to give crude product which was purified by Purification Method AI to give 4-(3-(methylamino)azetidin-1-yl)-6-(1H-pyrazol-3-yl)pyrimidin-2-amine Example 36 (151 mg, 37.3%) as a white solid. The data for Example 36 are in Table 3.

Route F

Procedure for the preparation of Example 20, 4-(3-methyl-1-(trifluoromethyl)-1H-pyrazol-4-yl)-6-(3-(methylamino) azetidin-1-yl)pyrimidin-2-amine and Example 23, 4-(5-methyl-1-(trifluoromethyl)-1H-pyrazol-4-yl)-6-(3-(methylamino)azetidin-1-yl)pyrimidin-2-amine

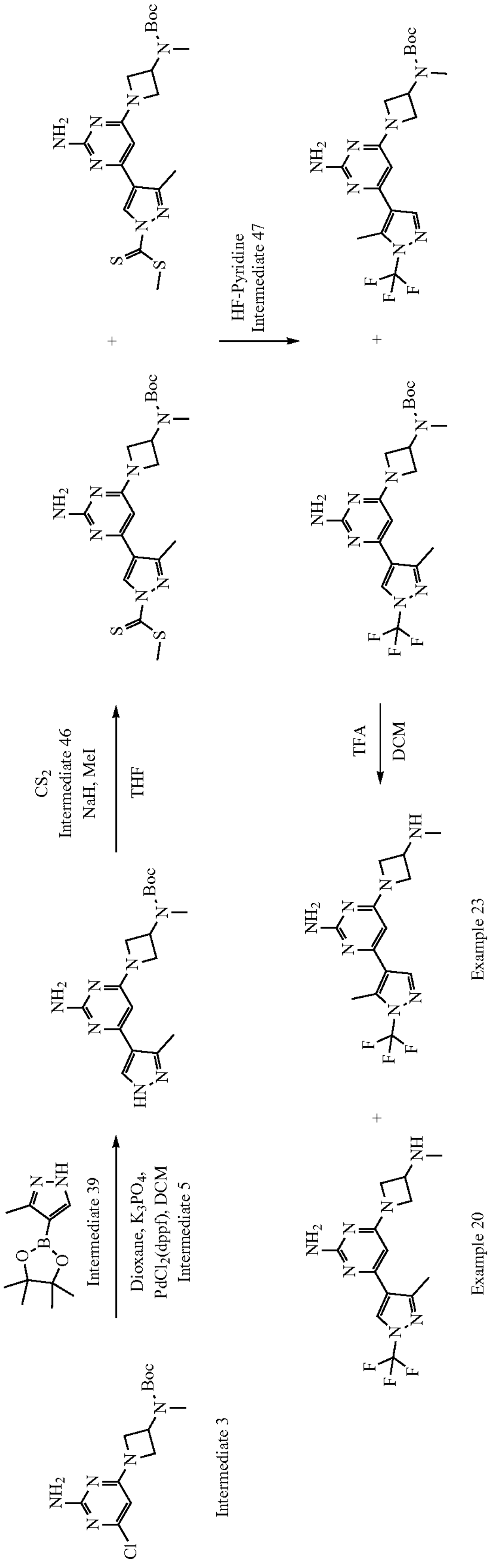
Intermediate 3
Example 20
Example 23

Route G

Procedure for the preparation of Example 32, 4-(3-(methylamino)azetidin-1-y0-6-(1-(trifluoromethyl)-1H-pyrazol-4-yl)pyridin-2-amine and Example 33, (R)-4-(3-(methylamino)pyrrolidin-1-yl)-6-(1-(trifluoromethyl)-1H-pyrazol-4-yl)pyridin-2-amine

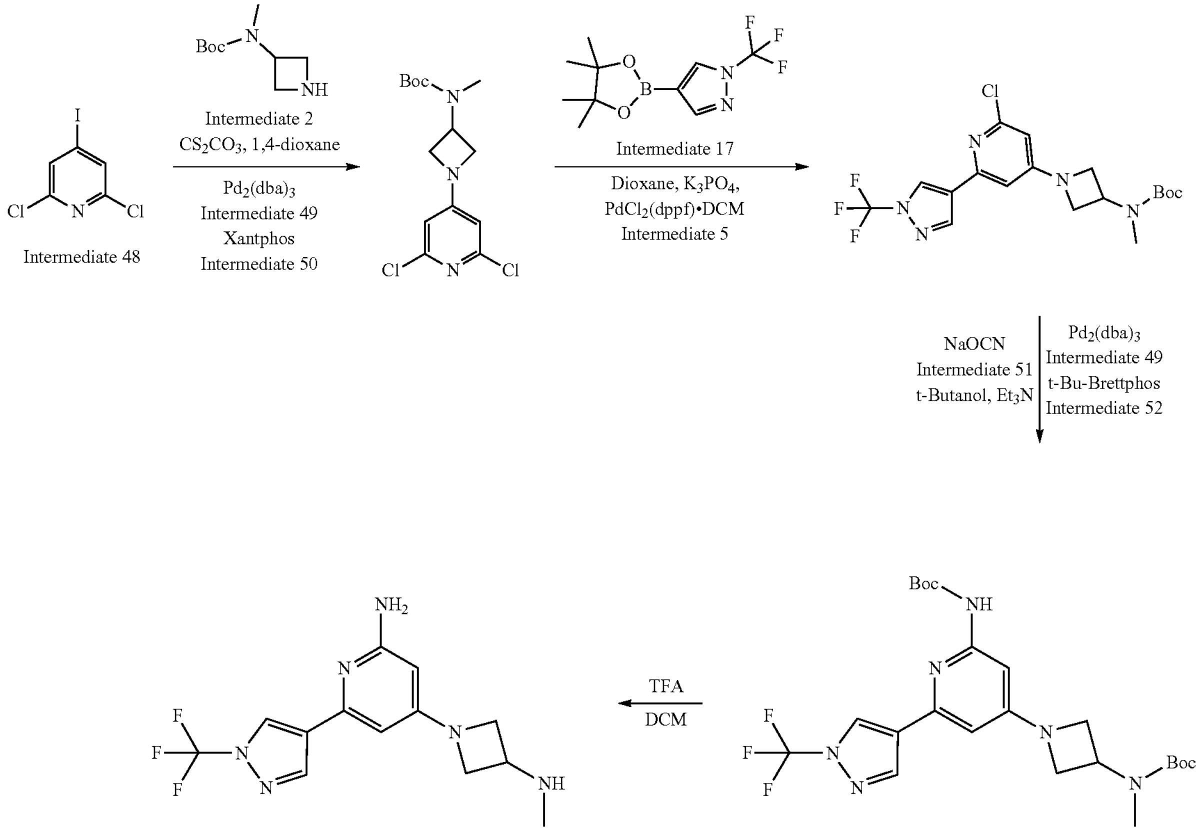

Example 32

For the synthesis of Example 33 substitute Intermediate 2 with Intermediate 17.

Route H

Procedure for the preparation of Example 40, 4-(5-ethyl-4-methyl-1H-pyrazol-3-yl)-6-(3-(methylamino)azetidin-1-yl)pyrimidin-2-amine

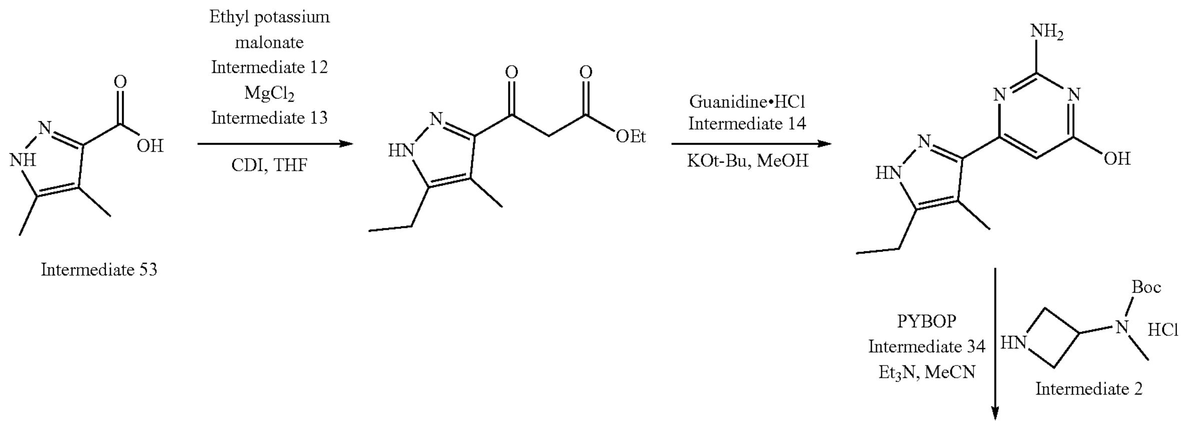

-continued

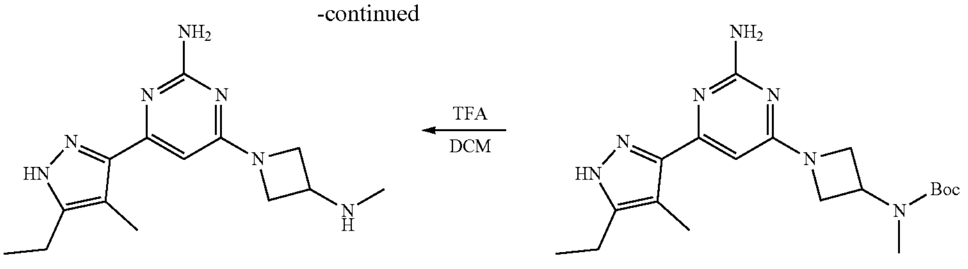

Example 40

5-Ethyl-4-methyl-1H-pyrazole-3-carboxylic acid Intermediate 53 (0.75 g, 4.87 mmol) was dissolved in dry THF (100 mL) and the solution was cooled to 0 °C. Carbonyldiimidazole (1.57 g, 9.74 mmol) was added under vigorous stirring and the mixture was stirred at RT for 1 h. The reaction mixture was cooled to 0 °C, followed by the addition of ethyl potassium malonate Intermediate 12 (1.62 g, 9.74 mmol) and magnesium chloride Intermediate 13 (0.935 g, 9.74 mol) and the reaction mixture was stirred at RT overnight. After the completion of the reaction, solvent was evaporated under reduced pressure, the reaction mixture was diluted with $H_2O$ (50 mL), the aqueous layer was acidified by adding 1N HCl solution (30 mL), extracted with EtOAc (3×100 mL) and the combined organic layers were washed with brine solution (50 mL), dried over $Na_2SO_4$, filtered and concentrated to give crude product, which was purified by column chromatography (Silica gel; 60-120 mesh; 0-40% EtOAc/Hexane) to give ethyl 3-(5-ethyl-4-methyl-1H-pyrazol-3-yl)-3-oxopropanoate (0.71 g, 65%) as an off-white solid.

LCMS (System 1, Method 2): m/z 225.3 (M+H)+(ES+), at 2.80 min, 240 nm

Ethyl 3-(5-ethyl-4-methyl-1H-pyrazol-3-yl)-3-oxopropanoate (0.7 g, 3.12 mmol) was dissolved in MeOH (15 mL), potassium-tert-butoxide (1.05 g, 9.37 mmol) and guanidine hydrochloride Intermediate 14 (0.6 g, 6.25 mmol) were added at 0 °C, the reaction mixture was warmed to RT and then heated at 70 °C overnight. After completion of the reaction, the reaction mixture was cooled to RT, the solvent was evaporated under reduced pressure to get a yellow solid, which was acidified by drop wise addition of 1 N HCl (5 mL) and the aqueous layer was extracted with EtOAc (3×50 mL). The combined organic layers were washed with brine solution (50 mL), dried over $Na_2SO_4$ and concentrated under reduced pressure to give 2-amino-6-(5-ethyl-4-methyl-1H-pyrazol-3-yl) pyrimidin-4-01 (0.68 g, 99%) as an off-white solid.

LCMS (System 1, Method 2): m/z 220.3 (M+H)+(ES+), at 1.81 min, 202 nm

POCl3 (2.0 mL) was added to 2-amino-6-(5-ethyl-4-methyl-1H-pyrazol-3-yl) pyrimidin-4-ol (0.68 g, 3.1 mmol) at 0 °C and the reaction mixture was heated at 70 °C overnight. After the completion of the reaction, reaction mixture was poured into an ice bath, neutralized by adding solid $NaHCO_3$, the aqueous layer was extracted with EtOAc (3×50 mL) and the combined organic layers were washed with brine solution (50 mL), dried over $Na_2SO_4$, filtered and concentrated to give a crude residue which was purified by column chromatography (Silica gel; 60-120 mesh; 0-40% EtOAc/Hexane) to give 4-chloro-6-(5-ethyl-4-methyl-1H-pyrazol-3-yl) pyrimidin-2-amine (401 mg, 54%) as a yellow solid.

LCMS (System 2, Method 2): m/z 238.3 (M+H)+(ES+), at 2.75 min, 214 nm

4-Chloro-6-(5-ethyl-4-methyl-1H-pyrazol-3-yl) pyrimidin-2-amine (189 mg, 7.97 mmol) and tert-butyl azetidin-3-yl(methyl)carbamate Intermediate 2 (0.354 g. 1.59 mmol) were dissolved in triethylamine (5.0 mL) and the reaction mixture was heated at 120 °C overnight. After the completion of the reaction, the reaction mixture was cooled to RT, DCM (100 mL) was added, the organic layer was washed with $H_2O$ (50 mL), brine (50 mL), and concentrated to give crude product, which was purified by column chromatography (silica gel 60-120 mesh, 0-5% MeOH: DCM) to give tert-butyl (1-(2-amino-6-(5-ethyl-4-methyl-1H-pyrazol-3-yl) pyrimidin-4-yl) azetidin-3-yl) (methyl)carbamate (230 mg, 74%) as a brown sticky gum.

LCMS (System 2, Method 1): m/z 273.3 (M+H)+(ES+), at 3.03 min, 202 nm tert-Butyl (1-(2-amino-6-(5-ethyl-4-methyl-1H-pyrazol-3-yl) pyrimidin-4-yl) azetidin-3-yl) (methyl)carbamate (230 mg, 5.94 mmol) was dissolved in DCM (2.0 mL), TFA (2.0 mL) was added at 0 °C and the reaction mixture was stirred at RT for 1h. The solvent was evaporated under reduced pressure and the crude product obtained was purified by prep-HPLC to give the ditrifluoro acetate salt of 4-(5-ethyl-4-methyl-1H-pyrazol-3-yl)-6-(3-(methylamino) azetidin-1-yl) pyrimidin-2-amine Example 40 (33 mg, 19%) as a white solid. The data for Example 40 are in Table 3.

TABLE 2

| Intermediates | | | | |
|---|---|---|---|---|
| Intermediate Number | Name | Synthetic Route | Intermediates Used | Data |
| 1 | 4,6-Dichloropyrimidin-2-amine | — | — | Commercially available, CAS: 56-05-3 |
| 2 | tert-Butyl azetidin-3-yl(methyl)carbamate hydrochloride | — | — | Commercially available, CAS: 943060-59-1 |

TABLE 2-continued

| Intermediates | | | | |
|---|---|---|---|---|
| Intermediate Number | Name | Synthetic Route | Intermediates Used | Data |
| 3 | tert-Butyl (1-(2-amino-6-chloropyrimidin-4-yl)azetidin-3-yl)(methyl)carbamate | 1 | 1 & 2 | LCMS (System 1, Method 1): m/z 314.2 $(M + H)^+$ (ES+), at 3.53 min, 262 nm |
| 4 | 1-(Difluoromethyl)-4-(4,4,5,5-tetramethyl-1,3,2-dioxaborolan-2-yl)-1H-pyrazole | — | — | Commercially available, CAS: 1206640-82-5 |
| 5 | Pd(dppf)$Cl_2$•DCM | — | — | Commercially available, CAS: 95464-05-4 |
| 6 | 4-(4,4,5,5-Tetramethyl-1,3,2-dioxaborolan-2-yl)-1-(2,2,2-trifluoroethyl)-1H-pyrazole | — | — | Commercially available, CAS: 1049730-42-8 |
| 7 | 1-Ethyl-4-(4,4,5,5-tetramethyl-1,3,2-dioxaborolan-2-yl)-1H-pyrazole | — | — | Commercially available, CAS: 847818-70-6 |
| 8 | 5-Methyl-4-(4,4,5,5-tetramethyl-1,3,2-dioxaborolan-2-yl)-1H-pyrazole | — | — | Commercially available, CAS: 936250-20-3 |
| 9 | Sodium chlorodifluoroacetate | — | — | Commercially available, CAS: 1895-39-2 |
| 10 | 18-Crown-6 | — | — | Commercially available, CAS: 17455-13-9 |
| 11 | 5-Chloro-1-methyl-1H-pyrazole-4-carboxylic acid | — | — | Commercially available, CAS: 54367-66-7 |
| 12 | Ethyl potassium malonate | — | — | Commercially available, CAS: 6148-64-7 |
| 13 | Magnesium chloride | — | — | Commercially available, CAS: 7786-30-3 |
| 14 | Guanidine hydrochloride | — | — | Commercially available, CAS: 50-01-1 |
| 15 | tert-Butyl (R)-methyl(pyrrolidin-3-yl) carbamate | — | — | Commercially available, CAS: 392338-15-7 |
| 16 | tert-Butyl azetidin-3-ylcarbamate hydrochloride | — | — | Commercially available, CAS: 217806-26-3 |
| 17 | 4-(4,4,5,5-Tetramethyl-1,3,2-dioxaborolan-2-yl)-1-(trifluoromethyl)-1H-pyrazole | — | — | Commercially available, CAS: 1046831-98-4 |
| 18 | tert-Butyl azetidin-3-yl(ethyl) carbamate | — | — | Commercially available, CAS: 929716-69-8 |
| 19 | 1,4-Dimethyl-3-(4,4,5,5-tetramethyl-1,3,2-dioxaborolan-2-yl)-1H-pyrazole | — | — | Commercially available, CAS: 2223043-80-7 |
| 20 | 1-(2,2-Difluoroethyl)-4-(4,4,5,5-tetramethyl-1,3,2-dioxaborolan-2-yl)-1H-pyrazole | — | — | Commercially available, CAS: 1049730-40-6 |
| 21 | 1-(2-Fluoroethyl)-4-(4,4,5,5-tetramethyl-1,3,2-dioxaborolan-2-yl)-1H-pyrazole | — | — | Commercially available, CAS: 1049730-39-3 |
| 22 | 1-Isopropyl-3-methyl-4-(4,4,5,5-tetramethyl-1,3,2-dioxaborolan-2-yl)-1H-pyrazole | — | — | Commercially available, CAS: 2068065-34-7 |
| 23 | 5-Methyl-1-(2,2,2-trifluoroethyl)-1H-pyrazole-4-carboxylic acid | — | — | Commercially available, CAS: 288251-53-6 |
| 24 | 1-Ethyl-3-methyl-4-(4,4,5,5-tetramethyl-1,3,2-dioxaborolan-2-yl)-1H-pyrazole | — | — | Commercially available, CAS: 2019997-43-2 |
| 25 | 4-Methyl-5-(trifluoromethyl)-1H-pyrazole-3-carboxylic acid | — | — | Commercially available, CAS: 1623156-88-6 |
| 26 | 1,3-Dimethyl-4-(4,4,5,5-tetramethyl-1,3,2-dioxaborolan-2-yl)-1H-pyrazole | — | — | Commercially available, CAS: 1046832-21-6 |
| 27 | 3-Methyl-1-(2,2,2-trifluoroethyl)-1H-pyrazole-4-carboxylic acid | — | — | Commercially available, CAS: 113100-55-3 |
| 28 | 1-Ethyl-5-methyl-1H-pyrazole-4-carboxylic acid | — | — | Commercially available, CAS: 887408-72-2 |
| 29 | 1-Isopropyl-5-methyl-1H-pyrazole-4-carboxylic acid | — | — | Commercially available, CAS: 1007541-94-7 |
| 30 | 1,3-Dimethyl-5-(4,4,5,5-tetramethyl-1,3,2-dioxa borolan-2-yl)-1H-pyrazole | — | — | Commercially available, CAS: 847818-79-5 |
| 31 | 3-Ethyl-1-methyl-1H-pyrazole-5-carboxylic acid | — | — | Commercially available, CAS: 26308-42-9 |
| 32 | 3-Chloro-1-methyl-1H-pyrazole-5-carboxylic acid | — | — | Commercially available, CAS: 173841-02-6 |
| 33 | (1-Methyl-3-(trifluoromethyl)-1H-pyrazol-5-yl)boronic acid | — | — | Commercially available, CAS: 344591-91-9 |

TABLE 2-continued

| Intermediates | | | | |
|---|---|---|---|---|
| Intermediate Number | Name | Synthetic Route | Intermediates Used | Data |
| 34 | PYBOP | — | — | Commercially available, CAS: 128625-52-5 |
| 35 | 3,5-Dichloro-1-methyl-1H-pyrazole-4-carboxylic acid | — | — | Commercially available, CAS: 134589-53-0 |
| 36 | 3-Chloro-1-methyl-1H-pyrazole-4-carboxylic acid | — | — | Commercially available, CAS: 137343-52-3 |
| 37 | 5-Bromo-1-methyl-1H-pyrazole-4-carboxylic acid | — | — | Commercially available, CAS: 54367-67-8 |
| 38 | 4-(4,4,5,5-Tetramethyl-1,3,2-dioxaborolan-2-yl)-3-(trifluoromethyl)-1H-pyrazole | — | — | Commercially available, CAS: 1218790-40-9 |
| 39 | 3-Methyl-4-(4,4,5,5-tetramethyl-1,3,2-dioxaborolan-2-yl)-1H-pyrazole | — | — | Commercially available, CAS: 936250-20-3 |
| 40 | 4,5-Dichloro-1H-pyrazole-3-carboxylic acid | — | — | Commercially available, CAS: 115964-19-7 |
| 41 | 3-Bromo-1-methyl-1H-pyrazole-4-carboxylic acid | — | — | Commercially available, CAS: 1399653-86-1 |
| 42 | 4-(4,4,5,5-Tetramethyl-1,3,2-dioxaborolan-2-yl)-1H-pyrazole | — | — | Commercially available, CAS: 269410-08-4 |
| 43 | 5-Methyl-1H-pyrazole-3-carboxylic acid | — | — | Commercially available, CAS: 402-61-9 |
| 44 | 3-(4,4,5,5-Tetramethyl-1,3,2-dioxaborolan-2-yl)-1H-pyrazole | — | — | Commercially available, CAS: 844501-71-9 |
| 45 | 5-Ethyl-1H-pyrazole-3-carboxylic acid | — | — | Commercially available, CAS: 4027-59-2 |
| 46 | Carbon disulphide | — | — | Commercially available, CAS: 75-15-0 |
| 47 | HF-pyridine | — | — | Commercially available, CAS: 62778-11-4 |
| 48 | 2,6-Dichloro-4-iodopyridine | — | — | Commercially available, CAS: 98027-84-0 |
| 49 | $Pd_2(dba)_3$ | — | — | Commercially available, CAS: 51364-51-3 |
| 50 | Xantphos | — | — | Commercially available, CAS: 161265-03-8 |
| 51 | Sodium cyanate | — | — | Commercially available, CAS: 917-61-3 |
| 52 | t-Bu-Brettphos | — | — | Commercially available, CAS: 1160861-53-9 |
| 53 | 5-Ethyl-4-methyl-1H-pyrazole-3-carboxylic acid | — | — | Commercially available, CAS: 957129-38-3 |

TABLE 3

Example compounds

| Ex. No. | Name | Synthetic Method and Intermediates Used | Purification or Isolation Method | $^{1}$H NMR | LCMS System and Method | LCMS data |
|---|---|---|---|---|---|---|
| 1 | 4-(1-(Difluoromethyl)-1H-pyrazol-4-yl)-6-(3-(methylamino)azetidin-1-yl)pyrimidin-2-amine | A<br>3, 4 & 5 | RP HPLC Method A | 1H NMR (400 MHz, Methanol-d4) δ 2.80 (s, 3H), 4.25-4.35 (m, 1H), 4.35-4.45 (m, 2H), 4.58-4.72 (m, 2H), 6.51 (s, 1H), 7.66 (t, J = 60 Hz, 1H), 8.33 (s, 1H), 8.86 (s, 1H). Four exchangeable protons not observed. | System 1 Method 1 | m/z 296.3 $(M + H)^+$ (ES+), at 1.91 min, 202 nm |
| 2 | 4-(3-(Methylamino)azetidin-1-yl)-6-(1-(2,2,2-trifluoroethyl)-1H-pyrazol-4-yl)pyrimidin-2-amine | A<br>3, 6 & 5 | RP HPLC Method B | 1H NMR (400 MHz, Methanol-d4) δ 2.81 (s, 3H), 4.23-4.32 (m, 1H), 4.32-4.46 (m, 2H), 4.56-4.72 (m, 2H), 5.12 (q, J = 8.6 Hz, 2H), 6.42 (s, 1H), 8.23 (s, 1H), 8.56 (s, 1H). Five exchangeable protons not observed. | System 1 Method 2 | m/z 328.2 $(M + H)^+$ (ES+), at 2.07 min, 240 nm |
| 3 | 4-(1-Ethyl-1H-pyrazol-4-yl)-6-(3-(methylamino)azetidin-1-yl)pyrimidin-2-amine | A<br>3, 7 & 5 | RP HPLC Method C | 1H NMR (400 MHz, Methanol-d4) δ 1.51 (t, J = 7.3 Hz, 3H), 2.78 (s, 3H), 4.11-4.45 (m, 5H), 4.60 (s, 2H), 6.34 (s, 1H), 8.09 (s, 1H), 8.39 (s, 1H). Three exchangeable protons not observed. | System 2 Method 2 | m/z 274.2 $(M + H)^+$ (ES+), at 1.87 min, 254 nm |
| 4 | 4-(1-(Difluoromethyl)-3-methyl-1H-pyrazol-4-yl)-6-(3-(methylamino)azetidin-1-yl)pyrimidin-2-amine | B<br>8, 9, 10, 3 & 5 | RP HPLC Method D | 1H NMR (400 MHz, Methanol-d4) δ 2.51 (s, 3H), 2.81 (s, 3H), 4.24-4.34 (m, 1H), 4.34-4.49 (m, 2H), 4.58-4.74 (m, 2H), 6.18 (s, 1H), 7.65 (t, J = 59.5 Hz, 1H), 8.59 (s, 1H). Three exchangeable protons not observed. | System 1 Method 2 | m/z 310.2 $(M + H)^+$ (ES+), at 1.97 min, 240 nm |
| 5 | (R)-4-(5-Chloro-1-methyl-1H-pyrazol-4-yl)-6-(3-(methylamino)pyrrolidin-1-yl)pyrimidin-2-amine | C<br>11, 12, 13, 14 & 15 | RP HPLC Method E | 1H NMR (400 MHz, DMSO-d6) δ 1.76 (s, 1H), 2.02 (s, 1H), 2.28 (s, 3H), 3.08-3.54 (m, 5H), 3.83 (s, 3H), 5.97 (s, 2H), 6.11 (s, 1H), 7.94 (s, 1H). One exchangeable proton not observed. | System 2 Method 1 | m/z 308.2 $(M + H)^+$ (ES+), at 1.86 min, 242 nm |
| 6 | 4-(3-Aminoazetidin-1-yl)-6-(1-(trifluoromethyl)-lH-pyrazol-4-yl)pyrimidin-2-amine | 1 & A<br>1, 16, 17 & 5 | RP HPLC Method F | 1H NMR (400 MHz, Methanol-d4) δ 4.17-4.45 (m, 3H), 4.52-4.77 (m, 2H), 6.52 (s, 1H), 8.44 (s, 1H), 9.02 (s, 1H). Six exchangeable protons not observed. | System 1 Method 2 | m/z 300.2 $(M + H)^+$ (ES+), at 2.04 min, 235 nm |
| 7 | 4-(3-(Ethylamino)azetidin-1-yl)-6-(1-(trifluoromethyl)-1H-pyrazol-4-yl)pyrimidin-2-amine | 1 & A<br>1, 18, 17 & 5 | RP HPLC Method G | 1H NMR (400 MHz, Methanol-d4) δ 1.36 (t, J = 7.3 Hz, 3H), 3.14 (q, J = 7.3 Hz, 2H), 4.25-4.46 (m, 3H), 4.55-4.72 (m, 2H), 6.50 (s, 1H), 8.41 (s, 1H), 8.96 (s, 1H). Five exchangeable protons not observed. | System 1 Method 2 | m/z 328.2 $(M + H)^+$ (ES+), at 2.95 min, 235 nm |
| 8 | 4-(1,4-Dimethyl-1H-pyrazol-3-yl)-6-(3-(methylamino)azetidin-1-yl)pyrimidin-2-amine | A<br>3, 19 & 5 | RP HPLC Method H | 1H NMR (400 MHz, Methanol-d4) δ 2.27 (s, 3H), 2.38 (s, 3H), 3.65-3.78 (m, 1H), 3.78-3.95 (m, 5H), 4.22-4.36 (m, 2H), 6.05 (s, 1H), 7.44 (s, 1H). Three exchangeable protons not observed. | System 2 Method 1 | m/z 274.5 $(M + H)^+$ (ES+), at 1.95 min, 202 nm |
| 9 | 4-(1-(2,2-Difluoroethyl)-1H-pyrazol-4-yl)-6-(3-(methylamino)azetidin-1-yl)pyrimidin-2-amine | A<br>3, 20 & 5 | RP HPLC Method I | 1H NMR (400 MHz, Methanol-d4) δ 2.78 (s, 3H), 4.20-4.47 (m, 3H), 4.53-4.77 (m, 4H), 6.07-6.47 (m, 2H), 8.17 (s, 1H), 8.45 (s, 1H). Four exchangeable protons not observed. | System 2 Method 2 | m/z 310.2 $(M + H)^+$ (ES+), at 1.95 min, 230 nm |
| 10 | 4-(1-(2-Fluoroethyl)-1H-pyrazol-4-yl)-6-(3-(methylamino)azetidin-1-yl)pyrimidin-2-amine | A<br>3, 21 & 5 | RP HPLC Method J | 1H NMR (400 MHz, Methanol-d4) δ 2.36 (s, 3H), 3.63-3.76 (m, 1H), 3.77-3.89 (m, 2H), 4.20-4.31 (m, 2H), 4.40-4.57 (m, 2H), 4.67-4.85 (m, 2H), 6.00 (s, 1H), 8.02 (s, 1H), 8.18 (s, 1H). Three exchangeable protons not observed. | System 1 Method 1 | m/z 292.4 $(M + H)^+$ (ES+), at 1.68 min, 311 nm |
| 11 | 4-(1-Isopropyl-3-methyl-1H-pyrazol-4-yl)-6-(3-(methylamino)azetidin-1-yl)pyrimidin-2-amine | A<br>3, 22 & 5 | RP HPLC Method K | 1H NMR (400 MHz, Methanol-d4) δ 1.51 (d, J = 6.7 Hz, 6H), 2.45 (s, 3H), 2.78 (s, 3H), 4.21-4.71 (m, 6H), 6.02 (s, 1H), 8.22 (s, 1H). Three exchangeable protons not observed. | System 2 Method 2 | m/z 302.2 $(M + H)^+$ (ES+), at 2.07 min, 242 nm |

TABLE 3-continued

| Ex. No. | Name | Synthetic Method and Intermediates Used | Purification or Isolation Method | $^1$H NMR | LCMS System and Method | LCMS data |
|---|---|---|---|---|---|---|
| Example compounds | | | | | | |
| 12 | 4-(5-Methyl-1-(2,2,2-trifluoroethyl)-1H-pyrazol-4-yl)-6-(3-(methylamino)azetidin-1-yl)pyrimidin-2-amine | C<br>23, 12, 13, 14 & 2 | RP HPLC<br>Method L | 1H NMR (400 MHz, Methanol-d4) δ 2.56 (s, 3H), 2.78 (s, 3H), 4.17-4.73 (m, 5H), 5.07 (q, J = 8.6 Hz, 2H), 6.07 (s, 1H), 7.93 (s, 1H). Three exchangeable protons not observed. | System 1<br>Method 1 | m/z 342.4 $(M + H)^+$ (ES+), at 2.06 min, 225 nm |
| 13 | 4-(1-Ethyl-3-methyl-1H-pyrazol-4-yl)-6-(3-(methylamino)azetidin-1-yl)pyrimidin-2-amine | A<br>3, 24 & 5 | RP HPLC<br>Method M | 1H NMR (400 MHz, Methanol-d4) δ 1.48 (t, J = 7.3 Hz, 3H), 2.44 (s, 3H), 2.78 (s, 3H), 4.19 (q, J = 7.4 Hz, 2H), 4.21-4.31 (m, 1H), 4.49 (m, 4H), 6.02 (s, 1H), 8.17 (s, 1H). Three exchangeable protons not observed. | System 2<br>Method 2 | m/z 288.2 $(M + H)^+$ (ES+), at 1.95 min, 254 nm |
| 14 | (R)-4-(1-Ethyl-3-methyl-1H-pyrazol-4-yl)-6-(3-(methylamino)pyrrolidin-1-yl)pyrimidin-2-amine | 1 & A<br>1, 15, 24 & 5 | RP HPLC<br>Method N | 1H NMR (400 MHz, Methanol-d4) δ 1.49 (t, J = 7.3 Hz, 3H), 2.35 (s, 1H), 2.46 (s, 3H), 2.53-2.65 (m, 1H), 2.81 (s, 3H), 3.69-4.09 (m, 5H), 4.20 (q, J = 7.3 Hz, 2H), 6.18 (s, 1H), 8.17 (s, 1H). Three exchangeable protons not observed. | System 2<br>Method 2 | m/z 302.2 $(M + H)^+$ (ES+), at 1.96 min, 254 nm |
| 15 | 4-(5-Chloro-1-methyl-1H-pyrazol-4-yl)-6-(3-(methylamino)azetidin-1-yl)pyrimidin-2-amine | C<br>11, 12, 13, 14 & 2 | RP HPLC<br>Method O | 1H NMR (400 MHz, Methanol-d4) δ 2.78 (s, 3H), 3.95 (s, 3H), 4.32-4.18 (m, 1H), 4.43-4.32 (m, 2H), 4.54-4.73 (m, 2H), 6.30 (s, 1H), 8.01 (s, 1H). Three exchangeable protons not observed. | System 2<br>Method 1 | m/z 294.2 $(M + H)^+$ (ES+), at 2.22 min, 245 nm |
| 16 | 4-(1-(Difluoromethyl)-5-methyl-1H-pyrazol-4-yl)-6-(3-(methylamino)azetidin-1-yl)pyrimidin-2-amine | B<br>8, 9, 10, 3 & 5 | RP HPLC<br>Method D | 1H NMR (400 MHz, Methanol-d4) δ 2.66 (s, 3H), 2.78 (s, 3H), 4.23-4.31 (m, 1H), 4.33-4.46 (m, 2H), 4.54-4.71 (m, 2H), 6.13 (s, 1H), 7.65 (t, J = 57.8 Hz, 1H), 7.96 (s, 1H). Three exchangeable protons not observed. | System 1<br>Method 2 | m/z 310.2 $(M + H)^+$ (ES+), at 2.03 min, 240 nm |
| 17 | 4-(4-Methyl-5-(trifluoromethyl)-1H-pyrazol-3-yl)-6-(3-(methylamino)azetidin-1-yl)pyrimidin-2-amine | C<br>25, 12, 13, 14 & 2 | RP HPLC<br>Method P | 1H NMR (400 MHz, Methanol-d4) δ 2.40 (s, 3H), 2.79 (s, 3H), 4.12-4.77 (m, 5H), 6.23 (s, 1H). Four exchangeable protons not observed. | System 1<br>Method 1 | m/z 328.2 $(M + H)^+$ (ES+), at 2.39 min, 245 nm |
| 18 | 4-(1,3-Dimethyl-1H-pyrazol-4-yl)-6-(3-(methylamino)azetidin-1-yl)pyrimidin-2-amine | A<br>3, 26 & 5 | RP HPLC<br>Method Q | 1H NMR (400 MHz, Methanol-d4) δ 2.43 (s, 3H), 2.78 (s, 3H), 3.91 (s, 3H), 4.13-4.77 (m, 5H), 6.03 (s, 1H), 8.09 (s, 1H). Three exchangeable protons not observed. | System 2<br>Method 1 | m/z 274.3 $(M + H)^+$ (ES+), at 1.89 min, 202 nm |
| 19 | 4-(3-Methyl-1-(2,2,2-trifluoroethyl)-1H-pyrazol-4-yl)-6-(3-(methylamino)azetidin-1-yl)pyrimidin-2-amine | D<br>27, 12, 13, 14, 2 & 34 | RP HPLC<br>Method R | 1H NMR (400 MHz, Methanol-d4) δ 2.36 (s, 3H), 2.46 (s, 3H), 3.64-3.73 (m, 1H), 3.81 (dd, J = 9.0, 4.9 Hz, 2H), 4.24 (t, J = 8.0 Hz, 2H), 5.84 (s, 1H), 8.09 (s, 1H). Three exchangeable protons not observed. | System 2<br>Method 1 | m/z 342.2 $(M + H)^+$ (ES+), at 2.06 min, 240 nm |
| 20 | 4-(3-Methyl-1-(trifluoromethyl)-1H-pyrazol-4-yl)-6-(3-(methylamino)azetidin-1-yl)pyrimidin-2-amine | | | | | |
| 21 | 4-(1-Ethyl-5-methyl-1H-pyrazol-4-yl)-6-(3-(methylamino)azetidin-1-yl)pyrimidin-2-amine | C<br>28, 12, 13, 14 & 2 | RP HPLC<br>Method S | 1H NMR (400 MHz, Methanol-d4) δ 1.42 (t, J = 7.2 Hz, 3H), 2.52 (s, 3H), 2.78 (s, 3H), 4.23 (q, J = 7.2 Hz, 2H), 4.31-4.49 (m, 3H), 4.55-4.76 (m, 2H), 6.01 (s, 1H), 7.84 (s, 1H). Three exchangeable protons not observed. | System 1<br>Method 2 | m/z 288.2 $(M + H)^+$ (ES+), at 1.82 min, 243 nm |
| 22 | 4-(1-Isopropyl-5-methyl-1H-pyrazol-4-yl)-6-(3-(methylamino)azetidin-1-yl)pyrimidin-2-amine | C<br>29, 12, 13, 14 & 2 | RP HPLC<br>Method T | 1H NMR (400 MHz, Methanol-d4) δ 1.48 (d, J = 6.6 Hz, 6H), 2.51 (s, 3H), 2.77 (s, 3H), 4.21-4.30 (m, 1H), 4.31-4.45 (m, 2H), 4.54-4.65 (m, 2H), 4.65-4.75 (m, 1H), 6.01 (s, 1H), 7.85 (s, 1H). Three exchangeable protons not observed. | System 1<br>Method 2 | m/z 302.3 $(M + H)^+$ (ES+), at 1.99 min, 243 nm |

TABLE 3-continued

Example compounds

| Ex. No. | Name | Synthetic Method and Intermediates Used | Purification or Isolation Method | $^1$H NMR | LCMS System and Method | LCMS data |
|---|---|---|---|---|---|---|
| 23 | 4-(5-Methyl-1-(trifluoromethyl)-1H-pyrazol-4-yl)-6-(3-(methylamino)azetidin-1-yl)pyrimidin-2-amine | | | | | |
| 24 | 4-(1,3-Dimethyl-1H-pyrazol-5-yl)-6-(3-(methylamino)azetidin-1-yl)pyrimidin-2-amine | A 3, 30 & 5 | RP HPLC Method U | 1H NMR (400 MHz, Methanol-d4) δ 2.28 (s, 3H), 2.78 (s, 3H), 3.95 (s, 3H), 4.22-4.31 (m, 1H), 4.34-4.47 (m, 2H), 4.57-4.70 (m, 2H), 6.25 (s, 1H), 6.53 (s, 1H). Three exchangeable protons not observed. | System 1 Method 2 | m/z 274.3 $(M + H)^+$ (ES+), at 1.83 min, 254 nm |
| 25 | 4-(3-Ethyl-1-methyl-1H-pyrazol-5-yl)-6-(3-(methylamino)azetidin-1-yl)pyrimidin-2-amine | C 31, 12, 13, 14 & 2 | RP HPLC Method V | 1H NMR (400 MHz, Methanol-d4) δ 1.26 (t, J = 7.6 Hz, 3H), 2.61-2.73 (m, 2H), 2.78 (s, 3H), 3.96 (s, 3H), 4.21-4.33 (m, 1H), 4.36-4.51 (m, 3H), 4.55-4.73 (m, 2H), 6.28 (s, 1H), 6.59 (s, 1H). Three exchangeable protons not observed. | System 1 Method 2 | m/z 288.3 $(M + H)^+$ (ES+), at 1.99 min, 244 nm |
| 26 | 4-(3-Chloro-1-methyl-1H-pyrazol-5-yl)-6-(3-(methylamino)azetidin-1-yl)pyrimidin-2-amine | C 32, 12, 13, 14 & 2 | RP HPLC Method W | 1H NMR (400 MHz, Methanol-d4) δ 2.77 (s, 3H), 3.99 (s, 3H), 4.20-4.31 (m, 1H), 4.31-4.50 (m, 2H), 4.54-4.66 (m, 2H), 6.29 (s, 1H), 6.70 (s, 1H). Three exchangeable protons not observed. | System 2 Method 1 | m/z 294.2 $(M + H)^+$ (ES+), at 2.10 min, 214 nm |
| 27 | 4-(1-Methyl-3-(trifluoromethyl)-1H-pyrazol-5-yl)-6-(3-(methylamino)azetidin-1-yl)pyrimidin-2-amine | A 3, 33 & 5 | RP HPLC Method X | 1H NMR (400 MHz, Methanol-d4) δ 2.78 (s, 3H), 3.31 (s, 2H), 4.23-4.35 (m, 1H), 4.36-4.55 (m, 3H), 4.58-4.75 (m, 2H), 6.38 (s, 1H), 7.09 (s, 1H). Three exchangeable protons not observed. | System 2 Method 2 | m/z 328.2 $(M + H)^+$ (ES+), at 2.57 min, 254 nm |
| 28 | 4-(3,5-Dichloro-1-methyl-1H-pyrazol-4-yl)-6-(3-(methylamino)azetidin-1-yl)pyrimidin-2-amine | D 35, 12, 13, 14, 2 & 34 | RP HPLC Method Y | 1H NMR (400 MHz, Methanol-d4) δ 2.80 (s, 3H), 3.94 (s, 3H), 4.25-4.33 (m, 1H), 4.35-4.45 (m, 2H), 4.59-4.71 (m, 2H), 6.23 (s, 1H). Three exchangeable protons not observed. | System 1 Method 1 | m/z 328.2 $(M + H)^+$ (ES+), at 2.02 min, 304 nm |
| 29 | 4-(3-Chloro-1-methyl-1H-pyrazol-4-yl)-6-(3-(methylamino)azetidin-1-yl)pyrimidin-2-amine | C 36, 12, 13, 14 & 2 | RP HPLC Method Z | 1H NMR (400 MHz, Methanol-d4) δ 2.81 (s, 3H), 3.97 (s, 3H), 4.24-4.32 (m, 1H), 4.34-4.48 (m, 2H), 4.58-4.72 (m, 2H), 6.36 (s, 1H), 8.27 (s, 1H). Three exchangeable protons not observed. | System 1 Method 1 | m/z 294.2 $(M + H)^+$ (ES+), at 1.89 min, 310 nm |
| 30 | 4-(5-Bromo-1-methyl-1H-pyrazol-4-yl)-6-(3-(methylamino)azetidin-1-yl)pyrimidin-2-amine | C 37, 12, 13, 14 & 2 | RP HPLC Method AA | 1H NMR (400 MHz, Methanol-d4) δ 2.78 (s, 3H), 3.99 (s, 3H), 4.21-4.33 (m, 1H), 4.33-4.48 (m, 2H), 4.55-4.73 (m, 3H), 6.36 (s, 1H), 7.99 (s, 1H). Three exchangeable protons not observed. | System 2 Method 1 | m/z 338.2 $(M + H)^+$ (ES+), at 1.87 min, 243 nm |
| 31 | 4-(3-Bromo-1-methyl-1H-pyrazol-4-yl)-6-(3-(methylamino)azetidin-1-yl)pyrimidin-2-amine | D 41, 12, 13, 14, 2 & 34 | RP HPLC Method AF | 1H NMR (400 MHz, Methanol-d4) δ 2.81 (s, 3H), 3.99 (s, 3H), 4.25-4.33 (m, 1H), 4.34-4.46 (m, 2H), 4.58-4.72 (m, 2H), 6.41 (s, 1H), 8.21 (s, 1H). Three exchangeable protons not observed. | System 1 Method 2 | m/z 338.2 $(M + H)^+$ (ES+), at 1.91 min, 242 nm |
| 32 | 4-(3-(Methylamino)azetidin-1-yl)-6-(1-(trifluoromethyl)-1H-pyrazol-4-yl)pyridin-2-amine | | | | | |
| 33 | (R)-4-(3-(Methylamino)pyrrolidin-1-yl)-6-(1-(trifluoromethyl)-1H-pyrazol-4-yl)pyridin-2-amine | | | | | |

TABLE 3-continued

Example compounds

| Ex. No. | Name | Synthetic Method and Intermediates Used | Purification or Isolation Method | $^1$H NMR | LCMS System and Method | LCMS data |
|---|---|---|---|---|---|---|
| 34 | (R)-4-(3-Chloro-1-methyl-1H-pyrazol-4-yl)-6-(3-(methylamino)pyrrolidin-1-yl)pyrimidin-2-amine | C<br>36, 12, 13, 14 & 15 | RP HPLC Method AB | 1H NMR (400 MHz, Methanol-d4) δ 1.83-2.01 (m, 1H), 2.20-2.32 (m, 2H), 2.45 (s, 3H), 3.33-3.37 (m, 2H), 3.45-3.57 (m, 2H), 3.91 (s, 3H), 6.38 (s, 1H), 8.04 (s, 1H). Three exchangeable protons not observed. | System 1<br>Method 1 | m/z 308.2 $(M + H)^+$ (ES+), at 1.92 min, 241 nm |
| 35 | 4-(5-Methyl-1H-pyrazol-3-yl)-6-(3-(methylamino)azetidin-1-yl)pyrimidin-2-amine | D<br>43, 12, 13, 14, 2 & 34 | RP HPLC Method AH | 1H NMR (400 MHz, Methanol-d4) δ 2.39 (s, 3H), 2.80 (s, 3H), 4.21-4.49 (m, 3H), 4.53-4.75 (m, 2H), 6.46 (s, 1H), 6.73 (s, 1H). Four exchangeable protons not observed. | System 1<br>Method 2 | m/z 260.3 $(M + H)^+$ (ES+), at 1.67 min, 240 nm |
| 36 | 4-(3-(Methylamino)azetidin-1-yl)-6-(1H-pyrazol-3-yl)pyrimidin-2-amine | E<br>1, 44, 5, & 2 | RP HPLC Method AI | 1H NMR (400 MHz, Methanol-d4) δ 2.39 (s, 3H), 3.67-3.77 (m, 1H), 3.81-3.91 (m, 2H), 4.24-4.34 (m, 2H), 6.18 (s, 1H), 6.47-6.53 (m, 1H), 7.73-7.78 (m, 1H), 7.81 (d, J = 2.68 Hz, 1H). Three exchangeable protons not observed. | System 1<br>Method 2 | m/z 246.2 $(M + H)^+$ (ES+), at 1.87 min, 242 nm |
| 37 | 4-(3-(Methylamino)azetidin-1-yl)-6-(3-(trifluoromethyl)-1H-pyrazol-4-yl)pyrimidin-2-amine | A<br>3, 38 & 5 | RP HPLC Method AC | 1H NMR (400 MHz, Methanol-d4) δ 2.79 (s, 3H), 4.24-4.42 (m, 3H), 4.58-4.68 (m, 2H), 6.14 (s, 1H), 8.31 (s, 1H). Five exchangeable protons not observed. | System 1<br>Method 1 | m/z 314.3 $(M + H)^+$ (ES+), at 1.93 min, 304 nm |
| 38 | 4-(3-(Methylamino)azetidin-1-yl)-6-(1H-pyrazol-4-yl)pyrimidin-2-amine | A<br>3, 42 & 5 | RP HPLC Method AG | 1H NMR (400 MHz, Methanol-d4) δ 2.80 (s, 3H), 4.24-4.32 (m, 1H), 4.33-4.49 (m, 2H), 4.56-4.72 (m, 2H), 6.06 (s, 1H), 8.04 (s, 1H). Four exchangeable protons not observed. | System 1<br>Method 2 | m/z 314.3 $(M + H)^+$ (ES+), at 1.43 min, 260 nm |
| 39 | 4-(3-Methyl-1H-pyrazol-4-yl)-6-(3-(methylamino)azetidin-1-yl)pyrimidin-2-amine | A<br>3, 39 & 5 | RP HPLC Method AD | 1H NMR (400 MHz, Methanol-d4) δ 2.54 (s, 3H), 2.84 (s, 3H), 4.23-4.32 (m, 1H), 4.32-4.48 (m, 2H), 4.56-4.72 (m, 2H), 6.41 (s, 1H), 8.33 (s, 1H). Four exchangeable protons not observed. | System 1<br>Method 2 | m/z 260.3 $(M + H)^+$ (ES+), at 1.53 min, 241 nm |
| 40 | 4-(5-Ethyl-4-methyl-1H-pyrazol-3-yl)-6-(3-(methylamino)azetidin-1-yl)pyrimidin-2-amine | H<br>53, 12, 13, 14, 2 & 34 | RP HPLC Method AK | 1H NMR (400 MHz, Methanol-d4) δ 1.26 (t, J = 7.6 Hz, 3H), 2.26 (s, 3H), 2.70 (d, J = 7.6 Hz, 2H), 2.80 (s, 3H), 4.22-4.52 (m, 3H), 4.52-4.76 (m, 2H), 6.18 (s, 1H). Four exchangeable protons not observed. | System 1<br>Method 1 | m/z 288.4 $(M + H)^+$ (ES+), at 2.04 min, 304 nm |
| 41 | 4-(5-Ethyl-1H-pyrazol-3-yl)-6-(3-(methylamino)azetidin-1-yl)pyrimidin-2-amine | D<br>45, 12, 13, 14, 2 & 34 | RP HPLC Method AJ | 1H NMR (400 MHz, Methanol-d4) δ 1.34 (t, J = 7.6 Hz, 3H), 2.78 (q, J = 7.6 Hz, 2H), 4.25-4.50 (m, 3H), 4.58-4.74 (m, 2H), 6.50 (s, 1H), 6.78 (s, 1H). Four exchangeable protons not observed. | System 1<br>Method 2 | m/z 274.3 $(M + H)^+$ (ES+), at 1.85 min, 202 nm |
| 42 | 4-(4,5-Dichloro-1H-pyrazol-3-yl)-6-(3-(methylamino)azetidin-1-yl)pyrimidin-2-amine | C<br>40, 12, 13, 14 & 2 | RP HPLC Method AE | 1H NMR (400 MHz, Methanol-d4) δ 2.78 (s, 3H), 4.14-4.26 (m, 3H), 4.43-4.53 (m, 2H), 6.46 (s, 1H). Four exchangeable protons not observed. | System 2<br>Method 1 | m/z 313.2 $(M + H)^+$ (ES+), at 2.71 min, 245 nm |

BIOLOGICAL ACTIVITY

Example A

H4 Antagonist Functional cAMP Gi Assay

HEKf cells were infected overnight using baculovirus expressing the human H4 receptor, then centrifuged at 1,200 rpm for 5 min, frozen in cell freezing medium (Sigma) and stored at −150 °C. On the day of assay, the cells were thawed and resuspended in HBSS with 500 nM IBMX to achieve a density of 1,500 cells/well. H4 ligands were prepared in DMSO and stamped by LabCyte ECHO acoustic dispensing at 25 nL in low volume plates. 10 μL/well cells were plated in the presence of 1 pM forskolin, subjected to centrifugation at 1,200 rpm for 1 min and incubated for 30 min prior to addition of Cisbio cAMP detection reagents to a total volume 20 μL/well. For the antagonist assay, cells were pre-incubated with H4 antagonist ligands for 30 min prior to addition of EC80 concentration of histamine and a further 30 min incubation. Following detection reagent addition and shaking at room temperature for 60 min, cAMP accumulation was measured using HTRF on a PheraStar plate reader. EC50 values were generated using a 4-parameter logistical fit equation to quantify agonist potencies. Functional antagonist affinity values were generated using the Cheng-Prusoff equation to calculate a pKb value using the antagonist assay data.

H4 Antagonist Functional Dynamic Mass Redistribution Assay

HEKf cells were infected using baculovirus expressing the human H4 receptor, plated into fibronectin-coated EPIC plates at a density of 10,000 cells/well and incubated overnight at 37 °C. The medium on cells was changed to 30 μL HBSS with 20 mM HEPES per well and 30 nL DMSO were added per well by LabCyte ECHO acoustic dispensing. Following 2 h equilibration at room temperature, 30 nL of H4 ligands prepared in DMSO were stamped by LabCyte ECHO acoustic dispensing into seeded EPIC plates and cellular dynamic mass redistribution was monitored using a Corning EPIC plate reader. Following 45 min measurement, 30 nL/well of histamine EC80 was added and monitored to obtain antagonist assay data. Maximum baseline-corrected responses in pm were used to generate concentration response curves. EC50 values were generated using a 4-parameter logistical fit equation to quantify agonist potencies. Functional antagonist affinity values were generated using the Cheng-Prusoff equation to calculate a pKb value using the antagonist assay data.

hERG Assay hERG assay data was determined by Metrion Biosciences, Cambridge, UK, using the experimental protocols detailed below:

A Chinese Hamster Ovary (CHO) cell line stably expressing the human ether-á-go-go related gene was grown and passaged under standard culture conditions. Cells were prepared for assays using dissociation protocols designed to optimise cell health, yield, and seal and assay quality. Test samples were provided as 10 mM stock solutions in 100% DMSO. All sample handling and serial dilutions were performed using glass containers and glass-lined plates. A top working concentration of 30 μM was prepared from the 10 mM sample stock solution using a 1:333-fold dilution into external recording solution (0.3% DMSO v/v). In the single-concentration assay, test samples were screened at 30 μM against a minimum of three separate cells. In the $pIC_{50}$ assay, test samples were screened at 1, 3, 10 and 30 μM against a minimum of three separate cells. Each four-point concentration-response curve was constructed using cumulative double sample additions of each concentration to the same cell.

All experiments were performed on the QPatch automated patch clamp platform. The composition of external and internal recording solutions for the QPatch experiments is shown in Table A below. All solutions were filtered (0.2 μm) prior to each experiment.

TABLE A

The composition of external and internal solutions (in mM) used in the hERG study

| Constituent | Intracellular Solution (mM) | Extracellular Solution (mM) |
|---|---|---|
| NaCl | — | 140 |
| KCl | 70 | 2 |
| KF | 60 | — |
| HEPES | 10 | 10 |
| $MgCl_2$ | — | 1 |
| $CaCl_2$ | — | 2 |
| Glucose | — | 5 |
| EGTA | 5 | — |
| MgATP | 5 | — |
| pH | 7.2 (KOH) | 7.4 (NaOH) |

All recordings were made in the conventional whole-cell configuration and performed at room temperature (~21 °C) using standard single hole chips (Rchip 1.5-4 MΩ). Series resistance (4-15 MΩ) was compensated by >80%. Currents were elicited from a holding potential of −90 mV using the industry standard "+40/−40" voltage protocol as shown below; this was applied at a stimulus frequency of 0.1 Hz.

On achieving the whole-cell configuration, vehicle (0.3% DMSO v/v in external recording solution) was applied to each cell in two bolus additions with a two-minute recording period between each addition to allow stable recordings to be achieved. Following the vehicle period, either:

i) For the single concentration assay—a single concentration of test sample was applied at 30 μM as five bolus additions per test concentration at two-minute intervals; or ii) For the $pIC_{50}$ assay—four concentrations of test sample were applied from 1 μM to 30 μM as two bolus additions per test concentration at two-minute intervals;

and then the effects on hERG tail current amplitude were measured during the four-minute recording period. For each sweep of the voltage protocol, membrane current and the passive properties of the individual cells were recorded by the QPatch assay software. Peak outward tail current amplitude elicited during the test pulse to −40 mV was measured relative to the instantaneous leak current measured during the initial pre-pulse step to −40 mV. For QC purposes, the minimum current amplitude for the assay is >200 pA peak outward current, measured at the end of the vehicle period. The QPatch analysis software calculates the mean peak current for the last three sweeps at the end of each concentration application period and the data is exported to Excel and interrogated using a bioinformatics suite developed running in Pipeline Pilot (Biovia, USA). The template calculates percent inhibition for each test concentration application period as the reduction in mean peak current or charge relative to the value measured at the end of the control (i.e. vehicle) period. The percent inhibition values from each cell are used to construct concentration-response curves employing a four-parameter logistic fit with 0 and 100% inhibition levels fixed at very low and very high concentrations, respectively, and a free Hill slope factor. The $IC_{50}$ (50% inhibitory concentration) and Hill coefficient are then determined, but only data from cells with Hill slopes within 0.5>nH<2.0 are included. The $IC_{50}$ data reported below represents the mean of at least three separate cells (N≥3). By convention, a test sample that fails to achieve >40% block at the top concentration will yield an ambiguous $IC_{50}$ value due to a poor or unconstrained fit. In this instance an arbitrary $IC_{50}$ value is returned that is 0.5 log unit above the highest concentration tested. For example, if a sample fails to demonstrate a mean inhibition of >40% block at a top concentration of 30 μM then an $IC_{50}$ value of 100 μM is reported, i.e. $pIC_{50}$≤4.0.

| Ex. No. | Human H4 DMR $fpK_b$ | hERG $pIC_{50}$ |
|---|---|---|
| Thioperamide[1] | 6.5 | — |
| JNJ-7777120[2] | 8.5 | ≤4.0 |
| JNJ-39758979[3] | 8.5 | ≤4.0 |
| Toreforant[4] | 7.9 | 5.5 |
| PF-3893787[5] | 9.1 | 5.1 |
| Compound 61[6] | 9.1 | 5.2 |
| Compound 48[7] | 9.0 | — |
| 1 | 8.9 | <4.0 |
| 2 | 7.8 | <4.0 |
| 3 | 8.4 | <4.0 |
| 4 | 8.6 | <4.0 |
| 5 | 8.4 | <4.0 |
| 6 | 7.9 | <4.0 |
| 7 | 8.1 | 4.37 |
| 8 | 8.1 | 4.63 |
| 9 | 7.9 | <4.0 |
| 10 | 8.3 | <4.0 |
| 11 | 8.0 | <4.0 |
| 12 | 8.1 | 4.41 |
| 13 | 8.0 | <4.0 |
| 14 | 7.0 | 4.54 |
| 15 | 8.1 | <4.0 |
| 16 | 8.7 | <4.0 |
| 17 | 9.0 | <4.0 |
| 18 | 8.1 | <4.0 |
| 19 | 7.3 | <4.5 |
| 20 | — | — |
| 21 | 8.6 | <4.0 |
| 22 | 8.1 | <4.0 |
| 23 | — | — |
| 24 | 6.9 | <4.0 |
| 25 | 7.0 | — |
| 26 | 7.8 | <4.0 |
| 27 | 7.8 | 4.35 |
| 28 | — | — |
| 29 | 8.8 | <4.0 |
| 30 | 8.8 | <4.0 |
| 31 | 8.1 | <4.5 |
| 32 | — | — |
| 33 | — | — |
| 34 | — | — |
| 35 | 8.4 | <4.5 |
| 36 | — | — |
| 37 | 7.5 | <4.5 |
| 38 | 8.3 | <4.5 |
| 39 | 8.4 | <4.5 |
| 40 | — | <4.5 |
| 41 | 8.1 | <4.5 |
| 42 | 8.2 | <4.0 |

[1]Changlu Liu et al., J Pharmacol Exp Ther., 299, (2001), 121-130.
[2]Jennifer D. Venable et al., J. Med. Chem., 48, (2005), 8289-8298.
[3]Brad M. Savall et al., J. Med. Chem., 57, (2014), 2429-2439.
[4]Robin L Thurmond et al., Ann Pharmacol Pharm., 2, (2017), 1-11.
[5]Charles E. Mowbray et al., Bioorg. Med. Chem. Lett., 21, (2011), 6596-6602.
[8]Rogier A. Smits et al., Bioorg. Med. Chem. Lett., 23, (2013), 2663-2670.
[7]Chan-Hee Park et al., J. Med. Chem., 61, (2018), 2949-2961.

The invention claimed is:

1. A compound selected from the group consisting of:

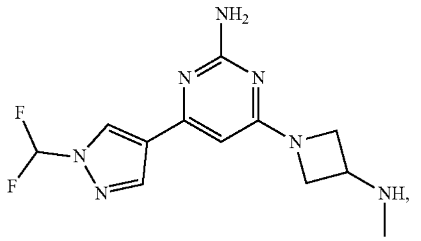

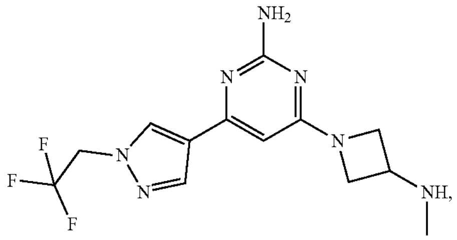

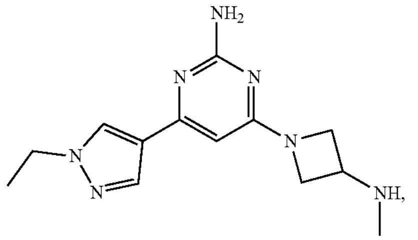

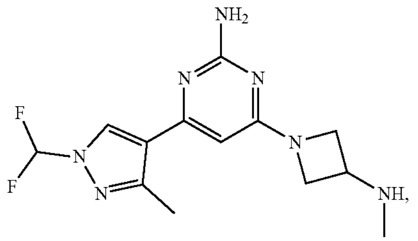

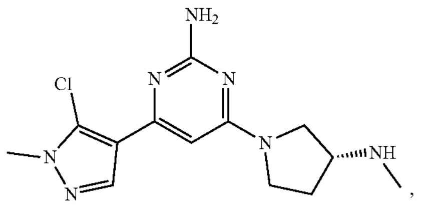

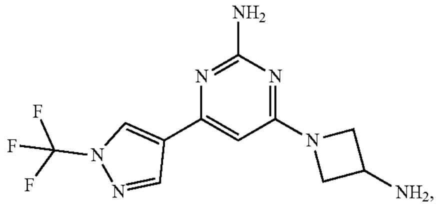

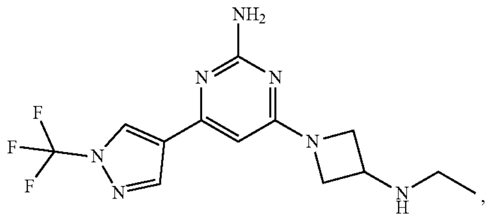

-continued
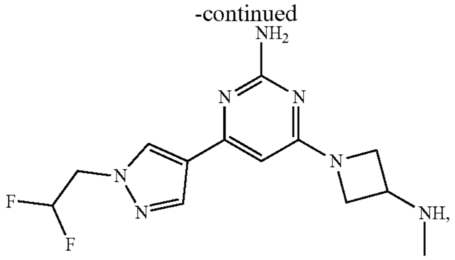
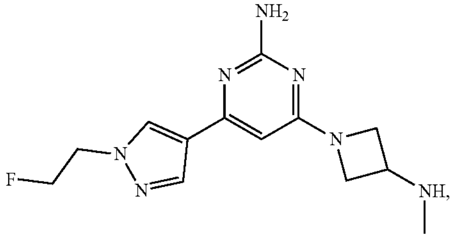
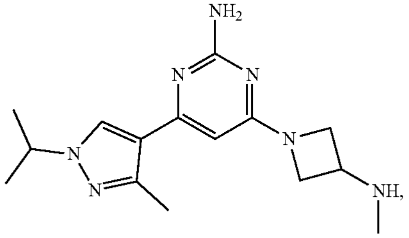
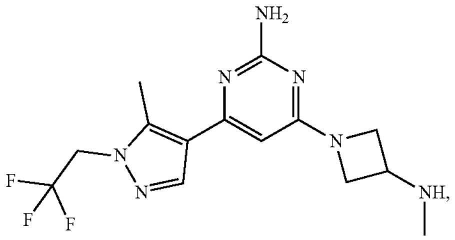
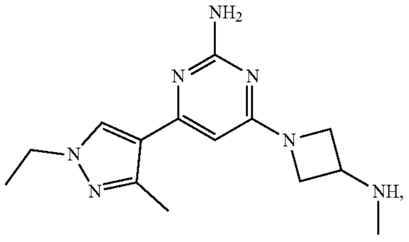
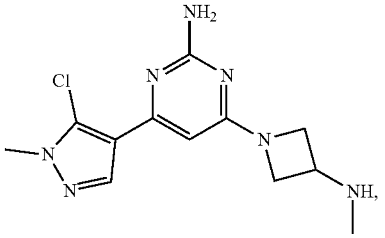
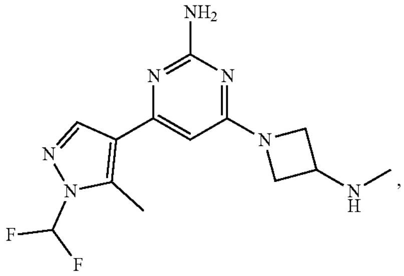
-continued
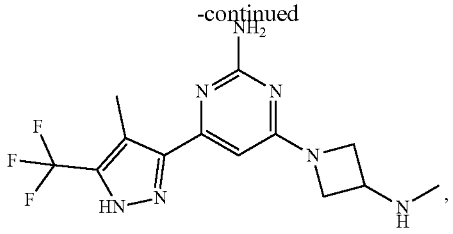
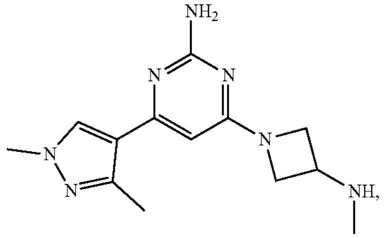
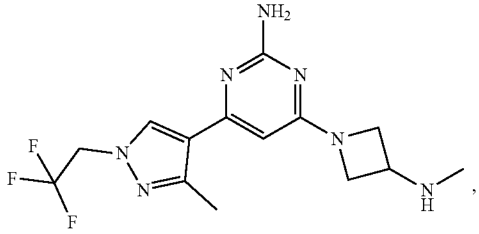
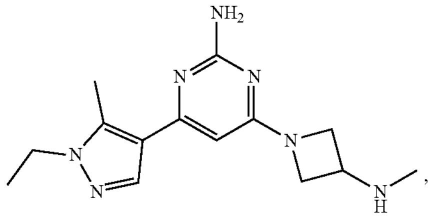
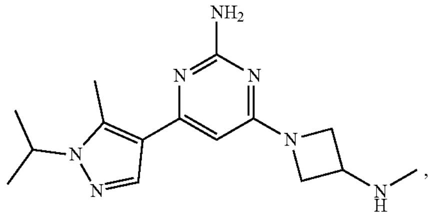
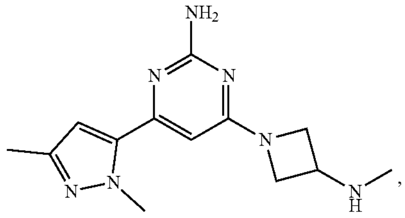
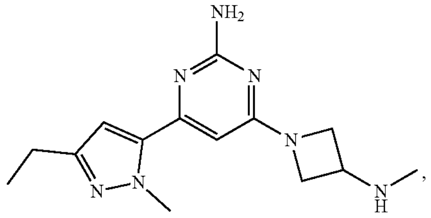

-continued
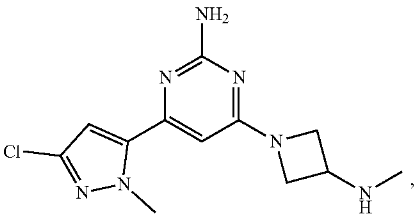
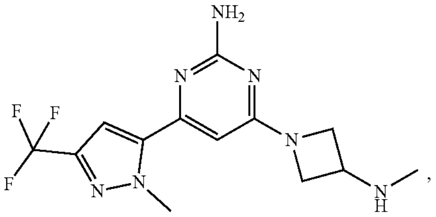
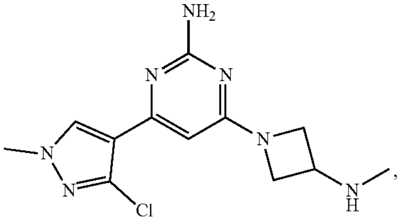
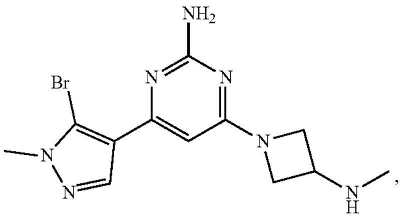
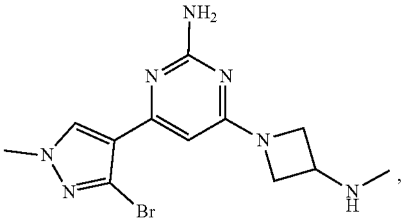
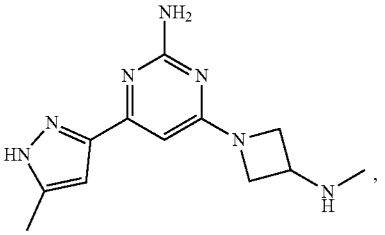
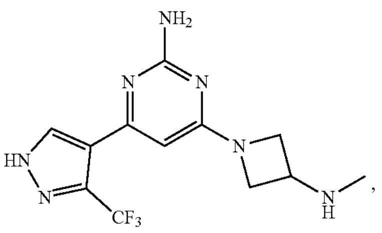
-continued
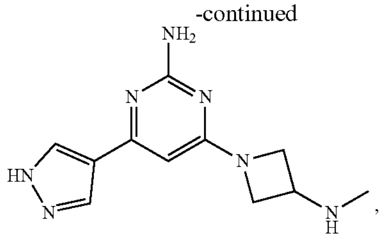
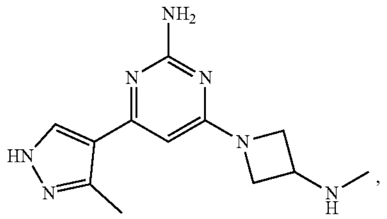
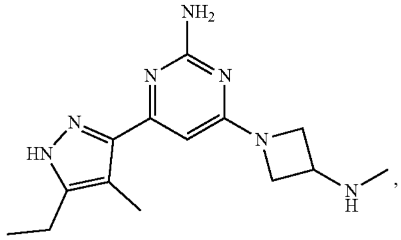
and
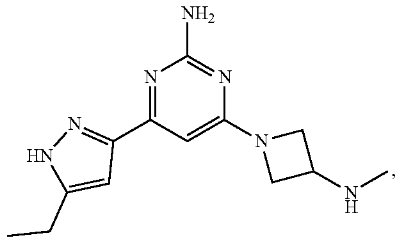
or a salt thereof.
2. The compound according to claim 1 which is selected from the group consisting of:
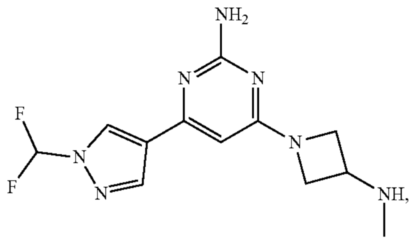
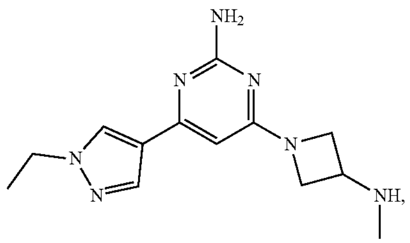

-continued

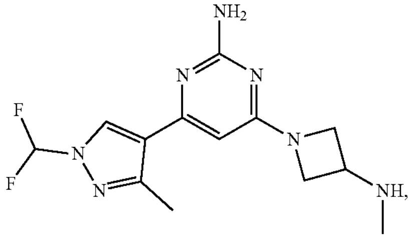

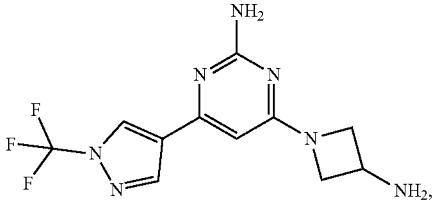

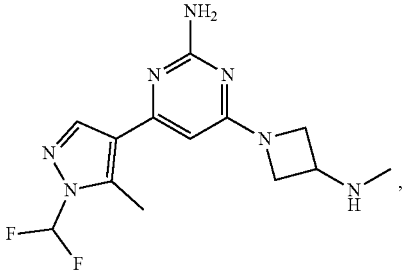

and

-continued

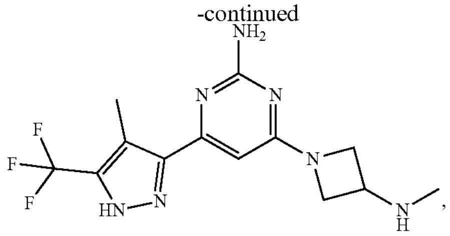

or a salt thereof.

3. A pharmaceutically acceptable salt of a compound according to claim 1.

4. A pharmaceutical composition comprising a compound as defined in claim 1 and a pharmaceutically acceptable excipient.

5. The compound according to claim 1 having H4 receptor activity.

6. The compound according to claim 5 which exhibits low hERG activity.

7. A pharmaceutically acceptable salt of a compound according to claim 2.

8. A pharmaceutical composition comprising a compound as defined in claim 2 and a pharmaceutically acceptable excipient.

9. A pharmaceutical composition comprising a compound as defined in claim 3 and a pharmaceutically acceptable excipient.

* * * * *